United States Patent
Kindermann et al.

(10) Patent No.: US 7,799,524 B2
(45) Date of Patent: Sep. 21, 2010

(54) SUBSTRATES FOR O6-ALKYLGUANINA-DNA ALKYLTRANSFERASE

(75) Inventors: Maik Kindermann, Basel (CH); Kai Johnsson, Lausanne (CH); Christoph Bieri, Basel (CH)

(73) Assignee: Ecole Polytechnique Ferdeale de Lausanne, Lausanne (CH)

( * ) Notice: Subject to any disclaimer, the term of this patent is extended or adjusted under 35 U.S.C. 154(b) by 671 days.

(21) Appl. No.: 10/529,651

(22) PCT Filed: Oct. 1, 2003

(86) PCT No.: PCT/EP03/10889

§ 371 (c)(1), (2), (4) Date: Mar. 31, 2005

(87) PCT Pub. No.: WO2004/031405

PCT Pub. Date: Apr. 15, 2004

(65) Prior Publication Data

US 2006/0024775 A1    Feb. 2, 2006

(30) Foreign Application Priority Data

Oct. 3, 2002    (EP) .................................. 02405854

(51) Int. Cl.
*C07D 473/18* (2006.01)
*C07D 519/00* (2006.01)
*C12Q 1/68* (2006.01)
*G01N 33/53* (2006.01)
*C07D 495/04* (2006.01)
*C07F 7/18* (2006.01)

(52) U.S. Cl. .............................. 435/6; 435/7.5; 435/7.1; 536/27.81; 544/265; 544/269; 544/270; 544/271; 544/272; 544/276; 544/260; 548/303.7; 556/444

(58) Field of Classification Search ................. 544/265, 544/269, 270, 271, 272, 276, 260; 536/27.81
See application file for complete search history.

(56) References Cited

U.S. PATENT DOCUMENTS

| | | | |
|---|---|---|---|
| 4,587,206 A * | 5/1986 | Sakaguchi et al. .......... 430/348 |
| 5,091,430 A | 2/1992 | Moschel et al. |
| 5,352,669 A | 10/1994 | Moschel et al. |
| 5,358,952 A | 10/1994 | Moschel et al. |
| 5,691,307 A | 11/1997 | Moschel et al. |
| 5,929,046 A | 7/1999 | McMurry et al. |
| 6,096,724 A * | 8/2000 | McMurry et al. .............. 514/45 |
| 2004/0115130 A1* | 6/2004 | Johnsson et al. ............ 424/1.69 |
| 2006/0024775 A1* | 2/2006 | Kindermann et al. ....... 544/277 |
| 2006/0183783 A1* | 8/2006 | Polisetti et al. .............. 514/370 |
| 2007/0082336 A1* | 4/2007 | Johnsson et al. ................ 435/6 |
| 2007/0099871 A1* | 5/2007 | Davis et al. .................... 514/80 |
| 2007/0243568 A1* | 10/2007 | Jaccard et al. ................. 435/15 |
| 2008/0039321 A1* | 2/2008 | Bastiaans et al. ............. 544/277 |
| 2008/0119454 A1* | 5/2008 | Polisetti et al. ........... 514/217.1 |
| 2008/0119455 A1* | 5/2008 | Polisetti et al. ........... 514/217.1 |

FOREIGN PATENT DOCUMENTS

| | | |
|---|---|---|
| DE | 199 03 895 | 8/2000 |
| WO | 97/20843 | 6/1997 |
| WO | WO 9850031 A1 * | 11/1998 |
| WO | 01/85221 | 11/2001 |
| WO | 02/083937 | 10/2002 |

OTHER PUBLICATIONS

Baker et al., Journal of Medicinal Chemistry (1968), 11(4), 652-5.*
Vaidyanathan et al., Bioconjugate Chem. 2000, 17, 868-875.*
Damoiseaux, et al., ChemBioChem vol. 2, Issue 4 , pp. 285-287 (2001).*
Gibson et al., Journal of Medicinal Chemistry (2002), 45(16), 3381-3393.*
Zheng, J Label Compd Radiopharm 2002; 45: 1239-1252.*
R. Damoiseaux et al., "Synthesis and applications of chemical probes for human 06-alkylguanine-DNA alkyltransferase", Chembiochem—A European Journal of Chemical Biology, vol. 2, No. 4, pp. 285-287, XP002231480, ISSN: 1439-4227, Apr. 2, 2001.
Antje Keppler et al., "A general method for the covalent labeling of fusion proteins with small molecules in vivo", Nature Biotechnology, Nature Publishing, US, vol. 21, No. 1, pp. 86-89, XP002231034, ISSN: 1087-0156, Jan. 20, 2003.

* cited by examiner

*Primary Examiner*—Mark L Berch
(74) *Attorney, Agent, or Firm*—Harriet M. Strimpel, D. Phil.

(57) ABSTRACT

The invention relates to compounds of formula 1

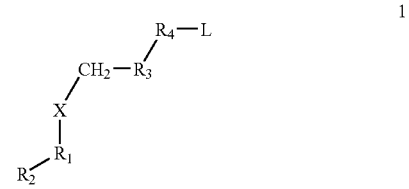

wherein $R_1$-$R_2$ is a guanine derivative; X is oxygen or sulfur; $R_3$ is a heteroaromatic, unsaturated heterocyclyl or an alkynyl group with the double or triple bond connected to $CH_2$; $R_4$ is a linker; and L is a label, a plurality of same or different labels, a bond connecting $R_4$ to $R_1$ forming a cyclic substrate, or a further group —$R_3$—$CH_2$—X—$R_1$-$R_2$. The invention relates also to methods of manufacture of such novel AGT substrates, to intermediates useful in the synthesis of such AGT substrates, and to a method of transferring a label from such AGT substrates to $O^6$-alkylguanine-DNA alkyltransferase (AGT) fusion proteins comprising proteins of interest.

23 Claims, 4 Drawing Sheets

US 7,799,524 B2

SUBSTRATES FOR O6-ALKYLGUANINA-DNA ALKYLTRANSFERASE

FIELD OF THE INVENTION

The present invention relates to methods of transferring a label from novel substrates to $O^6$-alkylguanine-DNA alkyltransferases (AGT) and $O^6$-alkylguanine-DNA alkyltransferase fusion proteins, and to novel substrates suitable in such methods.

BACKGROUND OF THE INVENTION

The mutagenic and carcinogenic effects of electrophiles such as N-methyl-N-nitrosourea are mainly due to the $O^6$-alkylation of guanine in DNA. To protect themselves against DNA-alkylation, mammals and bacteria possess a protein, $O^6$-alkylguanine-DNA alkyltransferase (AGT) which repairs these lesions. AGT transfers the alkyl group from the position O-6 of alkylated guanine and guanine derivatives to the mercapto group of one of its own cysteines, resulting in an irreversibly alkylated AGT. The underlying mechanism is a nucleophilic reaction of the $S_N 2$ type which explains why not only methyl groups, but also benzylic groups are easily transferred. As overexpression of AGT in tumour cells is the main reason for resistance to alkylating drugs such as procarbazine, dacarbazine, temozolomide and bis-2-chloroethyl-N-nitrosourea, inhibitors of AGT have been proposed for use as sensitisers in chemotherapy (Pegg et al., Prog Nucleic Acid Res Mol Biol 51: 167-223, 1995). U.S. Pat. No. 5,691,307 describes $O^6$-benzylguanines carrying various substituents in the benzyl group, and their use for depleting AGT levels in tumor cells and thereby increasing responsiveness to alkylating anti-tumor drugs. Likewise, WO 97/20843 discloses further AGT depleting compounds representing $O^6$-benzyl- and $O^6$-heteroarylmethyl-pyrimidine derivatives.

DE 199 03 895 discloses an assay for measuring levels of AGT which relies on the reaction between biotinylated $O^6$-alkylguanine derivatives and AGT which leads to biotinylation of the AGT. This in turn allows the separation of the AGT on a streptavidin coated plate and its detection, e.g. in an ELISA assay. The assay is suggested for monitoring the level of AGT in tumour issue and for use in screening for AGT inhibitors.

WO 01/85221 proposes the use of radiolabelled fluoro- or iodo-substituted $O^6$-benzyl-guanines for detection of AGT and monitoring the level of AGT.

Damoiseaux et al., ChemBiochem. 4: 285-287, 2001, disclose modified $O^6$-alkylated guanine derivatives incorporated into oligodeoxyribonucleotides for use as chemical probes for labelling AGT, again to facilitate detecting the levels of this enzyme in cancer cells to aid in research and in chemotherapy.

PCT/GB02/01636 (WO 02/083937) discloses a method for detecting and/or manipulating a protein of interest wherein the protein is fused to AGT and the AGT fusion protein contacted with an AGT substrate carrying a label, and the AGT fusion protein detected and optionally further manipulated using the label. Several AGT fusion proteins to be used, general structural principles of the AGT substrate and a broad variety of labels and methods to detect the label useful in the method are described.

SUMMARY OF THE INVENTION

The invention relates to a method for detecting and/or manipulating a protein of interest, wherein the protein of interest is incorporated into an AGT fusion protein, the AGT fusion protein is contacted with particular AGT substrates carrying a label, and the AGT fusion protein is detected and optionally further manipulated using the label in a system designed for recognising and/or handling the label.

The particular AGT substrates used in the method of the invention are $O^6$-substituted guanine derivatives or related nitrogen containing hydroxy-heterocycles and their sulfur analogs wherein the $O^6$-substituent is an activated methyl derivative suitable for transfer from guanine or the corresponding heterocycle to AGT, and further carrying a label. The label may consist of a plurality of same or different labels. Activated methyl derivatives are e.g. arylmethyl derivatives suitably substituted in the aryl ring, heteroarylmethyl derivatives suitably substituted in the heteroaryl ring, and allyl type derivatives suitably substituted at the double bond. Suitable substituents of the aryl ring, heteroaryl ring or allylic double bond are linkers connecting a label to the aryl ring, heteroaryl ring or allyl group, preferably linkers which may undergo further modification or cleavage, and also linkers which give rise to dimeric or cyclised AGT substrates. The invention relates also to the novel AGT substrates as such, to methods of manufacture of such novel substrates, and to intermediates useful in the synthesis of such novel AGT substrates.

Lanes 1 and 2 (two different concentrations) show the reaction product of compound 60 bearing a fluorescein label and a biotin label (a compound of formula 1 wherein L is a plurality of labels) with $^{PGE4}$hAGT-GST. The lane on the left side shows molecular weight markers of 47 kDa and 79 kDa.

Figure 2:
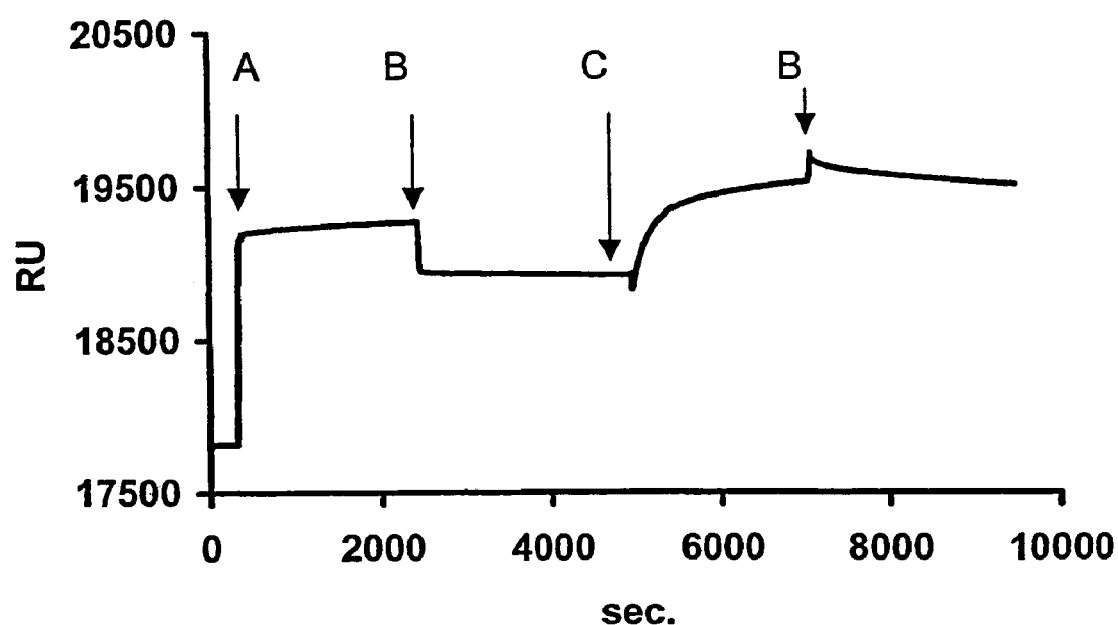

FIG. 2: Sensogram of a surface plasmon resonance of the reaction product of $^{PGE4}$hAGT-GST (an AGT fusion protein) with compound 54 (compound of formula 1 wherein L is biotin) applied to a Streptavidin Biacore chip. The chip is further treated with a solution of an αGST antibody. A: Addition of $^{PGE4}$hAGT-GST preincubated with 54. B: Addition of buffer solution (HBST). C: Addition of αGST antibody.

Figure 3:
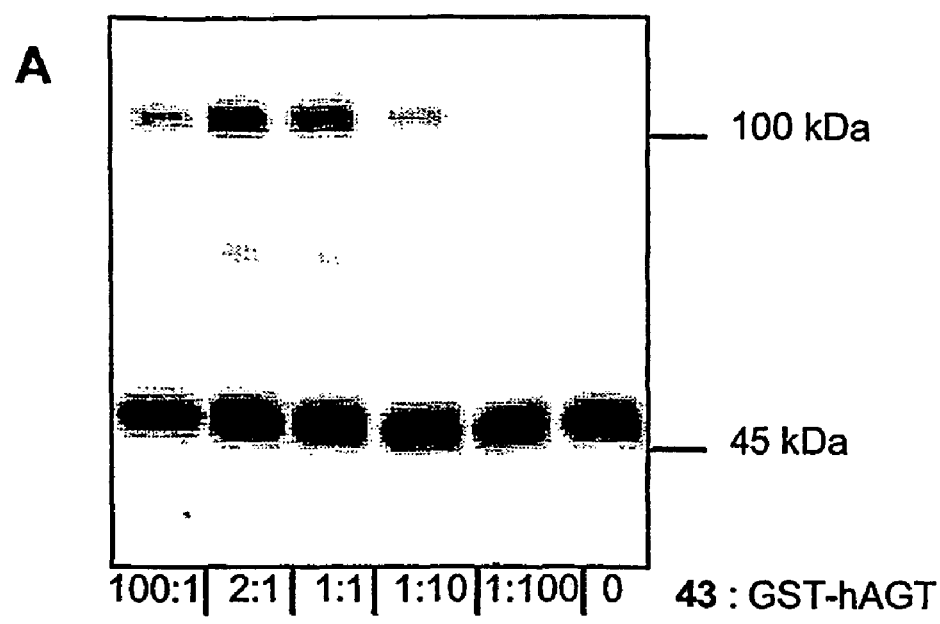
Figure 3:
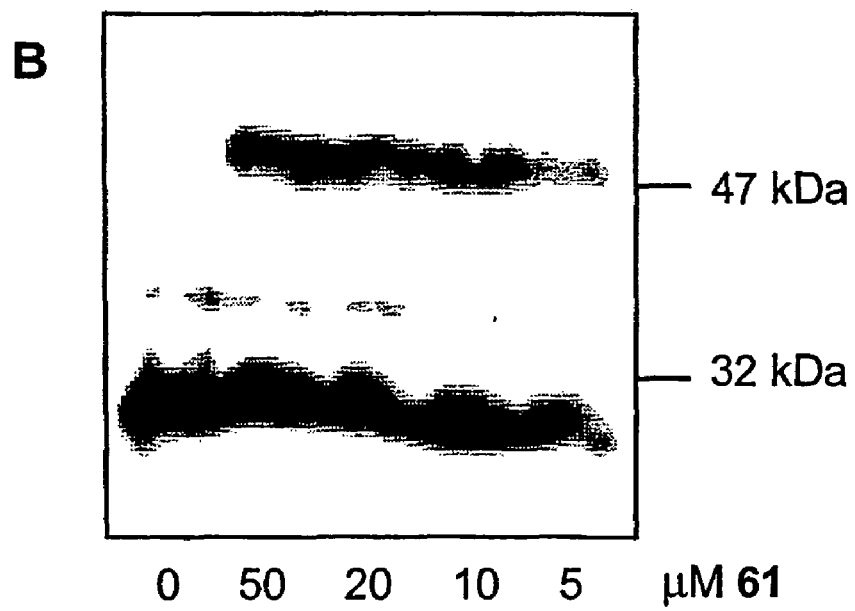

FIG. 3A: Western Blot with an anti-hAGT antibody and an anti-mouse-HRP conjugate as a second antibody. At the bottom of the lane, the ratio of compound 43 (a compound of formula 1 wherein L is a further —$R_3$—$CH_2$—X—$R_1$-$R_2$ residue, i.e. a dimerizing compound) to $^{PGEG}$hAGT-GST is shown.

FIG. 3B: Western Blot with a goat anti-hAGT and an anti-goat IgG of the in vivo reaction product of dimerizing compound 61 with fusion protein HA-$^{W160}$hAGT in *E. coli*. At the bottom of the lane, different concentrations of 61 (a compound of formula 1 wherein L is a further —R$_3$—CH$_2$—X—R$_1$-R$_2$ residue) are indicated.

Figure 4:
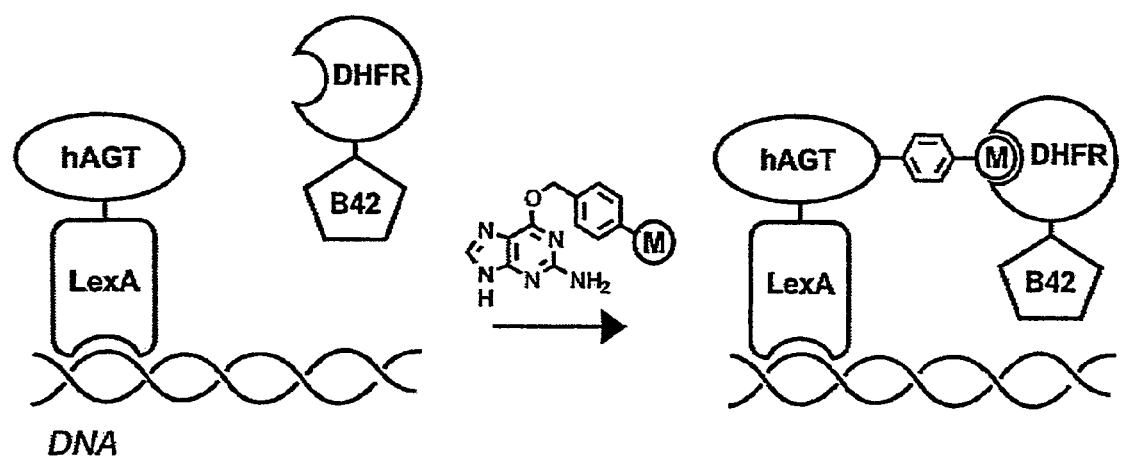

FIG. 4: Schematic representation of hAGT-based three-hybrid system. On reaction of the hAGT-LexA fusion protein with the compound of formula 1 wherein L is methotrexate (M) in the presence of a fusion protein DHFR-B42, hAGT-LexA and DHFR-B42 are coupled and transcription started.

DETAILED DESCRIPTION OF THE INVENTION

In the present invention a protein or peptide of interest is fused to an O$^6$-alkylguanine-DNA alkyltransferase (AGT). The protein or peptide of interest may be of any length and both with and without secondary, tertiary or quaternary structure, and preferably consists of at least twelve amino acids and up to 2000 amino acids. Examples of such protein or peptide of interest are provided below, and are e.g. enzymes, DNA-binding proteins, transcription regulating proteins, membrane proteins, nuclear receptor proteins, nuclear localization signal proteins, protein cofactors, small monomeric GTPases, ATP-binding cassette proteins, intracellular structural proteins, proteins with sequences responsible for targeting proteins to particular cellular compartments, proteins generally used as labels or affinity tags, and domains or subdomains of the aforementioned proteins. The protein or peptide of interest is preferably fused to AGT by way of a linker which may be cleaved by an enzyme, e.g. at the DNA stage by suitable restriction enzymes, e.g. AGATCT cleavable by Bgl II, and/or linkers cleavable by suitable enzymes at the protein stage, e.g. tobacco etch virus NIa (TEV) protease. Fusion proteins may be expressed in prokaryotic hosts, preferably *E. coli*, or eukaryotic host, e.g. yeast, insect or mammalian cells.

The O$^6$-alkylguanine-DNA alkyltransferase (AGT) has the property of transferring a label present on a substrate to one of the cysteine residues of the AGT forming part of a fusion protein. In preferred embodiments, the AGT is a known human O$^6$-alkylguanine-DNA alkyltransferase, hAGT. Murine or rat forms of the enzyme are also considered provided they have similar properties in reacting with a substrate like human AGT. In the present invention, O$^6$-alkylguanine-DNA alkyltransferase also includes variants of a wild-type AGT which may differ by virtue of one or more amino acid substitutions, deletions or additions, but which still retain the property of transferring a label present on a substrate to the AGT part of the fusion protein. AGT variants may be obtained by chemical modification using techniques well known to those skilled in the art. AGT variants may preferably be produced using protein engineering techniques known to the skilled person and/or using molecular evolution to generate and select new O$^6$-alkylguanine-DNA alkyltransferases. Such techniques are e.g. saturation mutagenesis, error prone PCR to introduce variations anywhere in the sequence, DNA shuffling used after saturation mutagenesis and/or error prone PCR, or family shuffling using genes from several species.

The fusion protein comprising protein of interest and an O$^6$-alkylguanine-DNA alkyltransferase (AGT) is contacted with a particular substrate having a label. Conditions of reaction are selected such that the AGT reacts with the substrate and transfers the label of the substrate. Usual conditions are a buffer solution at around pH 7 at room temperature, e.g. around 25° C. However, it is understood that AGT reacts also under a variety of other conditions, and those conditions mentioned here are not limiting the scope of the invention.

AGT irreversibly transfers the alkyl group from its substrate, O$^6$-alkylguanine-DNA, to one of its cysteine residues. A substrate analogue that rapidly reacts with hAGT is O$^6$-benzylguanine, the second order rate constant being approximately $10^3$ sec$^{-1}$ M$^{-1}$. Substitutions of O$^6$-benzylguanine at the C-4 of the benzyl ring do not significantly affect the reactivity of hAGT against O$^6$-benzylguanine derivatives, and this property has been used to transfer a label attached to the C-4 of the benzyl ring to AGT.

The label part of the substrate can be chosen by those skilled in the art dependent on the application for which the fusion protein is intended. After contacting the fusion protein comprising AGT with the substrate, the label is covalently bonded to the fusion protein. The labelled AGT fusion protein is then further manipulated and/or detected by virtue of the transferred label. The label may consist of a plurality of same or different labels. If the substrate contains more than one label, the corresponding labelled AGT fusion protein will also comprise more than one label which gives more options for further manipulating and/or detecting the labelled fusion protein.

The particular AGT substrates are compounds of the formula 1

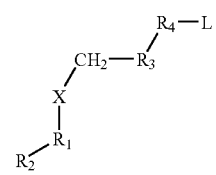

wherein R$_1$-R$_2$ is a group recognized by AGT as a substrate;

X is oxygen or sulfur;

R$_3$ is an aromatic or a heteroaromatic group, or an optionally substituted unsaturated alkyl, cycloalkyl or heterocyclyl group with the double bond connected to CH$_2$;

R$_4$ is a linker; and

L is a label, a plurality of same or different labels, a bond connecting R$_4$ to R$_1$ forming a cyclic substrate, or a further group —R$_3$—CH$_2$—X—R$_1$-R$_2$.

In a group R$_1$-R$_2$, the residue R$_1$ is preferably a heteroaromatic group containing 1 to 5 nitrogen atoms, recognized by AGT as a substrate.

A heteroaromatic group R$_1$ is mono- or bicyclic and has 5 to 12, preferably 6 or 9 or 10 ring atoms; which in addition to carrying a substituent R$_2$ may be unsubstituted or substituted by one or more, especially one, two or three further substituents selected from the group consisting of lower alkyl, such as methyl, lower alkoxy, such as methoxy or ethoxy, hydroxy, oxo, amino, lower alkylamino, di-lower alkylamino, acylamino, halogen, such as chlorine or bromine, halogenated lower alkyl, such as trifluoromethyl, carboxy, lower alkoxycarbonyl, carbamoyl, lower alkylcarbamoyl, or lower alkylcarbonyl.

Lower alkyl is preferably alkyl with 1 to 7, preferably from 1 to 4 C atoms, and is linear or branched; preferably, lower alkyl is butyl, such as n-butyl, sec-butyl, isobutyl, tert-butyl, propyl, such as n-propyl or isopropyl, ethyl or methyl. Preferably lower alkyl is methyl.

In lower alkoxy, the lower alkyl group is as defined hereinbefore. Lower alkoxy denotes preferably n-butoxy, tert-butoxy, iso-propoxy, ethoxy, or methoxy, in particular methoxy.

Preferably the mono- or bicyclic heteroaromatic group $R_1$ is selected from 2H-pyrrolyl, pyrrolyl, imidazolyl, benzimidazolyl, pyrazolyl, indazolyl, purinyl, 8-azapurinyl, pyridyl, pyrazinyl, pyrimidinyl, pyridazinyl, 4H-quinolizinyl, isoquinolyl, quinolyl, phthalazinyl, naphthyridinyl, quinoxalyl, quinazolinyl, quinolinyl, pteridinyl, indolizinyl, 3H-indolyl, indolyl, isoindolyl, triazolyl, tetrazolyl, or benzo[d]pyrazolyl. More preferably the mono- or bicyclic heteroaromatic group $R_1$ is selected from the group consisting purinyl, 8-azapurinyl, pyridyl, pyrazinyl, pyrimidinyl, and pyridazinyl.

For example the group $R_1$-$R_2$ may be a purine radical of formula 2

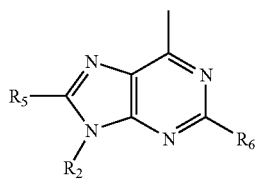

2 wherein $R_2$ is hydrogen, alkyl of 1 to 10 carbon atoms, or a saccharide moiety;

$R_5$ is hydrogen, halogen, e.g. chloro or bromo, trifluoromethyl, or hydroxy; and $R_6$ is hydrogen, hydroxy or unsubstituted or substituted amino.

If $R_5$ or $R_6$ is hydroxy, the purine radical is predominantly present in its tautomeric form wherein a nitrogen adjacent to the carbon atom bearing $R_5$ or $R_6$ carries a hydrogen atom, the double bond between this nitrogen atom and the carbon atom bearing $R_5$ or $R_6$ is a single bond, and $R_5$ or $R_6$ is double bonded oxygen, respectively.

A substituted amino group $R_6$ is lower alkylamino of 1 to 4 carbon atoms or acylamino, wherein the acyl group is lower alkylcarbonyl with 1 to 5 carbon atoms, e.g. acetyl, propionyl, n- or isopropylcarbonyl, or n-, iso- or tert-butylcarbonyl, or arylcarbonyl, e.g. benzoyl.

If $R_6$ is unsubstituted or substituted amino and the residue X connected to the bond of the purine radical is oxygen, the residue of formula 2 is a guanine derivative.

$R_2$ as alkyl of 1 to 10 carbon atoms is linear or branched and includes lower alkyl of 1 to 4 carbon atoms, e.g. methyl, ethyl, butyl, such as n-butyl, sec-butyl, isobutyl or tert-butyl, and propyl, such as n-propyl or isopropyl. $R_2$ as alkyl may also be pentyl, hexyl, heptyl, octyl, nonyl, or decyl, e.g. n-hexyl.

A saccharide moiety $R_2$ is a saccharide monomer or oligomer connected with a spacer of variable length to the $N^9$ position of the guanine base. The spacer in this context is an alkyl chain preferably from 1 to 15 carbon atoms, a polyethylene glycol spacer consisting of 1 to 200 ethylene glycol units, an amide group —CO—NH—, an ester group —CO—O—, an alkylene group —CH=CH— or a combination of alkyl chain, polyethylene glycol group, amide group, ester group, and/or alkylene group.

In the context of this invention, a saccharide moiety $R_2$ further includes a βD-2'-deoxyribosyl, or a βD-2'-deoxyribosyl being incorporated into a single stranded oligodeoxyribonucleotide having a length of 2 to 99 nucleotides, wherein the guanine derivative $R_1$ occupies any position within the oligonucleotide sequence.

Particularly preferred are compounds wherein the group $R_1$-$R_2$ is a purine radical of formula 2, $R_2$ is hydrogen, $R_5$ is hydrogen, $R_6$ is unsubstituted amino, and X is oxygen, i.e. unsubstituted guanine derivatives.

In another preferred embodiment of the invention the group $R_1$-$R_2$ is a 8-azapurine radical of formula 3

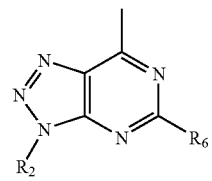

3 wherein the substituents $R_2$ and $R_6$ have the meaning as defined for $R_2$ and $R_6$ under formula 2.

In a further preferred embodiment of the invention the group $R_1$-$R_2$ is a pyrimidine radical of formula 4

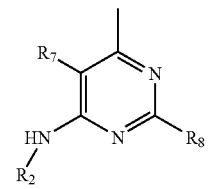

4 wherein the substituent $R_2$ has the meaning as defined under formula 2, and is preferably hydrogen; and $R_7$ and $R_8$ are both independently of one another hydrogen, halogen, e.g. chloro or bromo, lower alkyl with 1 to 4 carbon atoms, e.g. methyl, amino, or nitro.

X is preferably oxygen.

$R_3$ as an aromatic or a heteroaromatic group, or an optionally substituted unsaturated alkyl, cycloalkyl or heterocyclyl group is a group sterically and electronically accepted by AGT (in accordance with its reaction mechanism) which allows the covalent transfer of the $R_3$-$R_4$-L unit to the fusion protein. In a $R_3$-$R_4$-L unit, $R_4$-L may also have the meaning of a plurality of same or different linkers $R_4$ carrying a plurality of same or different labels L.

$R_3$ as an aromatic group is preferably phenyl or naphthyl, in particular phenyl, e.g. phenyl substituted by $R_4$ in para or meta position.

A heteroaromatic group $R_3$ is a mono- or bicyclic heteroaryl group comprising zero, one, two, three or four ring nitrogen atoms and zero or one oxygen atom and zero or one sulfur atom, with the proviso that at least one ring carbon atom is replaced by a nitrogen, oxygen or sulfur atom, and which has 5 to 12, preferably 5 or 6 ring atoms; and which in addition to carrying a substituent $R_4$ may be unsubstituted or substituted by one or more, especially one, further substituents selected from the group consisting of lower alkyl, such as methyl, lower alkoxy, such as methoxy or ethoxy, halogen, e.g. chlorine, bromine or fluorine, halogenated lower alkyl, such as trifluoromethyl, or hydroxy.

Preferably the mono- or bicyclic heteroaryl group $R_3$ is selected from 2H-pyrrolyl, pyrrolyl, imidazolyl, benzimidazolyl, pyrazolyl, indazolyl, purinyl, pyridyl, pyrazinyl, pyrimidinyl, pyridazinyl, 4H-quinolizinyl, isoquinolyl, quinolyl, phthalazinyl, naphthyridinyl, quinoxalyl, quinazolinyl, quinolinyl, pteridinyl, indolizinyl, 3H-indolyl, indolyl, isoindolyl, oxazolyl, isoxazolyl, thiazolyl, isothiazolyl, triazolyl, tetrazolyl, furazanyl, benzo[d]pyrazolyl, thienyl, and furanyl. More preferably the mono- or bicyclic heteroaryl group is selected from the group consisting of pyrrolyl, imidazolyl, such as 1H-imidazol-1-yl, benzimidazolyl, such as 1-benzimidazolyl, indazolyl, especially 5-indazolyl, pyridyl, e.g. 2-, 3- or 4-pyridyl, pyrimidinyl, especially 2-pyrimidinyl, pyrazinyl, isoquinolinyl, especially 3-isoquinolinyl, quinolinyl, especially 4- or 8-quinolinyl, indolyl, especially 3-indolyl, thiazolyl, triazolyl, tetrazolyl, benzo[d]pyrazolyl, thienyl, and furanyl.

In a particularly preferred embodiment of the invention the heteroaryl group $R_3$ is triazolyl, especially 1-triazolyl, carrying the further substituent $R_4$ in the 4- or 5-position, tetrazolyl, especially 1-tetrazolyl, carrying the further substituent $R_4$ in the 4- or 5-position, or 2-tetrazolyl carrying the further substituent $R_4$ in 5-position, isoxazolyl, especially 3-isoxazolyl carrying the further substituent $R_4$ in 5-position, or 5-isoxazolyl, carrying the further substituent $R_4$ in 3-position, or thienyl, especially 2-thienyl, carrying the further substituent $R_4$ in 3-, 4- or 5-position, preferably 4-position, or 3-thienyl, carrying the further substituent $R_4$ in 4-position.

Most preferred is the heteroaryl group $R_3$ as triazolyl, carrying the substituent $R_4$ in 4- or 5-position, and also $R_3$ as 2-thienyl carrying the substituent $R_4$ in 4- or 5-position.

An optionally substituted unsaturated alkyl group $R_3$ is 1-alkenyl carrying the further substituent $R_4$ in 1- or 2-position, preferably in 2-position, or 1-alkynyl. Substituents considered in 1-alkenyl are e.g. lower alkyl, e.g. methyl, lower alkoxy, e.g. methoxy, lower acyloxy, e.g. acetoxy, or halogenyl, e.g. chloro. In a particularly preferred embodiment of the invention $R_3$ is 1-alkynyl.

An optionally substituted unsaturated cycloalkyl group is a cycloalkyl group with 3 to 7 carbon atoms unsaturated in 1-position, e.g. 1-cyclopentyl or 1-cyclohexyl, carrying the further substituent $R_4$ in any position. Substituents considered are e.g. lower alkyl, e.g. methyl, lower alkoxy, e.g. methoxy, lower acyloxy, e.g. acetoxy, or halogenyl, e.g. chloro.

An optionally substituted unsaturated heterocyclyl group has 3 to 12 atoms, 1 to 5 heteroatoms selected from nitrogen, oxygen and sulfur, and a double bond in the position connecting the heterocyclyl group to methylene $CH_2$. Substituents considered are e.g. lower alkyl, e.g. methyl, lower alkoxy, e.g. methoxy, lower acyloxy, e.g. acetoxy, or halogenyl, e.g. chloro.

In particular, an optionally substituted unsaturated heterocyclyl group is a partially saturated heteroaromatic group as defined hereinbefore for a heteroaromatic group $R_3$. An example of such a heterocyclyl group is isoxazolidinyl, especially 3-isoxazolidinyl carrying the further substituent in 5-position, or 5-isoxazolidinyl, carrying the further substituent in 3-position.

A linker group $R_4$ is preferably a flexible linker connecting a label L or a plurality of same or different labels L to the substrate. Linker units are chosen in the context of the envisioned application, i.e. in the transfer of the substrate to a fusion protein comprising AGT. They also increase the solubility of the substrate in the appropriate solvent. The linkers used are chemically stable under the conditions of the actual application. The linker does not interfere with the reaction with AGT nor with the detection of the label L, but may be constructed such as to be cleaved at some point in time after the reaction of the compound of formula 1 with the fusion protein comprising AGT.

A linker $R_4$ is a straight or branched chain alkylene group with 1 to 300 carbon atoms, wherein optionally (a) one or more carbon atoms are replaced by oxygen, in particular wherein every third carbon atom is replaced by oxygen, e.g. a poylethyleneoxy group with 1 to 100 ethyleneoxy units;

(b) one or more carbon atoms are replaced by nitrogen carrying a hydrogen atom, and the adjacent carbon atoms are substituted by oxo, representing an amide function —NH—CO—;

(c) one or more carbon atoms are replaced by oxygen, and the adjacent carbon atoms are substituted by oxo, representing an ester function —O—CO—;

(d) the bond between two adjacent carbon atoms is a double or a triple bond, representing a function —CH=CH— or —C≡C—;

(e) one or more carbon atoms are replaced by a phenylene, a saturated or unsaturated cycloalkylene, a saturated or unsaturated bicycloalkylene, a bridging heteroaromatic or a bridging saturated or unsaturated heterocyclyl group;

(f) two adjacent carbon atoms are replaced by a disulfide linkage —S—S—;

or a combination of two or more, especially two or three, alkylene and/or modified alkylene groups as defined under (a) to (f) hereinbefore, optionally containing substituents.

Substituents considered are e.g. lower alkyl, e.g. methyl, lower alkoxy, e.g. methoxy, lower acyloxy, e.g. acetoxy, or halogenyl, e.g. chloro.

Further substituents considered are e.g. those obtained when an α-amino acid, in particular a naturally occurring α-amino acid, is incorporated in the linker $R_4$ wherein carbon atoms are replaced by amide functions —NH—CO— as defined under (b). In such a linker, part of the carbon chain of the alkylene group $R_4$ is replaced by a group —(NH—CHR—CO)$_n$— wherein n is between 1 and 100 and R represents a varying residue of an α-amino acid.

A further substituent is one which leads to a photocleavable linker $R_4$, e.g. an o-nitrophenyl group. In particular this substituent o-nitrophenyl is located at a carbon atom adjacent to an amide bond, e.g. in a group —NH—CO—$CH_2$—CH(o-nitrophenyl)-NH—CO—, or as a substituent in a polyethylene glycol chain, e.g. in a group —O—$CH_2$—CH(o-nitrophenyl)-O—. Other photo-cleavable linkers considered are, e.g. phenacyl, alkoxybenzoin, benzylthioether and pivaloyl glycol derivatives.

A phenylene group replacing carbon atoms as defined under (e) hereinbefore is e.g. 1,2-, 1,3-, or preferably 1,4-phenylene. In a particular embodiment, the phenylene group is further substituted by a nitro group, and, combined with other replacements as mentioned above under (a), (b), (c), (d), and (f), represents a photocleavable group, and is e.g. 4-nitro-1,3-phenylene, such as in —CO—NH—$CH_2$-4-nitro-1,3-phenylene-CH($CH_3$)—O—CO—, or 2-methoxy-5-nitro-1,4-phenylene, such as in —$CH_2$—O-2-methoxy-5-nitro-1,4-phenylene-CH($CH_3$)—O—. Other particular embodiments representing photocleavable linkers are e.g. -1,4-phenylene-CO—$CH_2$—O—CO—$CH_2$— (a phenacyl group), -1,4-phenylene-CH(OR)—CO—1,4-phenylene- (an alkoxybenzoin), or -3,5-dimethoxy-1,4-phenylene-$CH_2$—O— (a dimethoxybenzyl moiety). A saturated or unsaturated cycloalkylene group replacing carbon atoms as defined under (e) hereinbefore is derived from cycloalkyl with 3 to 7 carbon atoms, preferably from cyclopentyl or cyclohexyl, and is e.g. 1,2- or 1,3-cyclopentylene, 1,2-, 1,3-, or preferably 1,4-cyclohexylene, or also 1,4-cyclohexylene being unsaturated e.g. in 1- or in 2-position. A saturated or unsaturated bicycloalkylene group replacing carbon atoms as defined under (e) hereinbefore is derived from bicycloalkyl with 7 or 8 carbon atoms, and is e.g. bicyclo[2.2.1]heptylene or bicyclo[2.2.2]octylene, preferably 1,4-bicyclo[2.2.1]heptylene optionally unsaturated in 2-position or doubly unsaturated in 2- and 5-position, and 1,4-bicyclo[2.2.2]octylene optionally unsaturated in 2-position or doubly unsaturated in 2- and 5-position. A bridging heteroaromatic group replacing carbon atoms as defined under (e) hereinbefore is e.g. triazolidene, preferably 1,4-triazolidene, or isoxazolidene, preferably 3,5-isoxazolidene. A bridging saturated or unsaturated heterocyclyl group replacing carbon atoms as defined under (e) hereinbefore is e.g. derived from an unsaturated heterocyclyl group as defined under $R_3$ above, e.g. isoxazolidinene, preferably 3,5-isoxazolidinene, or a fully saturated heterocyclyl group with 3 to 12 atoms, 1 to 3 of which are heteroatoms selected from nitrogen, oxygen and sulfur, e.g. pyrrolidinediyl, piperidinediyl, tetrahydrofuranediyl, dioxanediyl, morpholinediyl or tetrahydrothiophenediyl, preferably 2,5-tetrahydrofuranediyl or 2,5-dioxanediyl. A particular heterocyclyl group considered is a saccharide moiety, e.g. an α- or β-furanosyl or α- or β-pyranosyl moiety.

Cyclic substructures in a linker $R_4$ reduce the molecular flexibility as measured by the number of rotatable bonds within $R_4$, which leads to a better membrane permeation rate, important for all in vivo labelling applications.

A linker $R_4$ is preferably a straight chain alkylene group with 1 to 25 carbon atoms or a straight chain polyethylene glycol group with 4 to 100 ethyleneoxy units, optionally attached to the group $R_3$ by a —CH=CH— or —C≡C— group. Further preferred is a straight chain alkylene group with 1 to 25 carbon atoms wherein carbon atoms are optionally replaced by an amide function —NH—CO—, and carrying a photocleavable subunit, e.g. o-nitrophenyl. Further preferred are branched linkers comprising a polyethylene glycol group of 3 to 6 ethylene glycol units and alkylene groups wherein carbon atoms are replaced by amide bonds, and further carrying substituted amino and hydroxy functions. Other preferred branched linkers have dendritic (tree-like) structures wherein amine, carboxamide and/or ether functions replace carbon atoms of an alkylene group.

A particularly preferred linker $R_4$ is a straight chain alkylene group of 10 to 40 carbon atoms wherein 3 to 12 carbon atoms are replaced by oxygen, one or two carbon atoms are replaced by one or two 1,4-triazolidene units, respectively, and optionally one carbon atom is replaced by a 1,4-phenylene unit.

Another particularly preferred linker $R_4$ is a straight chain alkylene group of 10 to 40 carbon atoms optionally substituted by oxo wherein 3 to 12 carbon atoms are replaced by oxygen and one or two carbon atoms are replaced by nitrogen.

Another particularly preferred linker $R_4$ is a straight chain alkylene group of 6 to 40 carbon atoms wherein 2 to 12 carbon atoms are replaced by oxygen and one or two bonds between two adjacent carbon atoms is a double bond representing a function —CH=CH—.

A linker $R_4$ may carry one or more same or different labels, e.g. 1 to 100 same or different labels, in particular 1 to 5, preferably one, two or three, in particular one or two same or different labels.

The label part L of the substrate can be chosen by those skilled in the art dependent on the application for which the fusion protein is intended. Labels may be e.g. such that the labelled fusion protein is easily detected or separated from its environment. Other labels considered are those which are capable of sensing and inducing changes in the environment of the labelled fusion protein and/or labels which aid in manipulating the fusion protein by the physical and/or chemical properties specifically introduced by the label to the fusion protein.

Examples of labels L include a spectroscopic probe such as a fluorophore, a chromophore, a magnetic probe or a contrast reagent; a radioactively labelled molecule; a molecule which is one part of a specific binding pair which is capable of specifically binding to a partner; a molecule that is suspected to interact with other biomolecules; a library of molecules that are suspected to interact with other biomolecules; a molecule which is capable of crosslinking to other molecules; a molecule which is capable of generating hydroxyl radicals upon exposure to $H_2O_2$ and ascorbate, such as a tethered metal-chelate; a molecule which is capable of generating reactive radicals upon irradiation with light, such as malachite green; a molecule covalently attached to a solid support, where the support may be a glass slide, a microtiter plate or any polymer known to those proficient in the art; a nucleic acid or a derivative thereof capable of undergoing base-pairing with its complementary strand; a lipid or other hydrophobic molecule with membrane-inserting properties; a biomolecule with desirable enzymatic, chemical or physical properties; or a molecule possessing a combination of any of the properties listed above. Preferred are labels L as mentioned hereinbefore with the exception of a radioactively labelled molecule. Most preferred as labels L are spectroscopic probes, and molecules which are one part of a specific binding pair which is capable of specifically binding to a partner, so-called affinity labels.

When the label L is a fluorophore, a chromophore, a magnetic label, a radioactive label or the like, detection is by standard means adapted to the label and whether the method is used in vitro or in vivo. The method can be compared to the applications of the green fluorescent protein (GFP) which is genetically fused to a protein of interest and allows protein investigation in the living cell. Particular examples of labels L are also boron compounds displaying non-linear optical properties, or a member of a FRET pair which changes its spectroscopic properties on reaction of the labelled substrate with the AGT fusion protein.

Depending on the properties of the label L, the fusion protein comprising protein of interest and AGT may be bound to a solid support. The label of the substrate reacting with the fusion protein comprising AGT may already be attached to a solid support when entering into reaction with AGT, or may subsequently, i.e. after transfer to AGT, be used to attach the AGT fusion protein to a solid support. The label may be one member of a specific binding pair, the other member of which is attached or attachable to the solid support, either covalently or by any other means. A specific binding pair considered is e.g. biotin and avidin or streptavidin. Either member of the binding pair may be the label L of the substrate, the other being attached to the solid support. Further examples of labels allowing convenient binding to a solid support are e.g. maltose binding protein, glycoproteins, FLAG tags, or reactive substituents allowing chemoselective reaction between such substituent with a complementary functional group on the surface of the solid support. Examples of such pairs of reactive substituents and complementary functional group are e.g. amine and activated carboxy group forming an amide, azide and a propiolic acid derivative undergoing a 1,3-dipolar cycloaddition reaction, amine and another amine functional group reacting with an added bifunctional linker reagent of the type of activated bis-dicarboxylic acid derivative giving rise to two amide bonds, or other combinations known in the art.

Examples of a convenient solid support are e.g. glass surfaces such as glass slides, microtiter plates, and suitable sensor elements, in particular functionalized polymers (e.g. in the form of beads), chemically modified oxidic surfaces, e.g. silicon dioxide, tantalum pentoxide or titanium dioxide, or also chemically modified metal surfaces, e.g. noble metal surfaces such as gold or silver surfaces. Irreversibly attaching and/or spotting AGT substrates may then be used to attach AGT fusion proteins in a spatially resolved manner, particularly through spotting, on the solid support representing protein microarrays, DNA microarrays or arrays of small molecules.

When the label L is capable of generating reactive radicals, such as hydroxyl radicals, upon exposure to an external stimulus, the generated radicals can then inactivate the AGT fusion proteins as well as those proteins that are in close proximity of the AGT fusion protein, allowing to study the role of these proteins. Examples of such labels are tethered metal-chelate complexes that produce hydroxyl radicals upon exposure to $H_2O_2$ and ascorbate, and chromophores such as malachite green that produce hydroxyl radicals upon laser irradiation. The use of chromophores and lasers to generate hydroxyl radicals is also known in the art as chromophore assisted laser induced inactivation (CALI). In the present invention, labelling AGT fusion proteins with chromophores such as malachite green and subsequent laser irradiation inactivates the AGT fusion protein as well as those proteins that interact with the AGT fusion protein in a time-controlled and spatially-resolved manner. This method can be applied both in vivo or in vitro. Furthermore, proteins which are in close proximity of the AGT fusion protein can be identified as such by either detecting fragments of that protein by a specific antibody, by the disappearance of those proteins on a high-resolution 2D-electrophoresis gels or by identification of the cleaved protein fragments via separation and sequencing techniques such as mass spectrometry or protein sequencing by N-terminal degradation.

When the label L is a molecule that can cross-link to other proteins, e.g. a molecule containing functional groups such as maleimides, active esters or azides and others known to those proficient in the art, contacting such labelled AGT substrates with AGT fusion proteins that interact with other proteins (in vivo or in vitro) leads to the covalent cross-linking of the AGT fusion protein with its interacting protein via the label. This allows the identification of the protein interacting with the AGT fusion protein. Labels L for photo cross-linking are e.g. benzophenones. In a special aspect of cross-linking the label L is a molecule which is itself an AGT substrate leading to dimerization of the AGT fusion protein. The chemical structure of such dimers may be either symmetrical (homodimers) or unsymmetrical (heterodimers).

Other labels L considered are for example fullerenes, boranes for neutron capture treatment, nucleotides or oligonucleotides, e.g. for self-addressing chips, peptide nucleic acids, and metal chelates, e.g. platinum chelates that bind specifically to DNA.

A particular biomolecule with desirable enzymatic, chemical or physical properties is methotrexate. Methotrexate is a tight-binding inhibitor of the enzyme dihydrofolate reductase (DHFR). Compounds of formula 1 wherein L is methotrexate belong to the well known class of so-called "chemical inducers of dimerization" (CIDs). Using fusion proteins of hAGT with the DNA-binding domain LexA, and adding DHFR with the transcriptional activation domain B42 to the in vivo labelling of the hAGT fusion protein with a compound of formula 1 wherein L is methotrexate induces the coupling ("dimerization") of the hAGT-LexA fusion protein and DHFR-B42 fusion protein, leading to spatial proximity of LexA and B42 and subsequent stimulation of transcription as shown in FIG. 4.

If the substrate carries two or more labels, these labels may be identical or different. Particular preferred combinations are two different affinity labels, or one affinity label and one chromophore label, in particular one affinity label and one fluorophore label.

The present invention further provides a method to label AGT fusion proteins both in vivo as well as in vitro. The term in vivo labelling of a AGT fusion protein includes labelling in all compartments of a cell as well as of AGT fusion proteins pointing to the extracellular space. If the labelling of the AGT fusion protein is done in vivo and the protein fused to the AGT is a membrane protein, more specifically a plasma membrane protein, the AGT part of the fusion protein can be attached to either side of the membrane, e.g. attached to the cytoplasmic or the extracellular side of the plasma membrane.

If the labelling is done in vitro, the labelling of the fusion protein can be either performed in cell extracts or with purified or enriched forms of the AGT fusion protein.

If the labelling is done in vivo or in cell extracts, the labelling of the endogenous AGT of the host is advantageously taken into account. If the endogenous AGT of the host does not accept $O^6$-alkylguanine derivatives or related compounds as a substrate, the labelling of the fusion protein is specific. In mammalian cells, e.g. in human, murine, or rat cells, labelling of endogenous AGT is possible. In those experiments where the simultaneous labelling of the endogenous AGT as well as of the AGT fusion protein poses a problem, known AGT-deficient cell lines can be used.

In a particular aspect, the present invention provides a method of determining the interaction of a candidate compound or library of candidate compounds and a target protein or library of target proteins. Examples of candidate compounds and target proteins include ligands and proteins, drugs and targets of the drug, or small molecules and proteins. In this particular method of the invention, the protein of interest fused to the AGT comprises a DNA binding domain of a transcription factor or an activation domain of a transcription factor. The putative protein target of the substances or library of proteins is linked to either of the DNA binding domain or the activation domain of the transcription factor in a way a functional transcription factor can be formed, and the label L of the AGT substrate according to the invention is a candidate compound or library of candidate compounds suspected of interacting with the target substance or substances. The candidate compound or library of candidate compounds being part of the substrate is then transferred to the AGT fusion protein. On transfer the AGT fusion protein(s) comprising the target substance(s) now are labelled with the candidate compound(s). The interaction of a candidate compound joined to the AGT fusion protein with the target protein fused to either the DNA binding domain or the activation domain leads to the formation of a functional transcription factor. The activated transcription factor can then drive the expression of a reporter which, if the method is carried out in cells, can be detected if the expression of the reporter confers a selective advantage on the cells.

In particular embodiments, the method may involve one or more further steps such as detecting, isolating, identifying or characterising the candidate compound(s) or target substance(s).

In a specific example the label L is a drug or a biological active small molecule that binds to a yet unidentified protein Y. A cDNA library of the organism which is expected to express the unknown target protein Y is fused to the activation domain of a transcription factor, and the AGT is fused to the DNA binding domain of a transcription factor. Adding the AGT substrate of the invention comprising such a label L leads to the formation of a functional transcription factor and gene expression only in the case where this molecule binds to its target protein Y present in the cDNA library and fused to the activation domain. If gene expression is coupled to a selective advantage, the corresponding host carrying the plasmid with the gene coding for the target protein Y of the drug or bioactive molecule can be identified.

In a further specific example the label L is a library of chemical molecules. The library is expected to contain yet unidentified compounds that bind to a known drug target protein Y under in vivo conditions. The target protein Y is fused to the activation domain of a transcription factor and the AGT is fused to the DNA binding domain of a transcription factor. Adding the substrate carrying the library of chemical compounds leads to the formation of a functional transcription factor and gene expression only in the case where the label (i.e. a compound in the chemical library) binds to its target protein Y fused to the activation domain. If gene expression is coupled to a selective advantage, those molecules of the library leading to the growth of the host can be identified.

In the case where L is a bond connecting $R_4$ to $R_1$ forming a cyclic substrate, a preferred compound is the cyclic substrate wherein the bond from $R_4$ to $R_1$ is a bond connecting the linker $R_4$ to an amino group $R_6$ as defined under formula 2. In such a preferred cyclic substrate, $R_2$ is preferably an oligonucleotide, i.e. a β-D-2'-deoxyribosyl being incorporated into a single stranded oligodeoxyribonucleotide having a length of 2 to 99 nucleotides as detailed above. This oligonucleotide may be further chemically modified so that it can be detected and functions therefore as a label. The chemical modification of substituents might be of the same nature as mentioned above for the label L.

In the case where L is a further group —$R_3$—$CH_2$—X—$R_1$-$R_2$, the substrate is a dimeric compound leading to a dimerised fusion protein on reaction with a fusion protein comprising AGT. In the subunit L as a residue —$R_3$—$CH_2$—X—$R_1$-$R_2$, the meaning of $R_1$, $R_2$, $R_3$ and X may be identical with the corresponding meaning in the other group $R_2$-$R_1$—X—$CH_2$—$R_3$—, representing a homodimer, or different, representing a heterodimer.

Most preferred are compounds of formula 1 shown in the Schemes and described in the Examples.

Methods of manufacture of novel substrates and intermediates are also an object of this invention. These methods are generally known in the art, are chosen as to best produce the preferred substrates of the invention, and are exemplified hereinbelow. In particular, the invention concerns a method wherein a compound of the formula $R_2$-$R_1$—Y, wherein Y is a reactive leaving group, e.g. an ammonium salt, is treated with a compound of formula HX—$CH_2$—$R_3$-$R_4$-L or a precursor thereof, and the resulting compound is further manipulated, e.g. by elaboration of the linker $R_4$ and/or the introduction of a label L. Alternatively, a compound of the formula $R_2$-$R_1$—XH is alkylated with a compound of the formula Y—$CH_2$—$R_3$-$R_4$-L, wherein Y is a leaving group, e.g. halogen, or a precursor thereof, and the resulting compound is further manipulated, e.g. by elaboration of the residue $R_3$ and/or the linker $R_4$, and/or the introduction of a label L.

In particular, the invention concerns methods of manufacture of novel substrates carrying more than one label. Thus the synthesis proceeds through a core compound of the formula $R_2$-$R_1$—X—$CH_2$—$R_3$-$R_4$ wherein $R_4$ is a polyfunctional residue having two or more reactive nucleophilic or electrophilic groups. Examples of such groups include hydroxy, amino, sulfhydryl, halo or carboxy. Further examples of reactive groups are Michael acceptors such as maleimides or vinylsulfones. In addition, functional groups which can take part in cycloaddition reactions are also included, such as dienes or dienophiles, azides, nitrones, nitriloxides, acetylenes, and alkenes.

The specific functional groups, which can be placed on the residue $R_4$, in particular at the outer sphere of a branched residue, for the attachment of suitable labels are limited only by the requirement that they are not supposed to be reactive with each other or with any compound or reagent used to build the substrate of the invention. Thus their selection will depend upon the specific reagents chosen to build the desired substrates. Examples of functional groups which can be provided on the outer sphere of a branched residue $R_4$ include fluoro, chloro, bromo, cyano, nitro, amino, alkylcarbonylamino, arylcarbonylamino, alkoxycarbonylamino, aryloxycarbonylamino, carboxy, carbamoyl, alkoxycarbonyl, aryloxycarbonyl, carbaldehyde, hydroxy, alkoxy, aryloxy, alkylcarbonyloxy, arylcarbonyloxy, a carbon-carbon double bond, a carbon-carbon triple bond, and the like. Most preferable examples include amino, hydroxy, cyano (a latent carboxy function), carbamoyl, carbaldehyde, or a carbon-carbon double bond.

In particular, the preferred synthesis of a branched residue $R_4$ carrying a plurality of labels L makes use of orthogonally protected functional groups. Such a choice of protective groups allows for a separate deprotection so that each released functionality in turn can be further chemically manipulated either to attach a label to it or for the introduction of further extension of linker $R_4$. Appropriate protecting groups for the envisioned functionalities can be chosen by those skilled in the art, and are e.g. summarized in T. W. Greene and P. G. M. Wuts in "Protective Groups in Organic Synthesis", John Wiley & Sons, New York 1991.

Preferred intermediates according to the invention are compounds of formula 1 wherein $R_1$-$R_2$ is a radical of formula 2 wherein $R_2$ is hydrogen, $R_5$ is hydrogen and $R_6$ is unsubstituted amino; and X is oxygen; $R_3$ is triazolyl, tetrazolyl, isoxazolyl, thienyl, isoxazolidinyl or alkynyl; $R_4$ is a linker; and L is amino or azido, in particular amino.

Other preferred intermediates according to the invention are compounds of formula 1 wherein $R_1$-$R_2$ is a radical of formula 2 wherein $R_2$ is hydrogen, $R_5$ is hydrogen and $R_6$ is unsubstituted amino; and X is oxygen; $R_3$ is 1,4-phenylene; $R_4$ is a straight chain alkylene group of 10 to 40 carbon atoms optionally substituted by oxo wherein up to 12 carbon atoms are replaced by oxygen and zero, one or two carbon atoms are replaced by nitrogen; and L is amino or azido, in particular amino.

Most preferred are the intermediates described in the Schemes and Examples.

The synthesis of an intermediate useful in the synthesis of compounds of formula 1 wherein $R_3$ is a tetrazolyl group, an isoxazolyl group or an isoxazolidinyl group is summarized in Scheme 1 and 2.

The azido compound 7 is prepared from commercially available tetraethylene glycol 5 by mesylation (methanesulfonyl chloride, triethylamine) followed by reaction with sodium azide in ethanol. 7 is again mesylated and subjected to a Gabriel amine synthesis to give azido-amine 9 (Carolay et al., J. Org. Chem. 56: 4326-4329, 1991). The Cu(I)-catalyzed 1,3-dipolar cycloaddition between azide 9 and the acetylene derivative 10 (Griffin et al., J. Med. Chem. 43: 4071-4083, 2000) yields the 1,4-substituted triazole 11. Alternatively the azide 9 and the cyano derivative 12 react under Lewis acid catalysis (ZnBr$_2$) to form tetrazole 13 (Scheme 1).

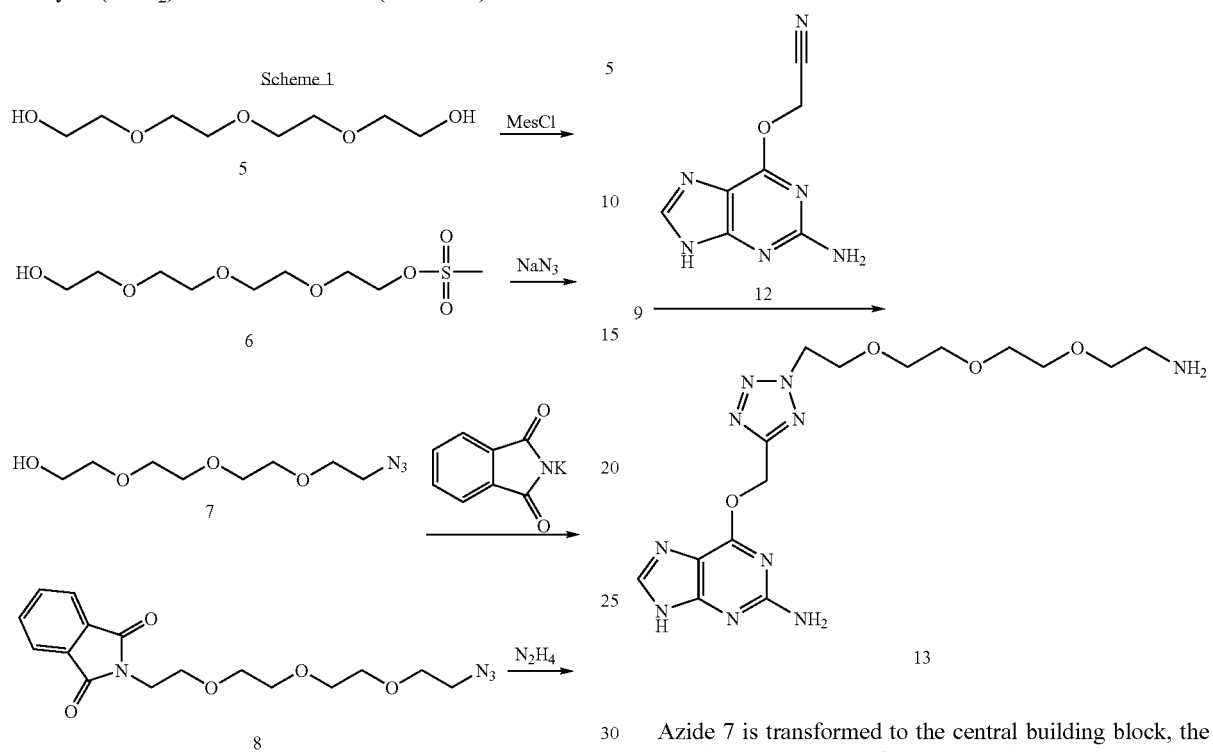

Azide 7 is transformed to the central building block, the aldehyde 14, by means of a Swerns oxidation (oxalyl chloride, DMSO, triethylamine). The reaction of 14 with a hydroxylamine derivative yields the nitrone 17, which upon reaction with the acetylene derivative 10 forms the class of isoxazolidines 18. From aldehyde 14, the oxime 15 is formed as an equimolar mixture of isomers. The corresponding nitrile-oxide is formed in situ by oxidation with sodium hypochlorite followed by reaction with 10 to yield the isoxazole 16 (Scheme 2).

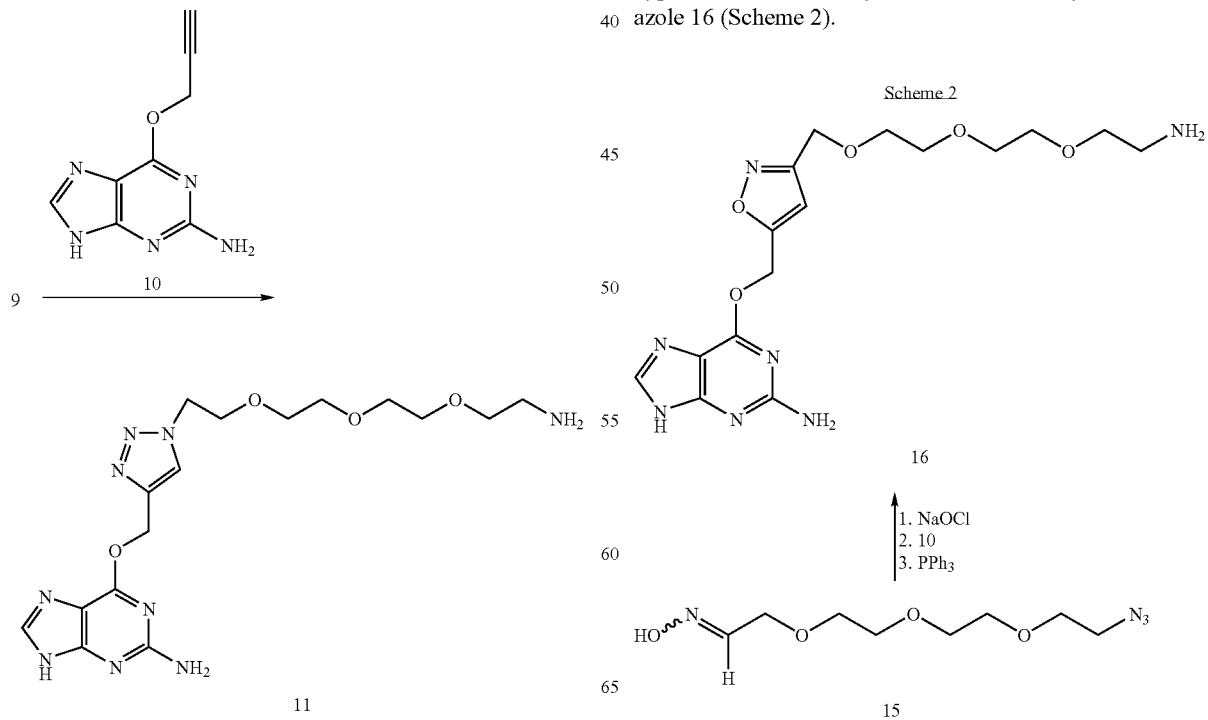

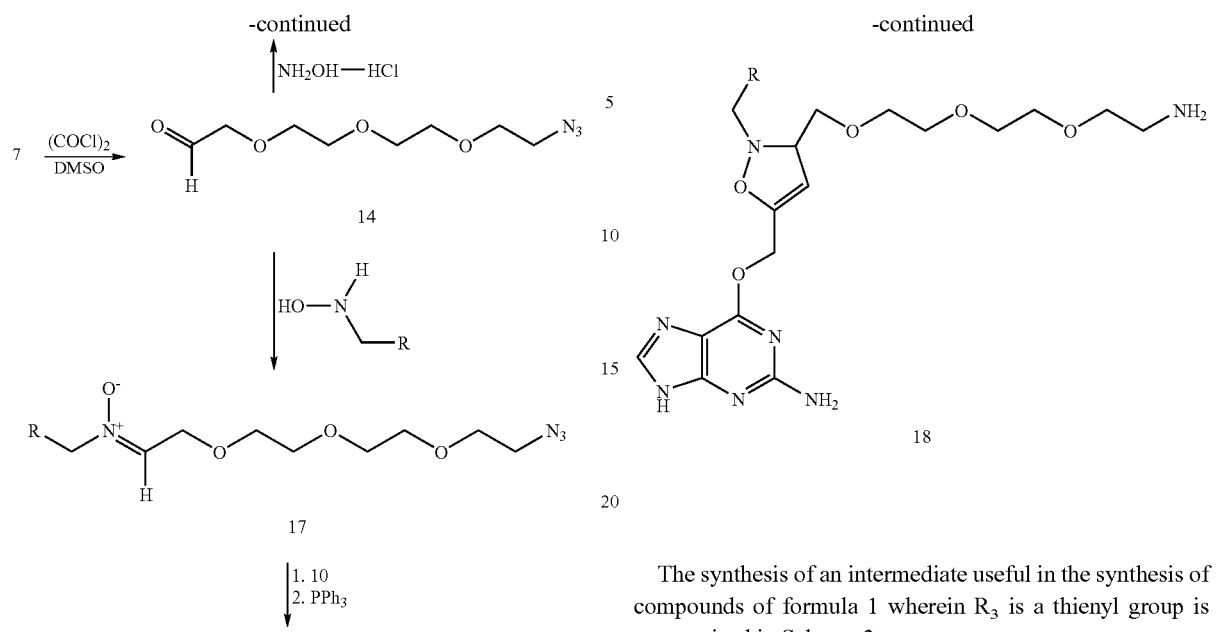
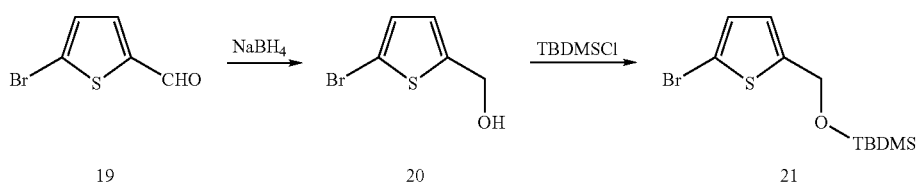
The synthesis of an intermediate useful in the synthesis of compounds of formula 1 wherein $R_3$ is a thienyl group is summarized in Scheme 3.
Scheme 3
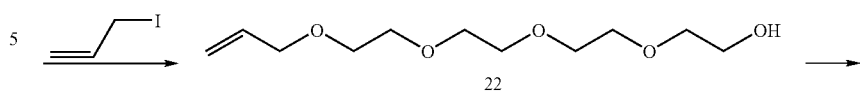
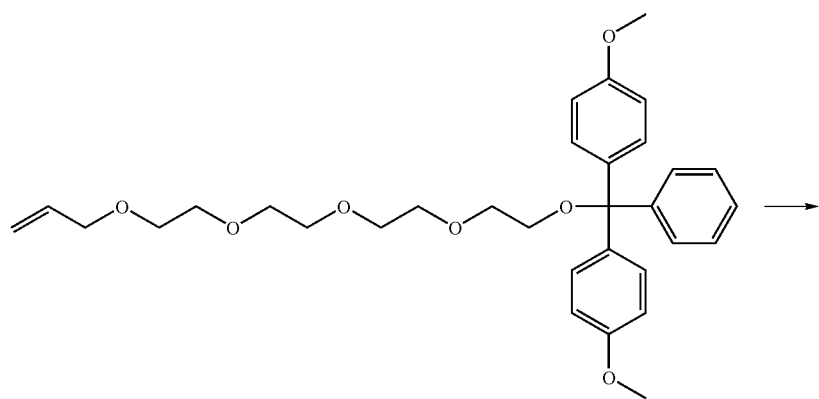

-continued
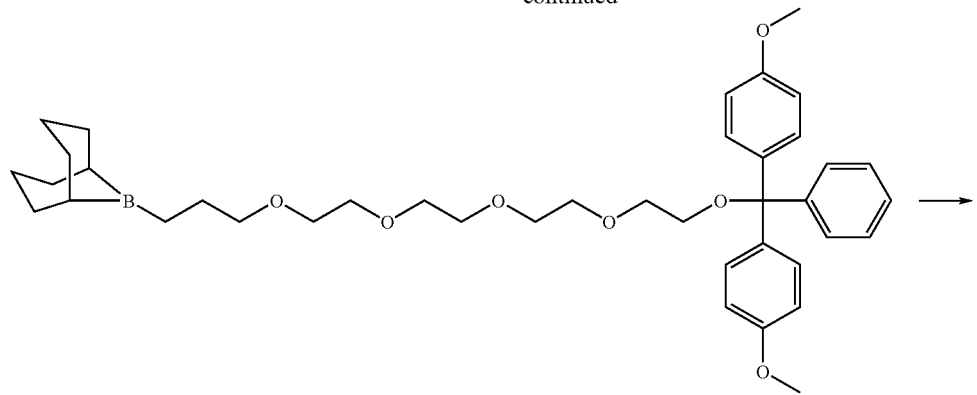
24
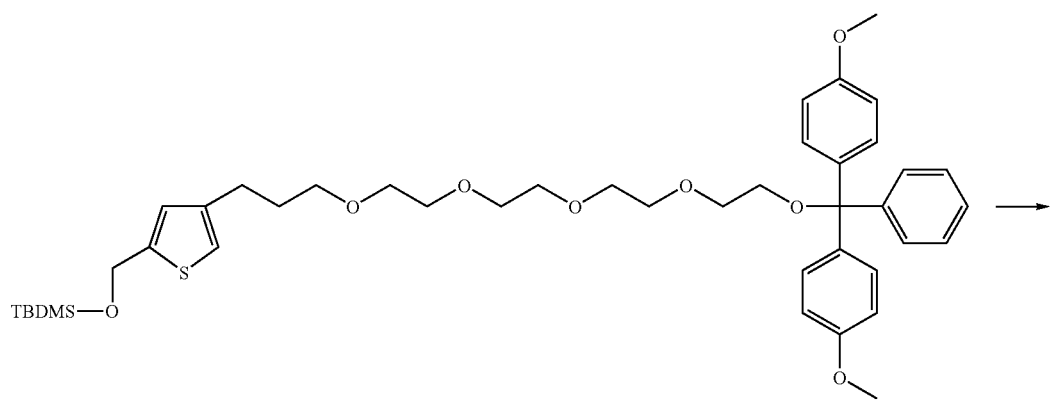
25
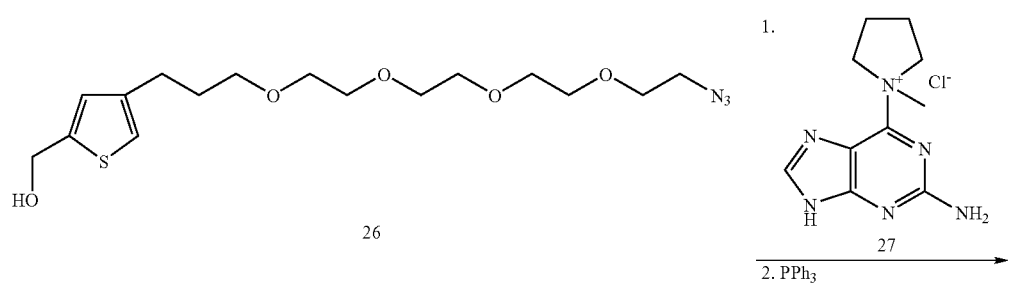
26
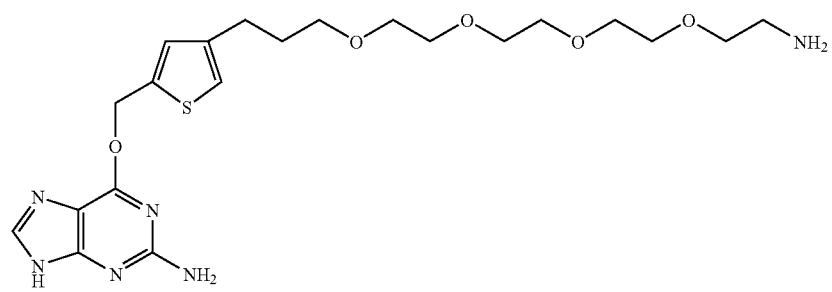
28

The commercially available tetraethylene glycol 5 is monofunctionalized through the reaction with one equivalent of allyl iodide under strongly basic conditions to yield 22 which is further dimethoxytrityl (DMT)-protected to 23. This intermediate allows the palladium catalyzed Suzuki coupling with thiophene derivative 21 to the fully protected compound 25.

Monodeprotection of the DMT-group and subsequent mesylation (methanesulfonyl chloride, triethylamine) followed by the reaction with sodium azide in ethanol gives the protected azide which is deprotected with HF/pyridine to 26. Coupling of the free hydroxy group with the activated guanine-cation 27 leads to an azido-intermediate which serves as a precursor for different functionalization strategies. Finally reduction of the azide to amine 28 allows the introduction of the label unit L or the coupling to different surfaces.

The synthesis of an intermediate useful in the synthesis of compounds of formula 1 wherein $R_3$ is a phenylene group is summarized in Scheme 4.

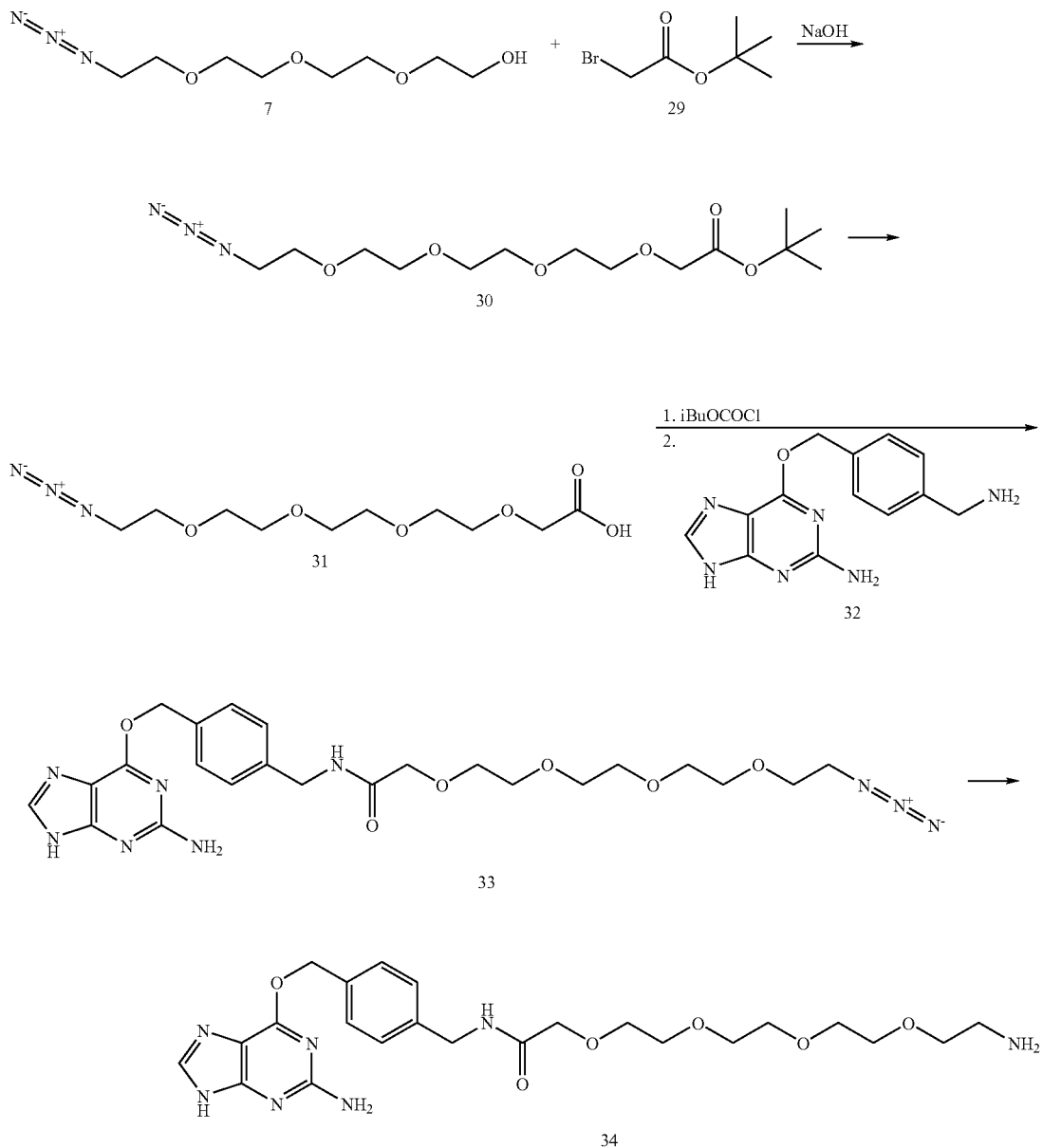

A compound of formula 1 wherein $R_1$ is guanine, $R_2$ is hydrogen, $R_3$ is 1,4-phenylene, $R_4$ is a unit composed of two triazolyl-4-methoxy units and a tetraethyleneoxy unit and L is —$R_3$—$CH_2$—X—$R_1$-$R_2$ is prepared as shown in Scheme 5:

Scheme 5
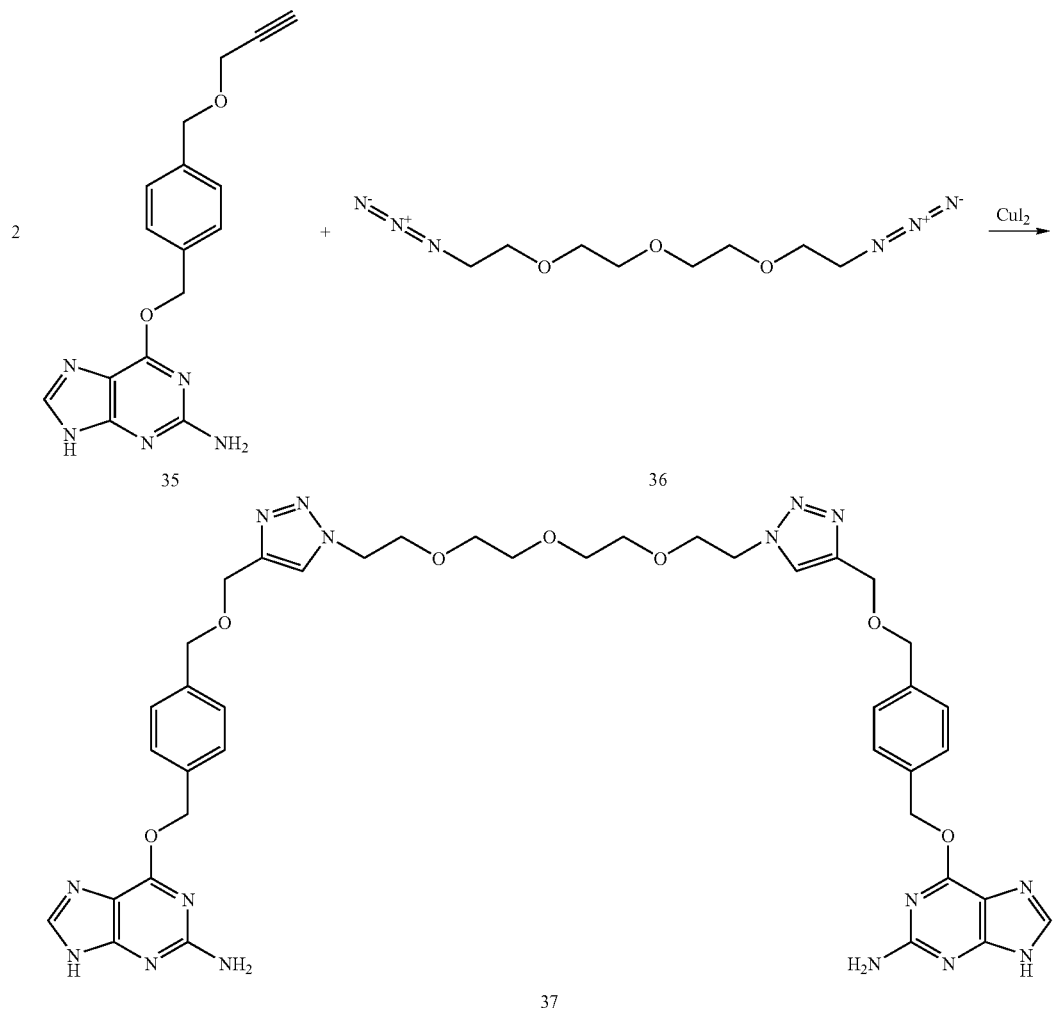
Compounds of formula 1 wherein $R_1$ is guanine, $R_2$ is hydrogen, $R_3$ is 1,4-phenylene, $R_4$ is a tetraethyleneoxy unit further comprising a triazolyl-4-methoxy group and L is $-R_3-CH_2-X-R_1-R_2$ is prepared as shown in Scheme 6, 7 and 8:
Scheme 6
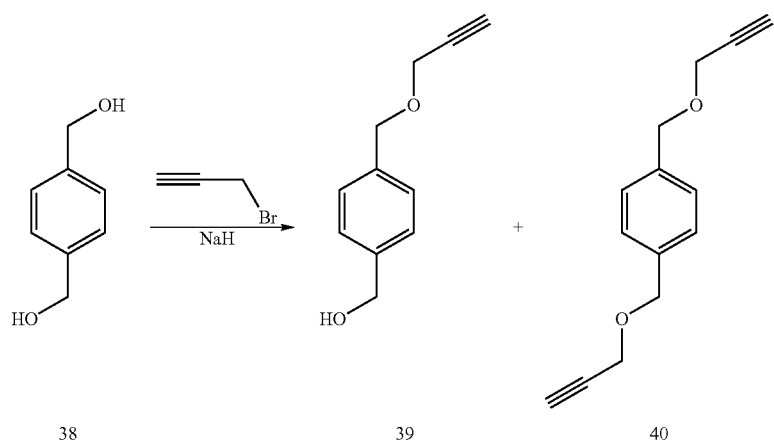

-continued
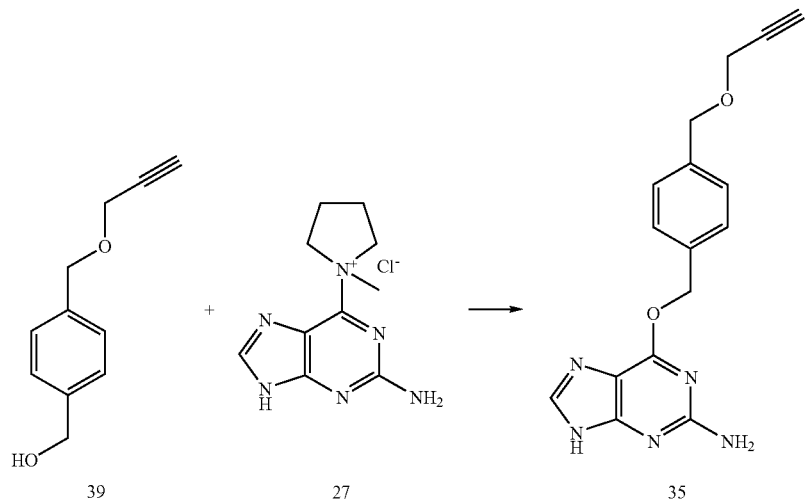
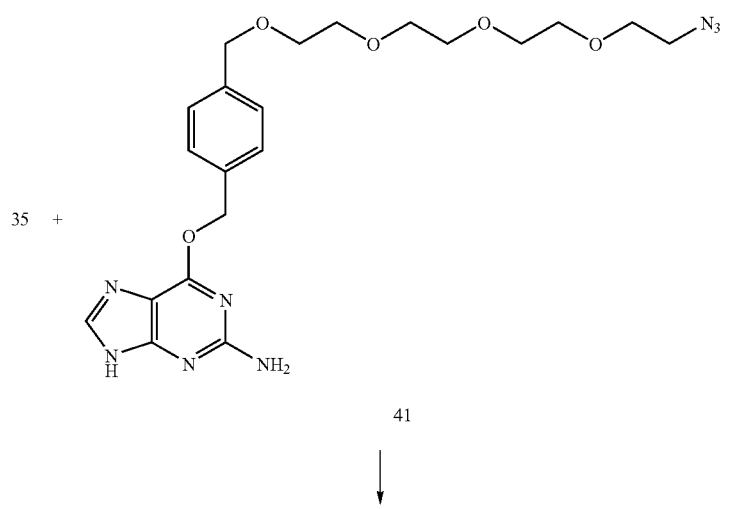
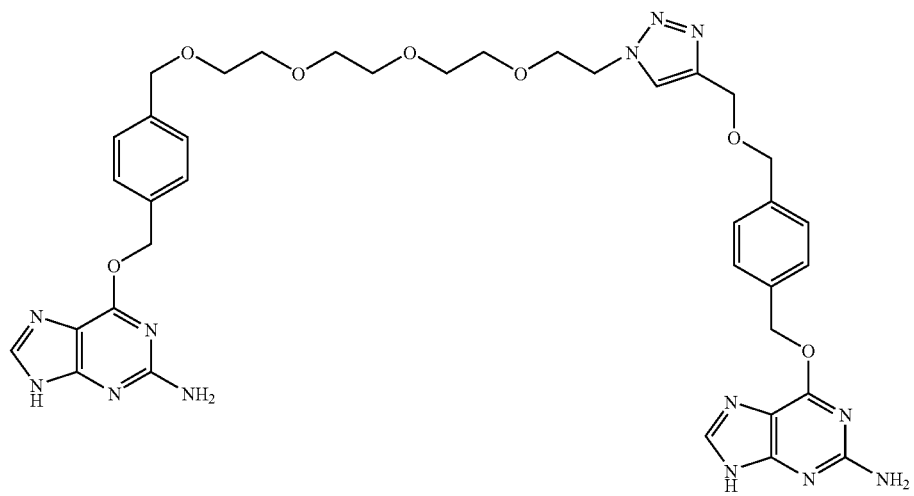

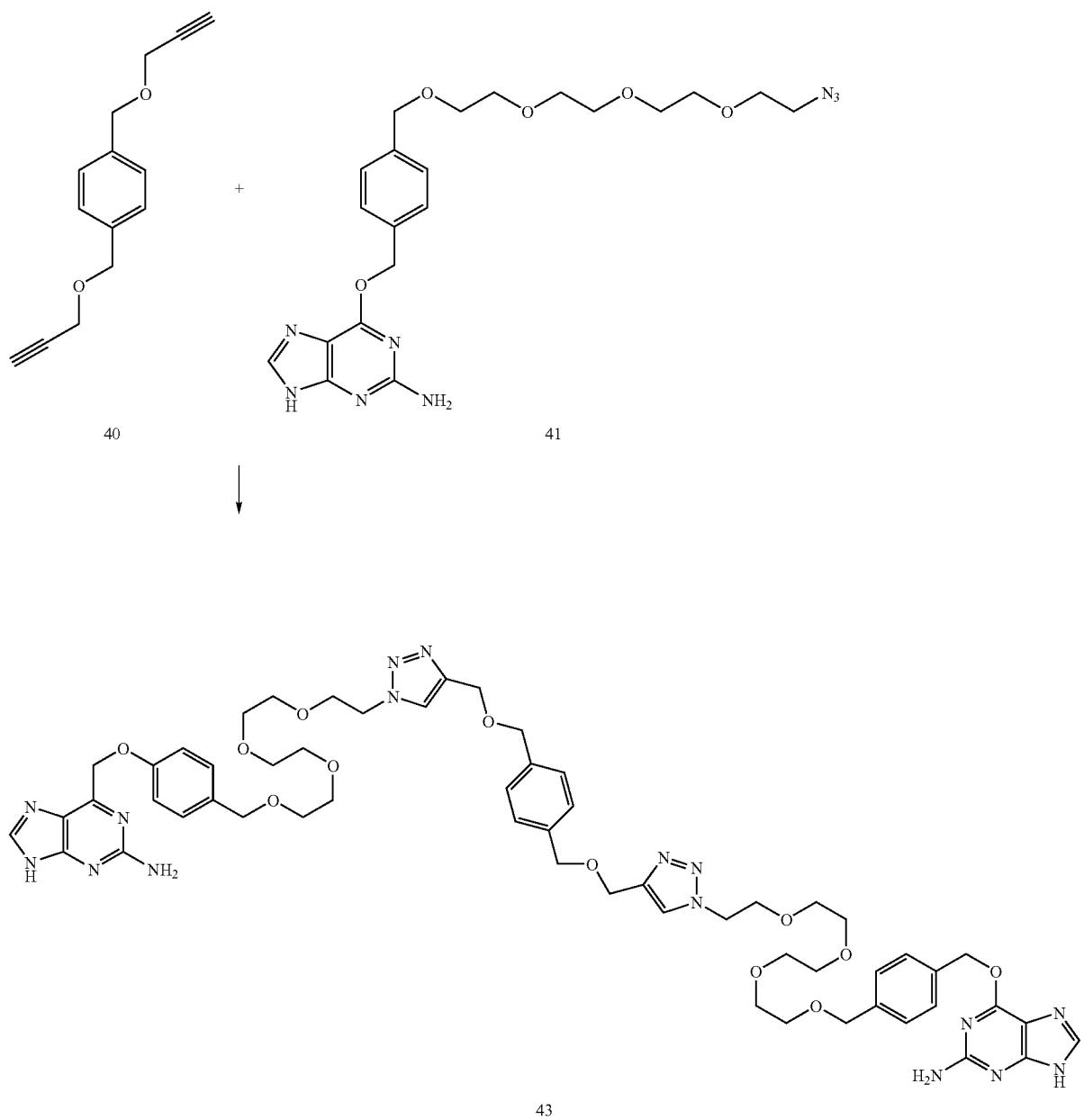
Scheme 7
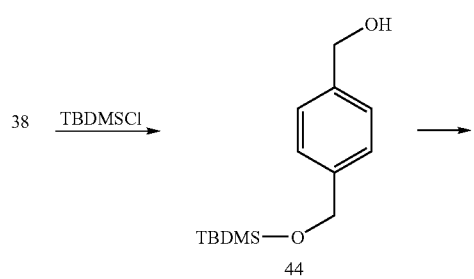
Scheme 8

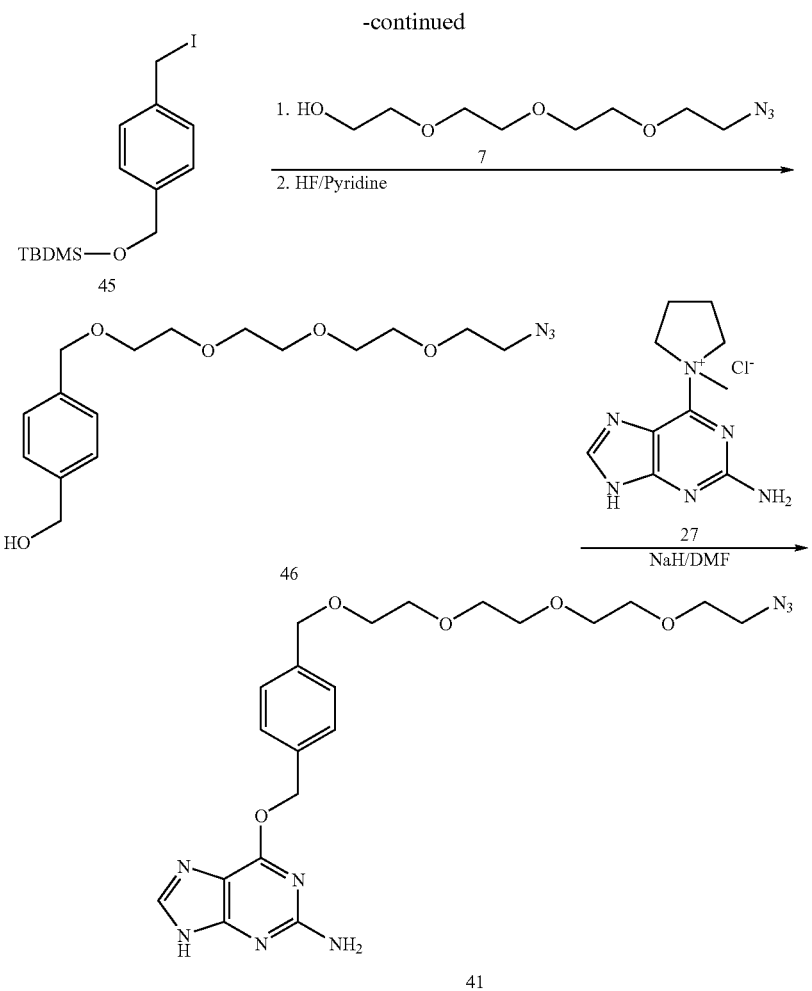

The synthesis of compounds of formula 1 wherein $R_1$ is guanine, $R_2$ is hydrogen, $R_3$ is 1,4-phenylene, $R_4$ is a tetraethyleneoxy unit further comprising a 6-aminocaproyl group and L represents a combination of two different affinity labels is exemplified in Schemes 9 to 11.

For the tri-orthogonal protecting group strategy, ε-N-Fmoc-lysine 47 is converted to the corresponding α-azido-ε-N-Fmoc-lysine 48 by the diazo transfer method (Lundquist et al., J. Org. Lett. 3: 781-783, 2001). Condensation of α-azido-ε-N-Fmoc-lysine with an appropriate functionalized aminobenzylguanine derivative (e.g. 49) under standard peptide coupling conditions leads to the fully protected molecular scaffold 50. The α-azido group is reduced to the corresponding amine 51 under neutral conditions with trimethylphosphine in aqueous 1,4-dioxane, giving a compound suitable for condensation with a variety of different building blocks (containing e.g. affinity labels). For example, coupling with N—(+)-biotin-6-amino-caproic acid N-succinimidyl ester to give 52 followed by Fmoc-deprotection with diethylamine yields intermediate 53 with a free amino group which can be used to couple further labels to the central unit. Digoxygenin-3-O-methylcarbonyl-ε-aminocaproic acid-N-hydroxysuccinimide ester is coupled to the free amino group of 53 leading to the double labelled substrate 54 (Scheme 9).

Scheme 9

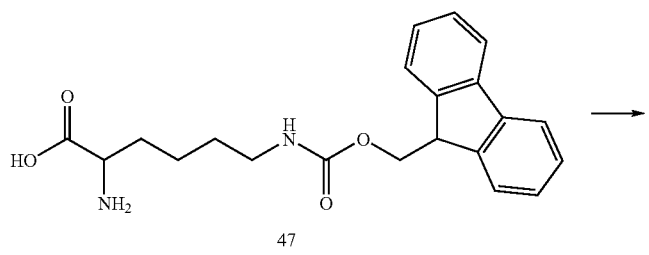

-continued
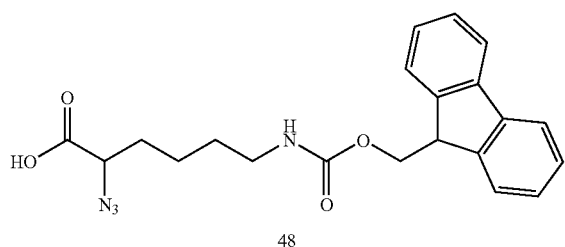
48
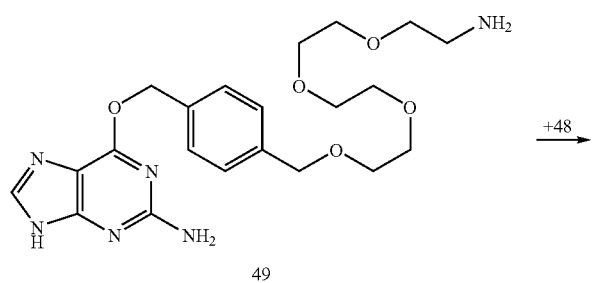
49
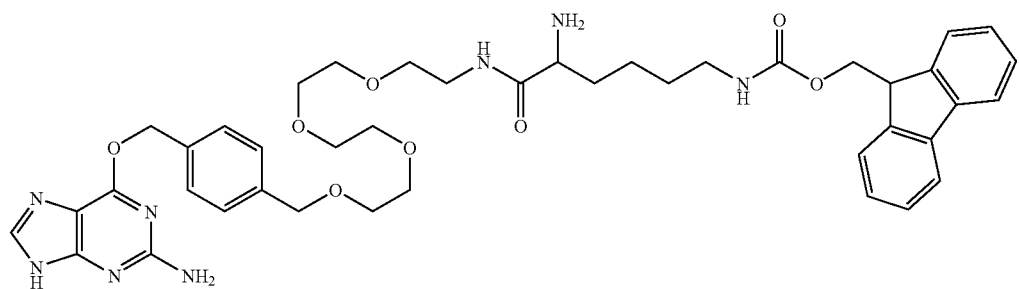
50
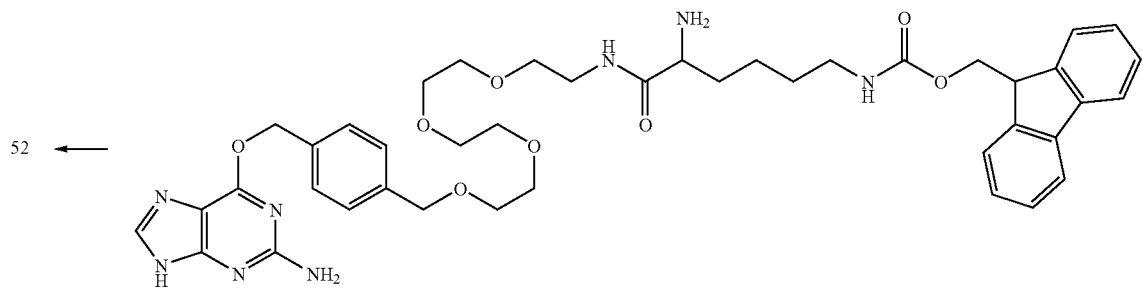
51

-continued
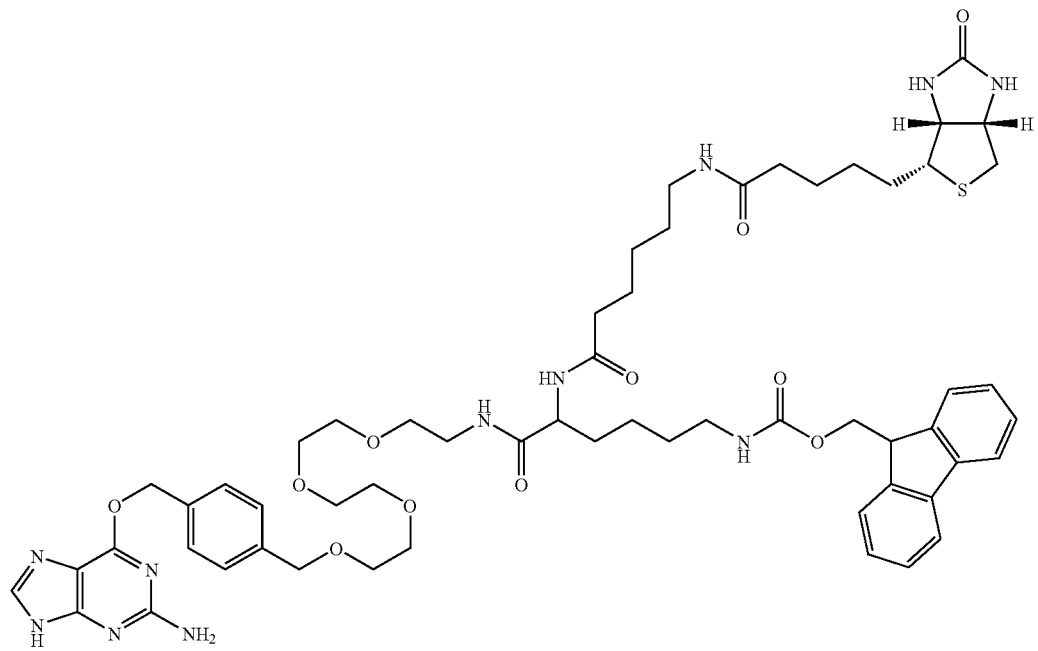
52
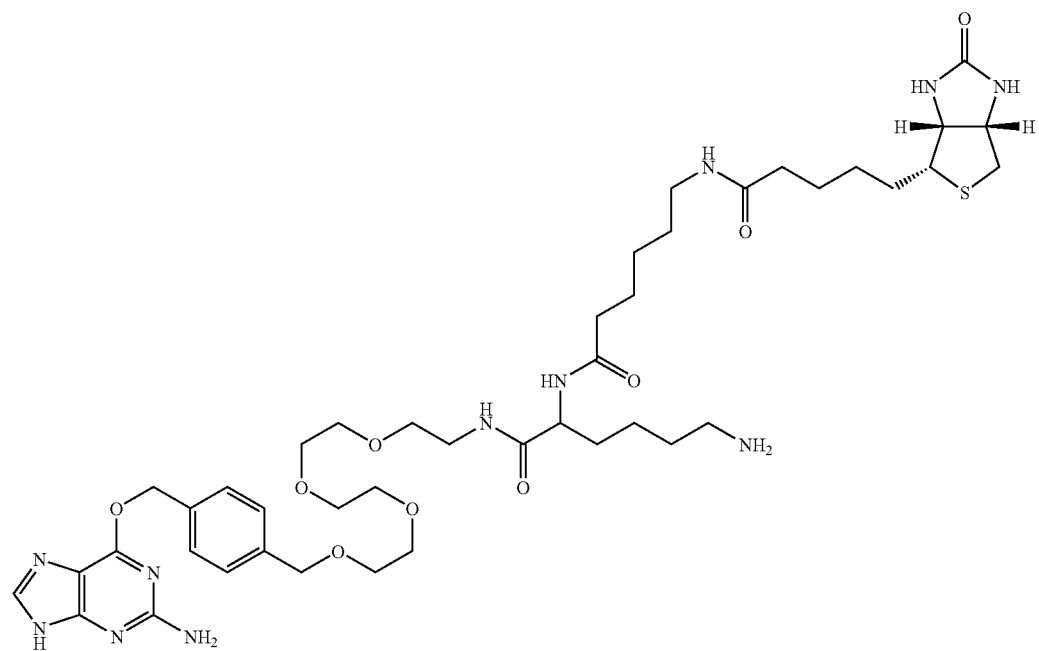
53

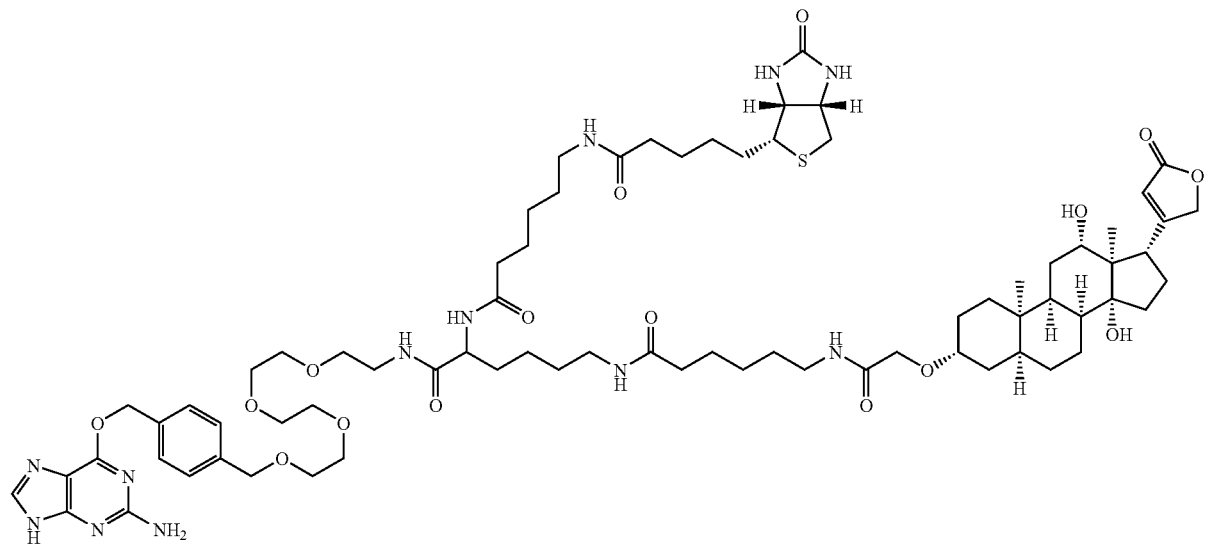
54
Scheme 10
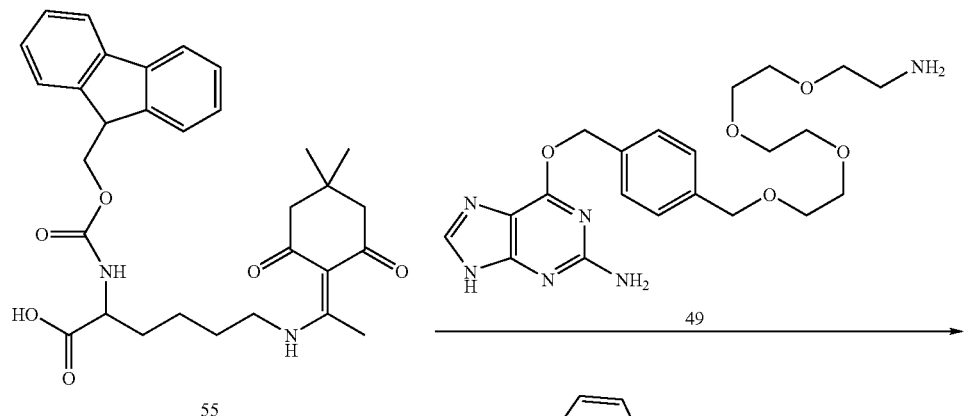
55
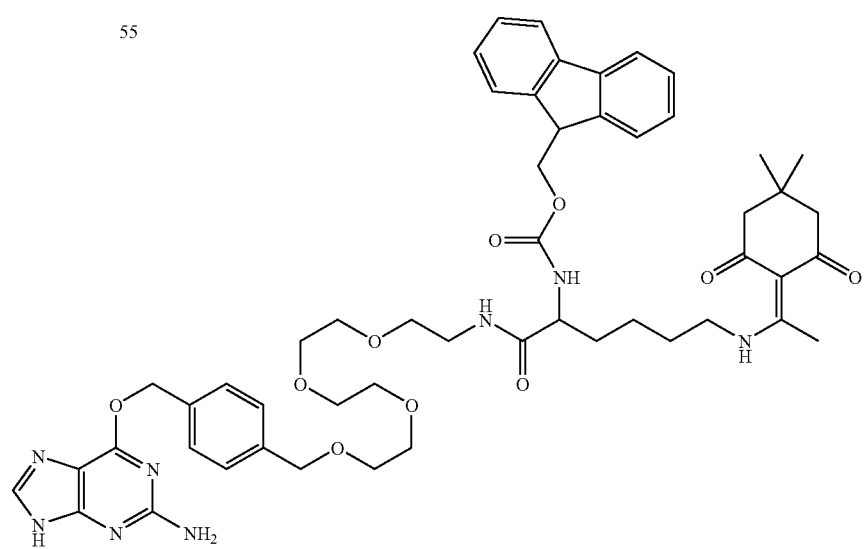
56

-continued

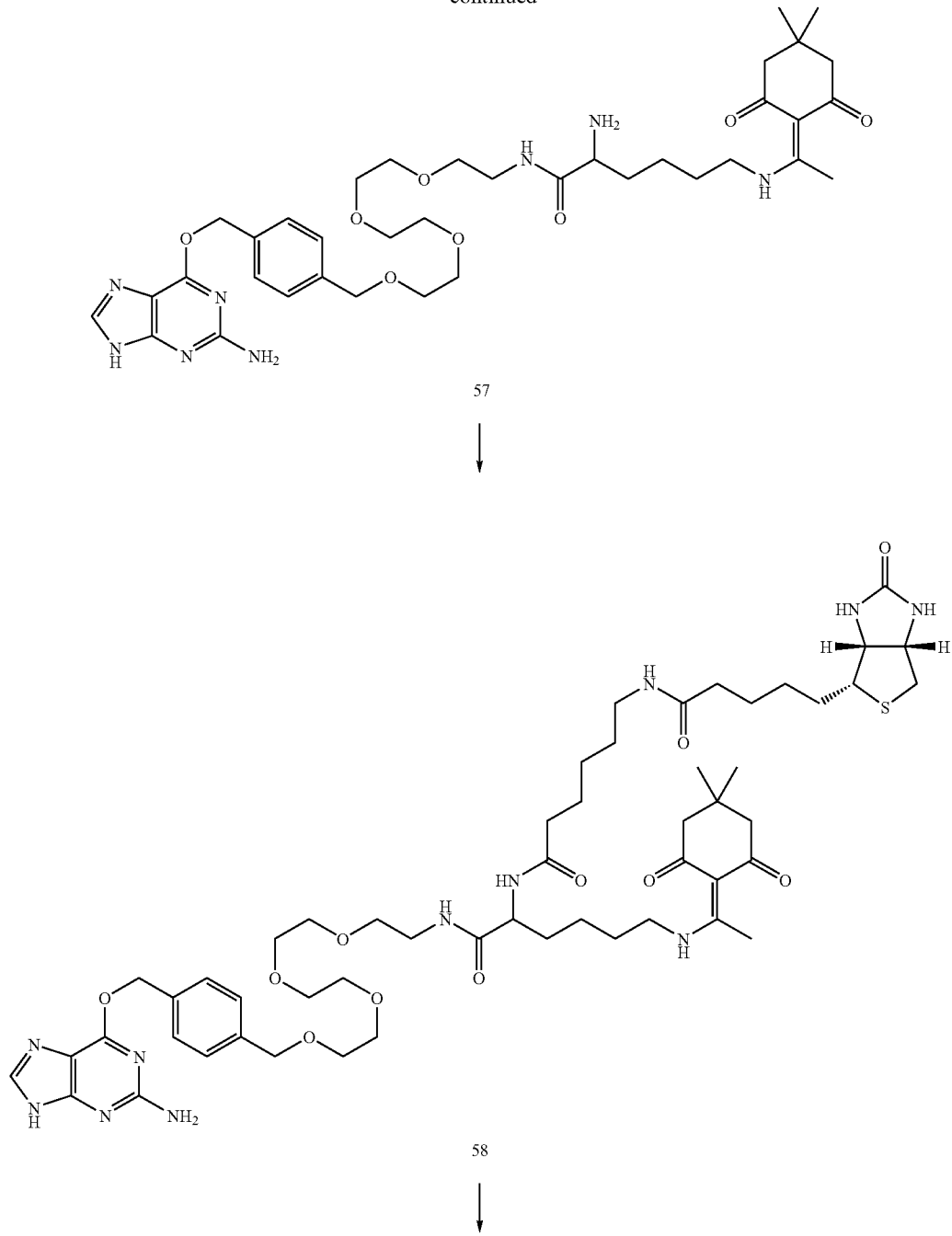

54 ← 53

A different orthogonal protection strategy is illustrated in Scheme 10 for an alternative synthesis of the double labelled substrate 54. Condensation of α-N-Fmoc-ε-N-Dde-lysine 55 with an appropriate functionalized amino-benzylguanine derivatives (e.g. 49) under standard peptide coupling conditions leads to the fully protected molecular scaffold 56. Fmoc-5 deprotection with diethylamine followed by coupling of N—(+)-biotin-6-aminocaproic acid N-succinimidyl ester yields intermediate 58. The remaining Dde-protecting group is cleaved by using a 4% hydrazine solution liberating the second amino group to give compound 53 which can be further derivatized.

Scheme 11

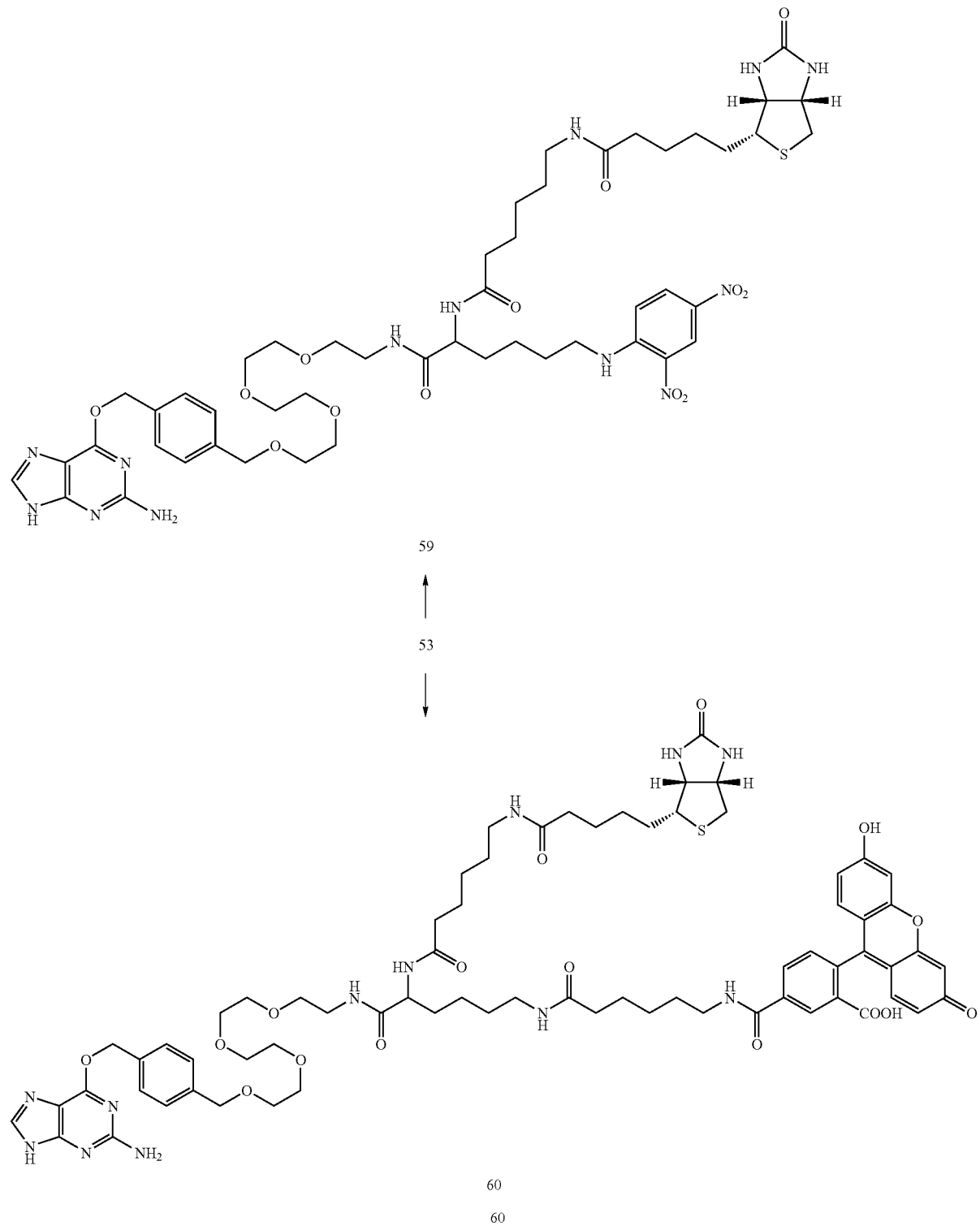

59

53

60
60

Scheme 11 shows the synthesis of two more examples of benzylguanine derivatives bearing a different combination of labels (two affinity labels biotin and dinitrophenyl in 59, or an affinity label combined with a fluorophore in 60). Starting from 53 (see Scheme 9) the coupling of 2,4-dinitrofluorobenzene to the free amino group yields 59. Coupling of the free amino group in 53 with fluorescein-5(6)-carboxamidocaproic acid N-succinimidyl ester gives 60.

A further compound of formula 1 wherein $R_1$ is guanine, $R_2$ is hydrogen, $R_3$ is 1,4-phenylene, $R_4$ is a dimeric tetraethyleneoxy unit coupled through a urea function and L is —$R_3$—$CH_2$—X—$R_1$-$R_2$ is prepared as shown in Scheme 12:

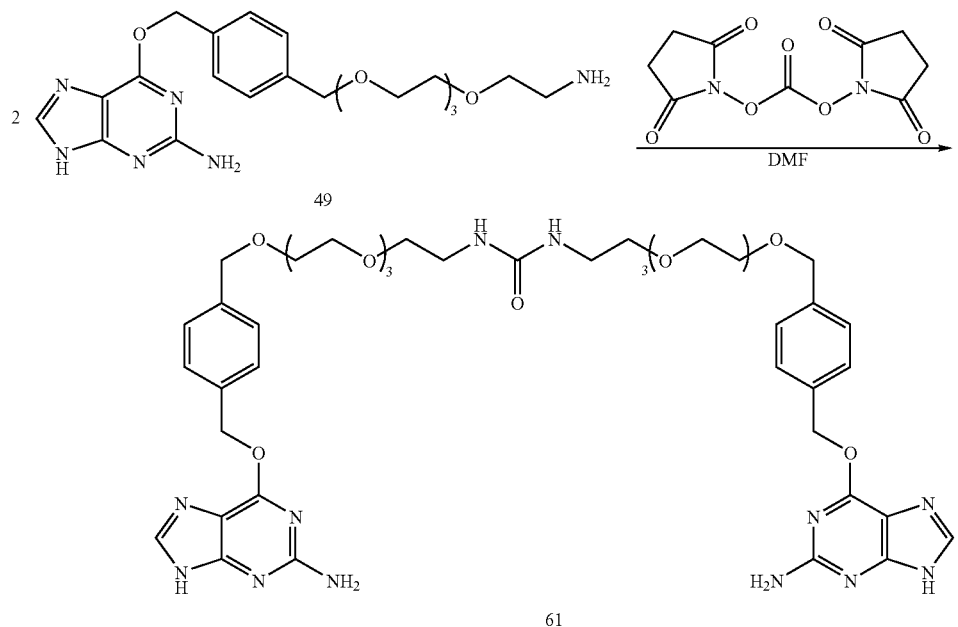
The synthesis of a compound of formula 1 wherein $R_1$ is guanine, $R_2$ is hydrogen, $R_3$ is propargyl, $R_4$ is a tetraethyleneoxy unit further comprising a 6-aminocaproyl group and L is biotin is shown in Scheme 13 and 14:
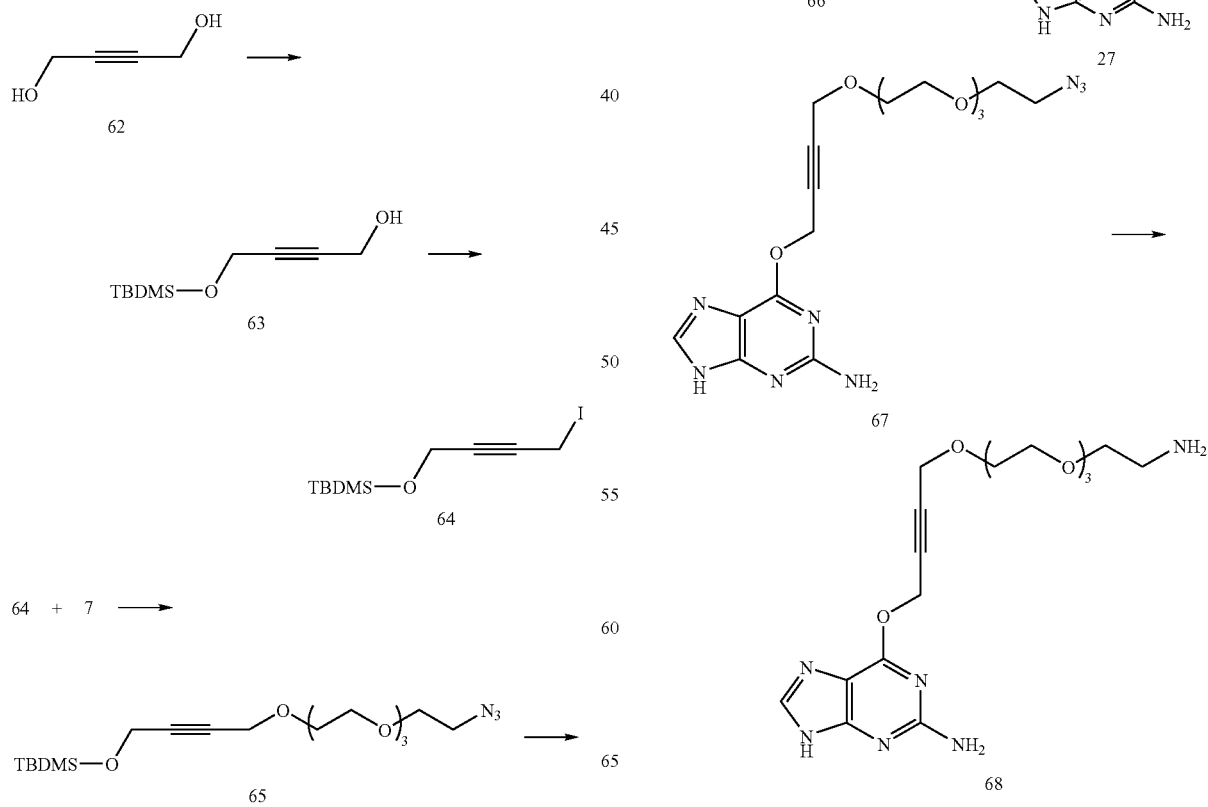

Scheme 14
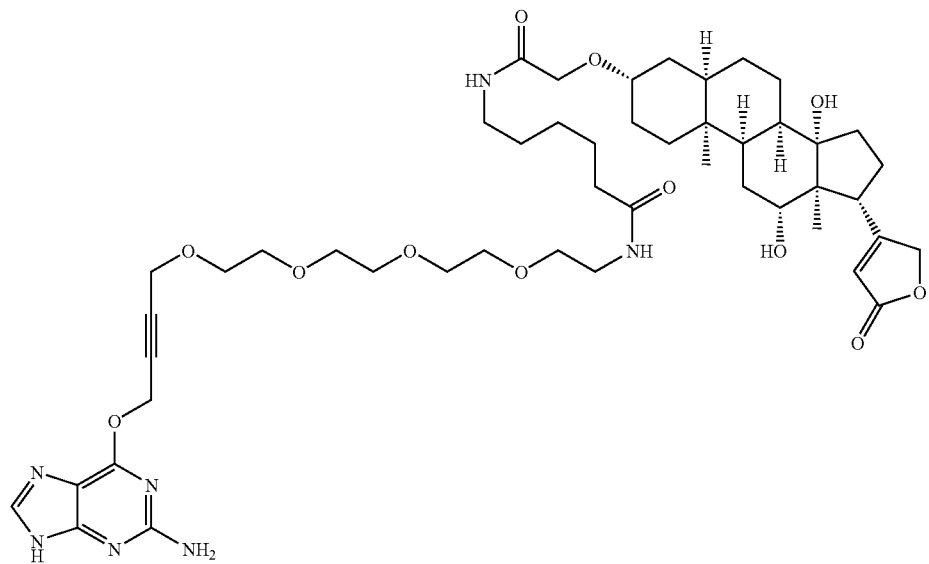
69
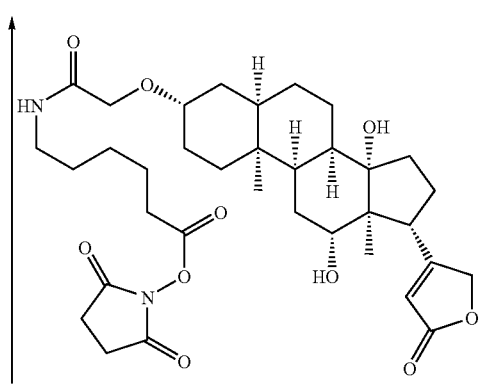
68
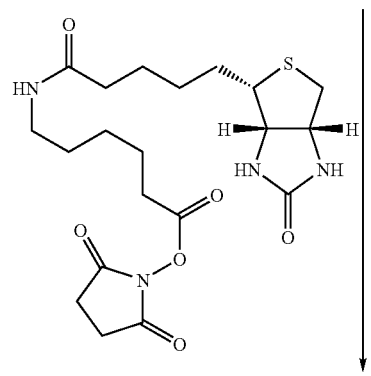

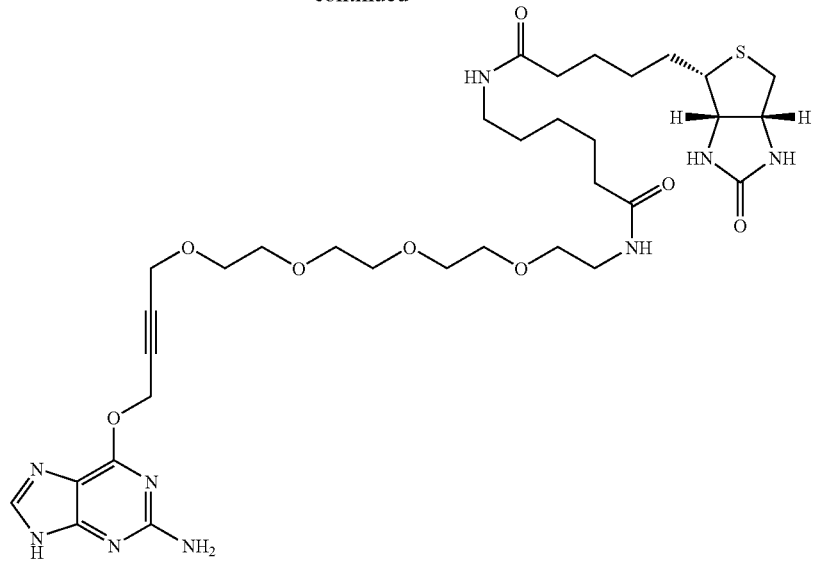

70

The synthesis of a benzylguanine derivatives with an enzyme inhibitor as a label L acting as a small molecule to induce protein dimerization in living cells based on the covalent labeling of fusion proteins with synthetic ligands capable of interacting with other proteins is shown in Scheme 15 and 16. In particular, the synthesis of a compound of formula 1 wherein $R_1$ is guanine, $R_2$ is hydrogen, $R_3$ is 1,4-phenylene, $R_4$ is either a ω-amino-dodecanoylamino-methyl residue or a tetraethyleneoxy unit further comprising a glutamic acid unit and L is methotrexate is described. Methotrexate is a tight-binding inhibitor of the enzyme dihydrofolate reductase, and these heterodimeric structures belong to the well known class of compounds of so-called "chemical inducers of dimerization" (CIDs).

Scheme 15

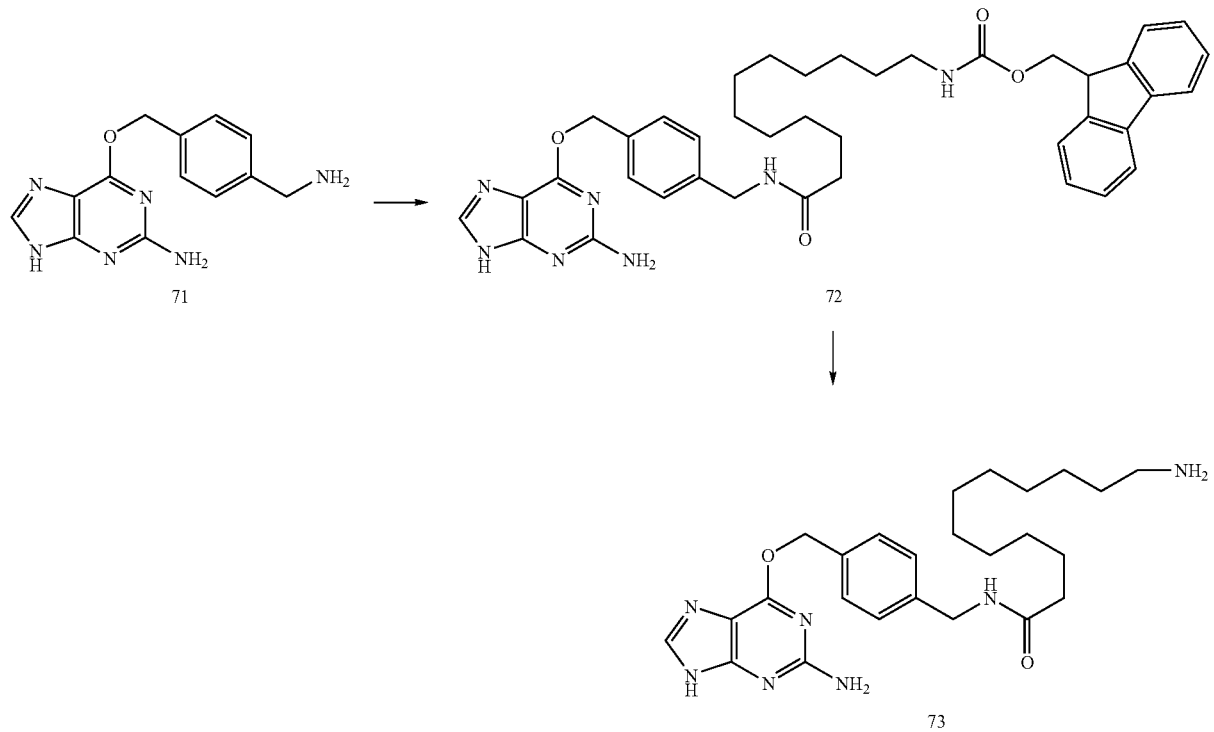

-continued
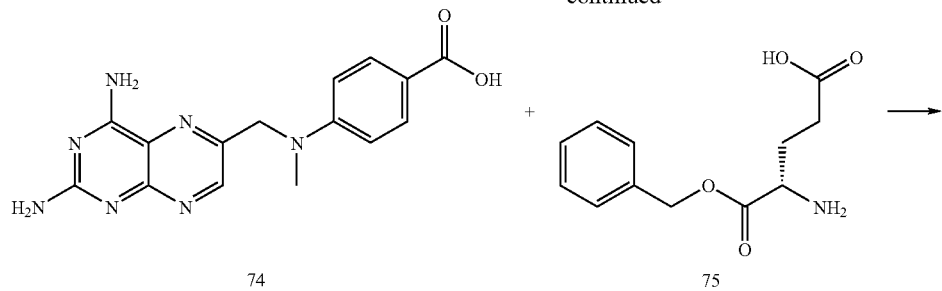
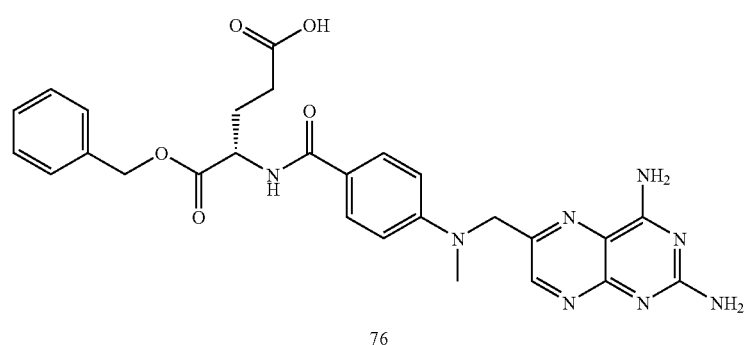
73 + 76 ⟶
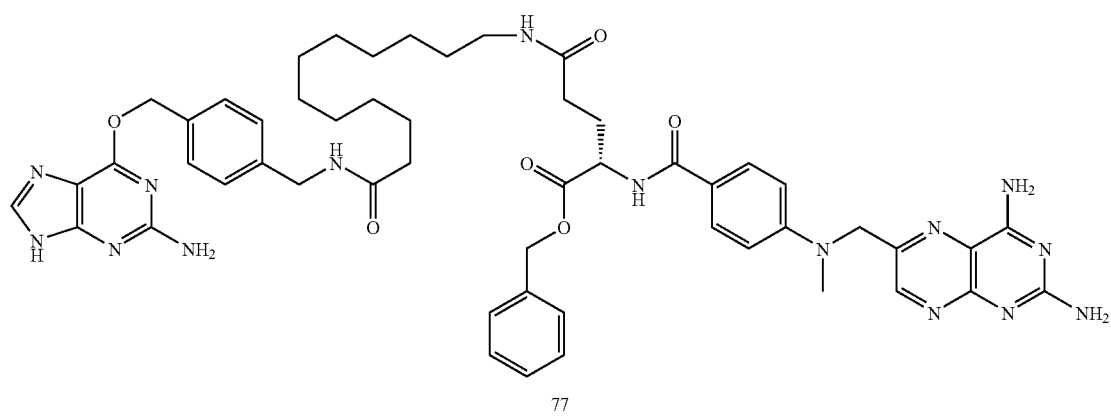
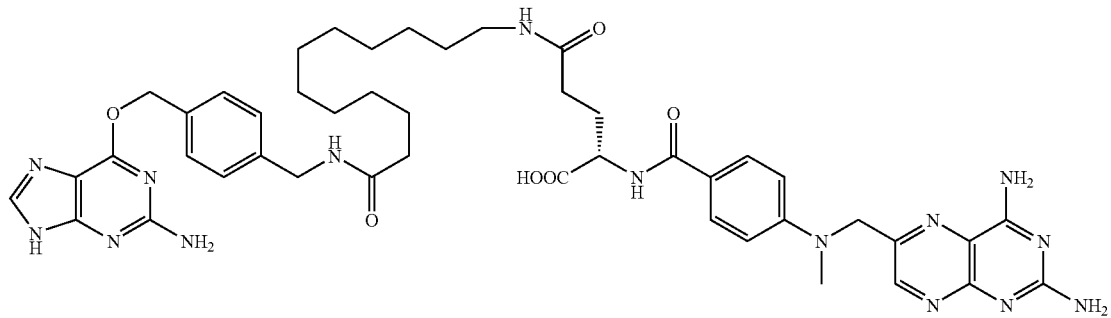

Scheme 16
49 + 76 →
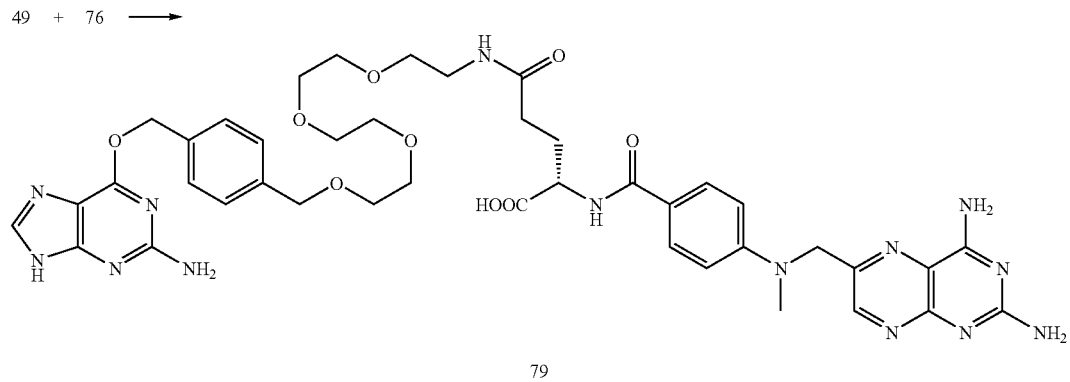
79
Compounds of formula 1 wherein $R_1$ is guanine, $R_2$ is hydrogen, $R_3$ is 1,4-phenylene, $R_4$ is a but-2-en-1,4-diol derivative and L is —$R_3$—$CH_2$—X—$R_1$-$R_2$ is prepared as shown in Scheme 17 and 18.
Scheme 17
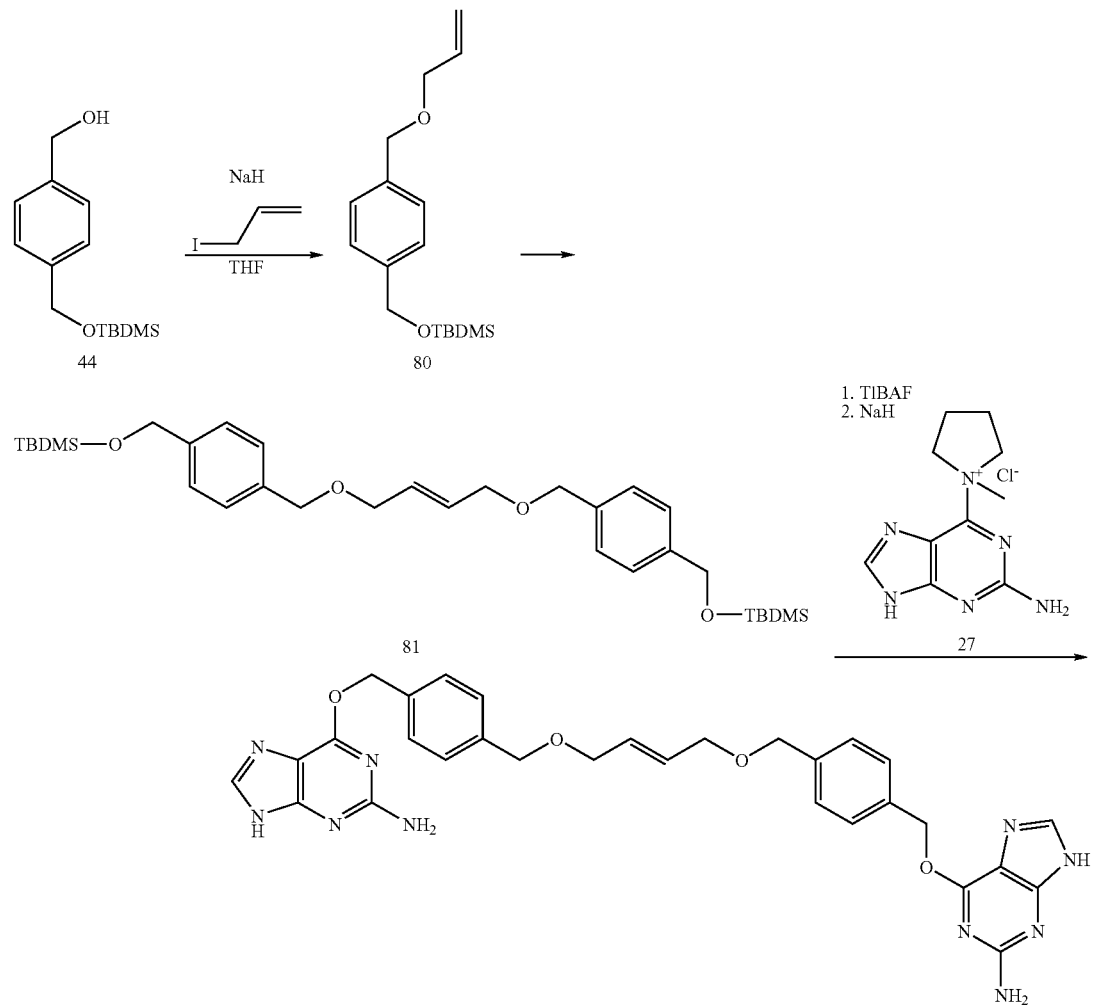

Scheme 18
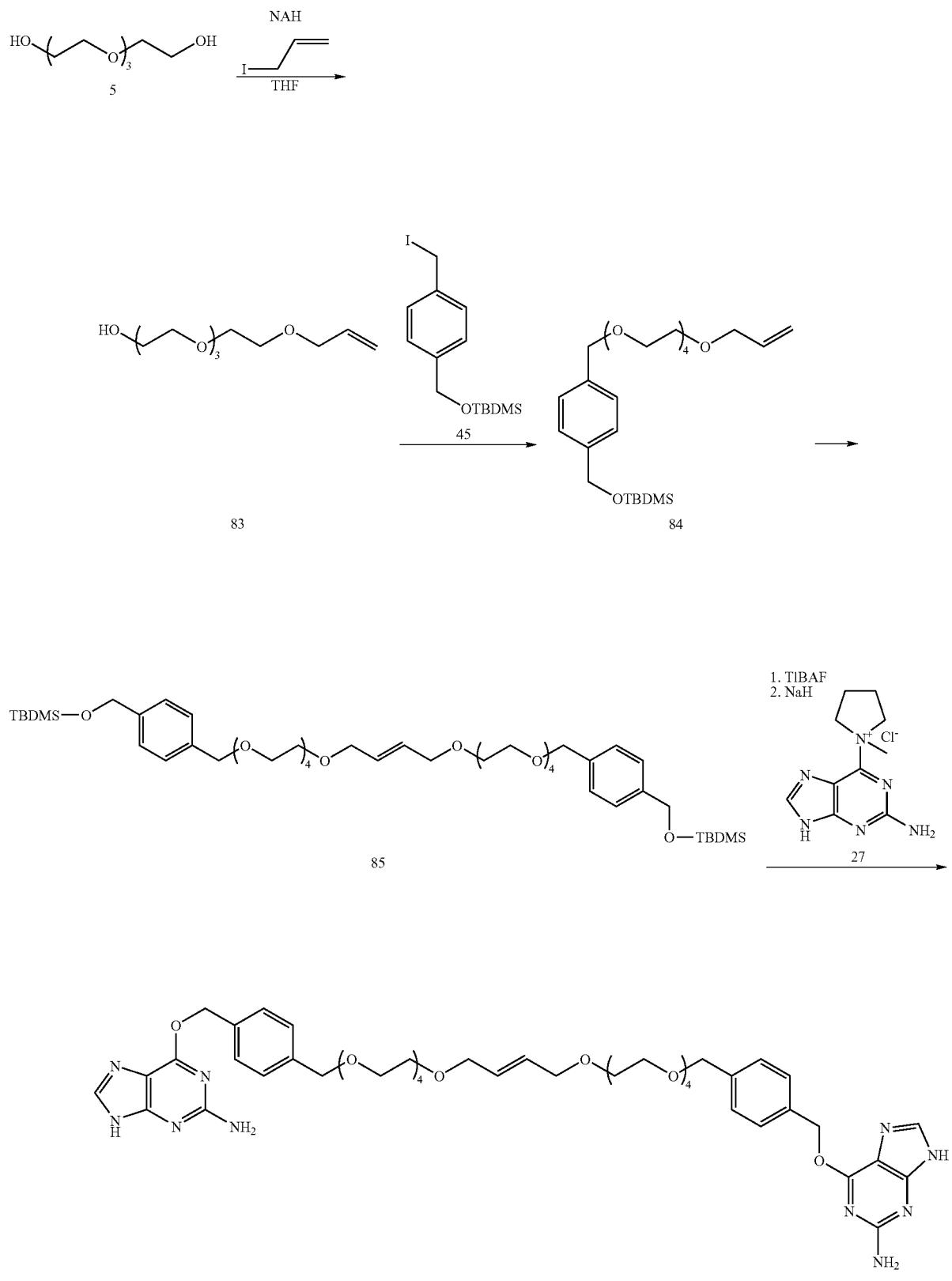

It is assumed that the polar solvents necessary to dissolve O⁶-benzylguanine derivatives are not compatible with the olefin metathesis catalyst benzylidene-bis(tricyclohexylphosphine)-dichlororuthenium. Therefore, first the protected symmetric core units 81 and 85 are built and, after deprotection, the final bis-benzylguanines 82 and 86 are synthesized.

Particularly preferred compounds of the invention are those shown in Scheme 1 to 18, and compounds described in the Examples.

EXAMPLES

Example 1

Preparation of Glass Slides for the Covalent Attachment of AGT Substrates and Subsequent Covalent Immobilization of AGT Fusion Proteins for the Preparation of Protein Microarrays A commercially available microscope glass slide ($SiO_2$) is cleaned thoroughly with dichloromethane, acetone, $H_2O_2$/$H_2SO_4$ in an ultrasonic bath, and bi-distilled water. It is aminosilylated using 3-aminopropyltriethoxysilane in a solvent mixture ethanol/water (95:5) for 1 h following a published procedure, then treated with a solution of disuccinimidyl glutarate (10 mM) in dichloromethane/diisopropylethylamine (100:1) for 2 h under argon at room temperature. The surface is washed several times with dichloromethane. The glass surface bearing activated carboxy functions is incubated for 4 h with a solution of a compound of formula 1 bearing a free amino group instead of label L, such as compound 11, 13, 16, 18, 28, 34, 49, 68 or 73, in methanol in a concentration of 10 mM, and supplemented with triethylamine. The slides are washed at least three times with methanol to yield a surface with the corresponding AGT-substrate covalently attached by an amide bond. To avoid side reactions in further use of the slides, all unreacted succinimidyl groups are quenched by addition of 6-aminohexanol (100 mM in DMF).

Example 2

11-Azido-3,6,9-trioxaundecanol (7) and 1,11-diazido-3,6,9-trioxaundecane (36)

A solution of 50.0 g (260 mM) tetraethylene glycol and 50 mL triethylamine in 200 mL dry diethyl ether is cooled to 0° C. under an argon atmosphere, and 15.0 g (130 mM) methanesulfonyl hloride is added over a 3 h period and stirred at room temperature for 20 min. The solvent is removed in vacuo, and 300 mL 95% ethanol and 18.0 g (280 mM) sodium azide are added. The mixture is heated to reflux for 24 h, cooled to room temperature and concentrated in vacuo. The remaining mixture is diluted with 400 mL dichloromethane, washed with brine and dried over $MgSO_4$. After concentration in vacuo the crude mixture of mono- and diazide is purified by silica gel chromatography (petrol ether/ethyl acetate 3:1) yielding 15.03 g (68.5 mmol, 26%) monoazide and 3.46 g (14.18 mmol, 5.5%) diazide.

Example 3

1-Azido-11-phtalimido-3,6,9-trioxaundecane (8)

A solution of 1.17 g (5.35 mmol) 11-azido-3,6,9-trioxaundecanol (7) and 1.2 mL triethylamine in 35 mL methylene chloride is cooled to 0° C., and 0.5 mL (6.45 mmol) methanesulfonyl chloride is added dropwise via a syringe over a 20 min period. The mixture is warmed to room temperature and stirred for 1.5 h. The mixture is then washed twice with 10 mL of saturated aqueous $NaHCO_3$ and three times with 5 mL of water. The organic layer is dried and concentrated in vacuo to yield 1.5 g 8 as a yellow oil which is used without further purification.

Example 4

4-Bromothenyl Alcohol (20)

5.0 g (26.17 mmol) 4-Bromothiophene-2-carboxaldehyde (19) is dissolved in 75 mL iso-propanol, and 1.11 g (29.31 mmol) $NaBH_4$ is added at once and the mixture stirred for 2 h. 20 mL saturated aqueous $NH_4Cl$ is added, the solid removed by filtration and the mixture concentrated in vacuo. The product is purified by silica gel chromatography (petrol ether/ethyl acetate 10:1), yielding 4.64 g 20 (24.07 mmol, 92%) as a colorless solid.

Example 5

4,7,10,13-Tetraoxa-1-pentadecen-15-ol (22)

2.3 g (19.5 mmol) Potassium tert-butoxide is dissolved in 500 mL dry THF, and 7.18 g (37 mmol) tetraethylene glycol is added dropwise. After stirring for 30 min, a solution of 3.31 g (19.7 mmol) allyl iodide in 60 mL dry THF is added over 1 h, and stirring is continued for 24 h. The crude mixture is filtered over silica gel and the solvent removed in vacuo. The product is purified by silica gel chromatography (gradient: petrol ether/ethyl acetate 10:1→ethyl acetate), yielding 2.41 g 22 (10.3 mmol, 27%) as a colorless liquid.

Example 6

1-(2-Amino-7H-purin-6-yl)-1-methyl-pyrrolidinium chloride (27)

1.0 g (5.9 mmol) 6-Chloroguanine is dissolved in 40 mL DMF at 40° C. After cooling to room temperature, 1.4 mL 1-methylpyrrolidine (13.2 mmol) is added, and the reaction mixture is stirred for 18 h. 2 mL of acetone are added to complete precipitation. The solid is filtered, washed with ether and dried in vacuo, yielding 1.03 g 27 (3.9 mmol, 66%).

Example 7

O⁶-(4-Aminomethyl-benzyl)guanine (32)

a) 4-Aminomethyl-benzyl Alcohol: 2.83 g $LiAlH_4$ (74.5 mmol) are suspended in 150 mL dry ether, and 1.9 mL $H_2SO_4$ (100%, 37.2 mmol) are added dropwise and under cooling. The mixture is stirred for 1 h at room temperature, followed by dropwise addition of 2.0 g (12.4 mmol) 4-cyanobenzoate in 12 mL ether. After 2 h of refluxing the reaction is quenched with 20 mL water followed by 7.4 g NaOH in 60 mL water. The organic layer is decanted, and the aqueous layer extracted with ether and ethyl acetate. The organic layer is dried over $MgSO_4$, the solvent is removed and the product dried in vacuo, yielding 0.92 g (6.7 mmol, 54%). b) 2,2,2-Trifluoro-N-(4-hydroxymethyl-benzyl)acetamide: To a solution of 866 mg (6.3 mmol) 4-aminomethyl-benzyl alcohol and 880 μL (6.3 mmol) triethylamine in 10 mL dry methanol 980 μL (8.2 mmol) trifluoroacetic acid ethyl ester are added dropwise. The reaction mixture is stirred for 45 min, and diluted with 10 mL ethyl acetate and 10 mL water. The aqueous layer is extracted with ethyl acetate, and the combined organic layers are washed with saturated NaCl and dried over $Na_2SO_4$. After removal of the solvents in vacuo the crude product is purified by flash column chromatography (ethyl acetate/cyclohexane 1:2). Yield: 1.32 g (5.7 mmol, 90%).

c) N-[4-2-Amino-7H-purin-6-yloxymethyl)-benzyl]-2,2,2-trifluoroacetamide:

592 mg (2.54 mmol) 2,2,2-trifluoro-N-(4-hydroxymethyl-benzyl)acetamide are dissolved in dry DMF under argon atmosphere, and 599 mg (5.33 mmol) potassium tert-butoxide are added. 300 mg (1.18 mmol) 1-(2-amino-7H-purin-6-yl)-1-methylpyrrolidinium chloride (27) is then added and the solution stirred for 3 h. After removal of the solvent in vacuo the crude product is purified by flash column chromatography (300 mL methanol/dichloromethane 1:50, 500 mL methanol/dichloromethane 1:10). Yield: 382 mg (1.04 mmol, 88%).

d) $O^6$-(4-Aminomethyl-benzyl)guanine (32): 335 mg (0.91 mmol) N-[4-(2-amino-7H-purin-6-yloxymethyl)-benzyl]-2,2,2-trifluoroacetamide is suspended in 34 mL methanol and 2 mL water. After addition of 656 mg (4.75 mmol) of $K_2CO_3$ the reaction mixture is refluxed for 2 h. The solvents are removed in vacuo and the product is purified by flash column chromatography (methanol/triethylamine/dichloromethane 1:0.05:5). Yield: 209 mg 32 (0.77 mmol, 85%).

Example 8

$O^6$-(4-[Prop-2-ynyloxymethyl]-benzyl)guanine (35)

662 mg (3.8 mmol) 4-(Prop-2-ynyloxymethyl)-benzyl alcohol (39) is dissolved in 3 mL dry DMSO, and 61 mg NaH are added in small portions over 5 min. 300 mg (1.27 mmol) 1-(2-amino-7H-purin-6-yl)-1-methylpyrrolidinium chloride (27) is added and the mixture is stirred for additional 4 h. The reaction is quenched with 0.2 mL of acetic acid, evaporated to dryness and purified by flash column chromatography (gradient: dichloromethane/methanol 50:1→10:1) to yield 188 mg 35 (0.61 mmol, 53%).

Example 9

Homo-$O^6$-benzylguanine-dimer 37

To a solution of 50.0 mg (0.162 mmol) $O^6$-(4-[prop-2-ynyloxymethyl]-benzyl)guanine (35) and 19.7 mg (0.081 mmol) 1,11-diazido-3,6,9-trioxaundecane (36) in 0.5 mL DMF a suspension of 15.43 mg (0.081 mmol) $Cu_2I_2$ in 0.15 mL of water is added. The mixture is stirred at room temperature for 24 h.

Example 10

4-(Prop-2-ynyloxymethyl)benzyl alcohol (39) and 1,4-bis-(prop-2-ynyloxy-methyl)benzene (40)

To a solution of 2.5 g (18.1 mmol) 4-hydroxymethylbenzyl alcohol (38) 477.5 mg (19.9 mmol) NaH is added in small portions over 20 min. 2.15 mL of a propargyl bromide solution (80% in toluene) is added dropwise and stirred for 15 h. 100 mL of water are added to the mixture, and the products extracted with diethyl ether. The combined phase is dried and the solvent removed in vacuo. The separation of the products is achieved by silica gel chromatography (petrol ether/ethyl acetate 4:1) yielding 1.08 g 39 (6.17 mmol, 34%) and 1.05 g 40 (4.94 mmol, 27%).

Example 11

4-[tert-Butyldimethylsilyloxy)methyl]benzyl alcohol (44)

810 mg (33.77 mmol) NaH are suspended in 90 mL dry THF at room temperature, and 4.2 g (30.39 mmol) solid 4-hydroxymethyl-benzyl alcohol (38) is added in three portions over 5 min, and the reaction mixture is stirred for 45 min. 4.83 g (32.08 mmol) tert-butyldimethylsilyl chloride are added in three portions over 5 min and stirred for an additional 1.5 h before the mixture is quenched with water and then diluted with 100 mL of water and 100 mL of diethyl ether. The organic phase is separated and the aqueous phase is extracted with diethyl ether. The combined organic phases are washed with brine, dried over $MgSO_4$, filtered and concentrated in vacuo. The product is purified by flash chromatography (petrol ether/ethyl acetate 10:1) to yield 3.0 g 44 (11.88 mmol, 40%).

Example 12

1-[(tert-Butyldimethylsilyloxy)methyl]-4-(iodomethyl)benzene (45)

9.15 g (34.88 mmol) Triphenylphosphine and 3.2 g (44.5 mmol) imidazole are dissolved in a 3:1 mixture of diethyl ether/acetonitrile (30 mL). 8.85 g (34.9 mmol) iodine is added under vigorous stirring until a yellow suspension has formed. A solution of 6.1 g (23.25 mmol) of the monoprotected benzyl alcohol 44 in 20 mL of the same solvent mixture is added, and the mixture is stirred for 2 h. The solid is removed by filtration, the filtrate diluted with 100 mL of diethyl ether and washed with 100 mL of a saturated solution of sodium bisulfite. The aqueous solution is back-extracted with diethyl ether, the combined organic phases dried over $MgSO_4$ and concentrated in vacuo. Flash chromatography (petrol ether/ethyl acetate 95:5) yields 4.8 g 45 (13.25 mmol, 57%).

Example 13

4-(13-Azido-2,5,8,11-tetraoxatridecyl)-benzyl alcohol (46)

4.8 g (13.25 mmol) 1-[(tert-Butyldimethylsilyloxy)methyl]-4-(iodomethyl)benzene (45) is dissolved in 70 mL dry THF under argon, and 0.954 g (39.75 mmol) NaH is added in small portions over 10 min. A solution of 3.2 g (14.58 mmol) 1-azido-3,6,9-trioxaundecanol (7) in 20 mL dry THF is added dropwise, and the reaction mixture stirred for 15 h at room temperature. 2 mL of water are added to quench the reaction, and the mixture is concentrated to about 50% under reduced pressure. 70 mL of water are added, and the reaction mixture extracted with diethyl ether. The organic phase is dried over $MgSO_4$ and the solvent removed. Purification by silica gel chromatography (gradient: petrol ether/ethyl, acetate 10:1→3:1) yields 3.8 g (8.38 mmol, 63%) of the TBDMS-protected product. It is dissolved in 80 mL dry THF in a plastic tube, cooled to 0° C., and 8 mL of a pyridine/HF (70:30) solution is added and stirred for 3 h at room temperature. 100 mL of aqueous saturated $NaHCO_3$ are added, the organic phase separated, washed with brine and dried over $MgSO_4$. After removal of the solvent the product is purified by silica gel chromatography (petrol ether/ethyl acetate 1:1) to yield 1.27 g 46 (2.87 mmol, 74%).

Example 14

$O^6$-[4-(13-Azido-2,5,8,11-tetraoxatridecyl)-benzyl] guanine (41)

0.974 g (2.87 mmol) 4-(13-azido-2,5,8,11-tetraoxatridecylybenzyl alcohol (46) is dissolved in 5 mL dry DMF, and 1.3 g (11.5 mmol) potassium tert-butoxide are added. 0.731 g (2.87 mmol) 1-(2-amino-7H-purin-6-yl)-1-methyl-pyrrolidinium chloride is added and the solution stirred for 22 h. After removal of the solvent in vacuo the crude product is purified by flash column chromatography (methanol/dichloromethane 5:95). Yield: 0.675 g (50%).

Example 15

Hetero-$O^6$-benzylguanine-dimer 42

To a solution of 45 mg (0.09 mmol) azide 41 and 29.5 mg (0.09 mmol) $O^6$-(4-[prop-2-ynyloxymethyl]-benzyl)guanine (35) in 1 ml water/acetonitrile 1:1 a suspension of 9.8 mg $Cu_2I_2$ in 0.1 mL water is added, and the reaction mixture is stirred for 24 h at room temperature. All insoluble material is filtered off, the solvents evaporated in vacuo and the product purified by flash column chromatography (methanol/dichloromethane 5:1) yielding 3.5 mg (0.004 mmol, 10%). ESI/MS: 781.44 ($M^+$).

Example 16

Homo-$O^6$-benzylguanine-dimer 43

Azide 41 (100 mg, 0.21 mmol) and 1,4-(diprop-2-ynyloxymethyl)benzene (40) (22.6 mg, 0.10 mmol) are dissolved in a solvent mixture consisting of 300 µL ethanol, 200 µL water and 500 µL tert-butanol. 10 µL $CuSO_4$ solution (40 mM), 5 mg Cu-wire and 3 mg $Cu_2I_2$ are added, and the reaction mixture is stirred at room temperature for 48 h. All insoluble material is filtered off, the solvent evaporated in vacuo, and the product purified by flash column chromatography (chloroform/methanol 20:1) yielding 34 mg (28%) of dimer 43. ESI/MS: 1159.37 ($M^+$).

Example 17

11-Amino-1-azido-3,6,9-trioxaundecane (9)

1-Azido-11-phtalimido-3,6,9-trioxaundecane (8, Example 3, 2.0 g, 5.74 mmol), is treated with 1.0 ml 55% hydrazine hydrate in 50 ml abs. methanol and heated to reflux for 2 h. After cooling to room temperature, the mixture is concentrated in vacuo, diluted with 50 ml of water and treated with 5 ml conc. HCl. All precipitate is filtered off, the aqueous filtrate neutralized with NaOH, and the solvent removed in vacuo. The residue is dissolved in dichloromethane, and washed with 3 N NaOH and water. The organic phase is dried over $MgSO_4$ and concentrated in vacuo yielding 0.63 g (2.9 mmol, 51%) of a colourless oil, which is used in the next step without further purification.

Example 18

$O^6$-(1-[11-Amino-3,6,9-trioxaundecyl]-1,2,3-triazolyl-4-methyl)guanine (11)

$O^6$-Propargyl-guanine 10 (75 mg, 0.4 mmol) and azide 9 (44 mg, 2 mmol) are dissolved in a solvent mixture of 400 µL N,N-dimethylacetamide, 100 µL acetonitrile and 100 µL water. 10 µL of a $CuSO_4$-solution (40 mM), Cu-wire (5 mg) and $Cu_2I_2$ (2 mg) are added, and the reaction mixture stirred at room temperature for 48 h. All insoluble material is filtered off, and the solvents evaporated in vacuo. Flash chromatography (dichloromethane/methanol 20:1) yields 35 mg 11 (21%).

Example 19

α-Azido-ε-N-Fmoc-lysine 48

18 mL Triflyl azide (6.3 mmol, 2.3 eq. in dichloromethane) is added to ε-N-Fmoc-lysine 47 (1.10 g, 2.98 mmol) and $CuSO_4$ (8 mg) in 27 mL of a solvent mixture water/methanol 1:2. Diisopropylethylamine (971 µL, 5.58 mmol) is added, and the reaction mixture is stirred at room temperature over night. The organic solvents are removed in vacuo and 100 mL water is added. The pH is adjusted to 2.5 with 6 N HCl. After extraction with ethyl acetate the combined organic fractions are washed with water and dried ($MgSO_4$). Evaporation of the solvent affords the crude product as a yellow oil. Flash chromatography (dichloromethane/methanol 97:3) gives 670 mg (59%) of a white solid. $R_f$=0.32 (dichloromethane/methanol 95:5). ESI-MS (m/z) 395.23 $[M+H]^+$ (MW calcd.=394.3).

Example 20

$O^6$-[4-(13-Amino-2,5,8,11-tetraoxatridecyl)benzyl] guanine (49)

$O^6$-[4-(13-Azido-2,5,8,11-tetraoxatridecylybenzyl]guanine (41, 0.21 g, 0.44 mmol) is dissolved in 8 ml dry methanol by heating. Triethylamine (410 µL, 2.2 mmol) and 1,3-propanedithiol (225 µL, 2.2 mmol) are added under an argon atmosphere. The reaction mixture is heated at 40° C. and stirred for 48 h. The solution is decanted, the solid washed with methanol, and the solvent evaporated in vacuo. The residue is purified by flash column chromatography (dichloromethane/methanol 95:5), and the title compound obtained as a pale yellow oil (120 mg, 0.26 mmol, 61%). $R_f$=0.01 (dichloromethane/methanol 9:1). $^1$H-NMR (400 MHz, DMSO-$d_6$) δ 7.83 (s, 1H), 7.47 (m, 2H), 7.36 (m, 2H), 6.27 (s, 2H), 5.48 (s, 2H), 4.50 (s, 2H), 3.55 (m, 14H), 2.64 (t, 2H, J=5.5 Hz). ESI/MS: 447 $[M+H]^+$.

Example 21

$O^6$-Benzylguanine-PEG-amino-α-azido-ε-N-Fmoc-lysine 50

$O^6$-Benzylguanine-PEG-amine 49 (76 mg, 0.17 mmol) and α-azido-ε-N-Fmoc-lysine 48 (67.2 mg, 0.17 mmol) are dissolved in 0.8 mL dry DMF, and 1-hydroxybenzotriazole (HOBT) (380 µL, 0.38 mmol, 1 M in 1-methyl-2-pyrrolidone (NMP)) is added. The mixture is stirred at 40° C. for 2 h and transferred into 25 mL of diethyl ether to precipitate the crude product. The residue is dissolved in methanol, adsorbed on $SiO_2$ (0.2 g) and purified by flash column chromatography (dichloromethane/methanol 10:1) to obtain the $O^6$-benzylguanine-PEG-amino-α-azido-ε-N-Fmoc-lysine 50 as a pale yellow oil (81 mg, 0.098 mmol, 57%). ESI-MS (m/z) 823.3 $[M+H]^+$ (MW calcd.=822.9).

Example 22

$O^6$-Benzylguanine-PEG-amino-ε-N-Fmoc-lysine 51

$O^6$-Benzylguanine-PEG-amino-α-azido-ε-N-Fmoc-lysine 50 (81 mg, 0.098 mmol) is dissolved in 400 µL 1,4- dioxane/100 µL water, and 590 µL trimethylphosphine (1 M in THF) are added. After stirring at room temperature for 2 h, the product is precipitated in 20 mL of diethyl ether and dried in vacuo over night. ESI-MS (m/z) 797.35 [M+H]$^+$ (MW calcd.=796.9). The product is used without further purification.

Example 23

$O^6$-Benzylguanine-PEG-amino-α-N-(biotinyl-6-aminocaproyl-εN-Fmoc-lysine 52

$O^6$-Benzylguanine-PEG-amino-ε-N-Fmoc-lysine 51 (78.4 mg, 0.098 mmol) and 30 µL triethylamine are dissolved in 0.5 mL DMF. N—(+)-Biotin-6-aminocaproic acid N-succinimidyl ester (49.2 mg, 0.1 mmol) is dissolved in 0.5 mL DMF, and both solutions are combined and stirred at 40° C. for 2 h. The reaction mixture is transferred into 30 mL of diethyl ether to precipitate the crude product. The residue is dissolved in methanol, adsorbed on $SiO_2$ (0.2 g) and purified by flash column chromatography (dichloromethane/methanol 10:1) to yield 80 mg (0.07 mmol, 71%) of a colorless solid. ESI-MS (m/z) 1136.38 [M+H]$^+$ (MW calcd.=1135.38).

Example 24

$O^6$-Benzylguanine-PEG-amino-α-N-(biotinyl-6-aminocaproyl)-lysine 53

$O^6$-Benzylguanine-PEG-amino-α-N-(biotinyl-6-aminocaproyl)-ε-N-Fmoc-lysine 52 (16 mg, 0.014 mmol) and 50 µL diethylamine are dissolved in 0.4 mL DMF and stirred at room temperature for 1 h. The product is precipitated with 20 mL diethyl ether and dried in vacuo. ESI-MS (m/z) 914.38 [M+H]+ (MW calcd.=914.13). The product is used for the next step without further purification.

Example 25

$O^6$-Benzylguanine-PEG-amino-α-N-(biotinyl-6-aminocaproyl)-ε-N-([digoxigenin-3-oxymethylcarbonyl]-6-aminocaproyl)-lysine 54

To a solution of $O^6$-benzylguanine-PEG-amino-α-N-biotinyl-6-aminocaproyly)-lysine 53 (6.93 mg, 0.0075 mmol) and 10 µL triethylamine in 0.4 mL dry DMF, (digoxygenin-3-oxymethyl-carbonyl)-6-aminocaproic acid N-hydroxysuccinimide ester (5 mg, 0.0075 mmol) is added, and the reaction mixture stirred at 40° C. for 2 h. The product is precipitated with 20 mL diethyl ether, dried in vacuo and purified via flash column chromatography using a gradient of 5 to 15% methanol in chloroform to yield 5 mg (0.0034 mmol, 45%) of the title product. ESI-MS (m/z) 1458.78 [M+H]$^+$ (MW calcd.=1457.82).

Example 26

$O^6$-Benzylguanine-PEG-amino-α-N-Fmoc-ε-N-Dde-lysine 56

$O^6$-Benzylguanine-PEG-amine 49 (50 mg, 0.11 mmol) and α-N-Fmoc-ε-N-Dde-lysine 55 (58 mg, 0.11 mmol) are dissolved in DMF (600 µL). HOBT (280 µL of a 1 M solution in NMP, 0.28 mmol) and 1-ethyl-3-(3-dimethylaminopropyl) carbodiimide (EDC, 54 mg, 0.28 mmol) are added, and the reaction is stirred for 1 h at room temperature. Ethyl ether is added to the solution to precipitate the product, and the supernatant is removed via pipette. Residual solvent is evaporated in vacuo. The product is purified by column chromatography on silica gel with a gradient of 2 to 5% methanol in dichloromethane (yield: 64%).

Example 27

$O^6$-Benzylguanine-PEG-amino-ε-N-Dde-lysine 57

$O^6$-Benzylguanine-PEG-amino-α-N-Fmoc-ε-N-Dde-lysine 56 (66 mg, 68.6 µmol) is dissolved in DMF (600 µL), and diethylamine (71 µL, 686 µmol) is added. The reaction mixture is stirred for 1 h at room temperature, and the solvent removed in vacuo. The product is used for the next step without further purification.

Example 28

$O^6$-Benzylguanine-PEG-amino-α-N-(biotinyl-6-aminocaproyl)-ε-N-Dde-lysine 58

$O^6$-Benzylguanine-PEG-amino-ε-N-Dde-lysine 57 and N—(+)-biotinyl-6-aminocaproic acid N-succinimidyl ester (31 mg, 68.6 µmol) are dissolved in DMF (700 µL). Triethylamine (30 µL) is added, and the reaction stirred for 2 h. Diethyl ether is added to the solution to precipitate the product, and the supernatant is removed via pipette. Residual solvent is evaporated in vacuo. Purification of the product is achieved by column chromatography on silica gel (gradient of 2 to 3% methanol in chloroform; yield: 37% over 2 steps).

Example 29

$O^6$-Benzylguanine-PEG-amino-α-N-(biotinyl-6-aminocaproyl)-lysine 53

$O^6$-Benzylguanine-PEG-amino-α-N-(biotinyl-aminocaproyl)-ε-N-Dde-lysine 58 (27 mg, 25.0 µmol) is stirred for 20 min in a solution of 2% hydrazine in DMF (250 µL). Acetone is added to the reaction mixture, and the mixture stirred for another 3 min. Ethyl ether is added to the solution to precipitate the product, and the supernatant is removed via pipette. Residual solvent is evaporated in vacuo. The product is used for the preparation of benzylguanine-PEG-amino-α-N-(biotinyl-6-aminocaproyl)-ε-N-([digoxigenin-3-oxymethyl-carbonyl]6-aminocaproyl)lysine 54 according to Example 24 without further purification (yield: 40% over 2 steps).

Example 30

$O^6$-Benzylguanine-PEG-amino-α-N-4-biotinyl-6-aminocaproyl)-ε-N-(2,4-dinitrobenzoyl)lysine 59

$O^6$-Benzylguanine-PEG-amino-α-N-(biotinyl-6-aminocaproyl)-lysine 53 (16.9 mg, 18.5 µmol) is dissolved in DMF (400 µL), and 2,4-dinitrofluorbenzene (4.1 mg, 22 µmol) and triethylamine (40 µL) are added. The reaction mixture is stirred at 45° C. for 2 h. Residual solvent is evaporated in vacuo. The product is purified via flash column chromatography on silica gel using a stepwise gradient of 0 to 15% methanol in chloroform (yield: 15 mg, 75%).

Example 31

$O^6$-Benzylguanine-PEG-amino-α-N-(biotinyl-6-aminocaproyl)-ε-N-(6-[fluorescein-5-carbonyl]-aminocaproyl)-lysine 60

$O^6$-Benzylguanine-PEG-amino-α-N-(biotinyl-6-aminocaproyl)-lysine 53 (8.5 mg, 0.93 µmol) and 6-(fluorescein-5-carbonylaminocaproic acid N-hydroxysuccinimidyl ester together with triethylamine (10 µL) are stirred in 200 µL dimethylacetamide at 40° C. for 4 h. The product is precipitated in 8 mL diethyl ether and dried in vacuo. ESI-MS (m/z) 1385.38 [M+H]$^+$ (MW calcd.=1385.13).

Example 32

Bis-N,N'-(O$^6$-benzylguanine-PEG)-urea 61

Triethylamine (15 µl) is added to a solution of O$^6$-[4-(13-amino-2,5,8,11-tetraoxatridecyl)benzyl]-guanine (49, 30 mg, 67 µmol) and N,N'-disuccinimidylcarbonat (8.6 mg, 33 µmol) in 0.8 ml dry DMF, and the reaction mixture stirred at room temperature for 24 h. The crude product is precipitated in diethyl ether (10 ml), adsorbed on SiO$_2$ and purified by flash column chromatography (methane/dichloromethane 5:1). Yield: 8.5 mg (9.2 µmol, 27%). ESI/MS: 919.78 [M+H]$^+$, (MW calc.=918.99).

Example 33

1-(tert-Butyldimethylsilyloxy)but-2-yn-4-ol (63)

tert-Butyldimethylsilyl chloride (8.0 g, 53 mmol) is dissolved in dry dichloromethane, and added dropwise to a solution of 2-butyne-1,4-ol (13.71 g, 159.2 mmol, 3 equ., 4-dimethyl-aminopyridine (1.29 g, 10.6 mmol, 0.2 equ.) and triethylamine (6.9 mL) in a solvent mixture of dichloromethane (200 mL) and THF (100 mL). The reaction mixture is stirred at room temperature for 15 h, washed with water and saturated ammonium chloride and dried over MgSO$_4$. Flash column chromatography (petrol ether/ethyl acetate 1:1) yields 7.2 g (67%).

Example 34

1-(tert-Butyldimethylsilyloxy)-4-iodobut-2-yne (64)

1-(tert-Butyldimethylsilyloxy)-but-2-yn-4-ol (63, 4.0 g, 19.96 mmol), imidazole (1.80 g, 26.45 mmol), iodine (6.58 g, 25.95 mmol) and triphenylphosphine (6.80 g, 25.95 mmol) are treated in 100 ml dichloromethane according to J. Robertson et al. J. Chem. Soc., Perkin Trans. 1, 3389-3369, 2000. Work-up yields 4.42 g (71%) of a colourless oil. The product is used directly in the next step.

Example 35

4-(11-Azido-3,6,9-trioxaundecyloxy)-1-(tert-butyldimethylsilyloxy-2-butyne (65)

11-Azido-3,6,9-trioxaundecanol (7, 3.79 g, 17.02 mmol) is dissolved in dry THF, and sodium hydride (1.02 g, 42.45 mmol) is added in small portions. After stirring at room temperature for 40 min, 1-tert-butyldimethylsilyloxy)-4-iodobut-2-yne (64, 4.4 g, 14.18 mmol) is added, and the reaction mixture stirred for additional 15 h. The reaction is quenched with water, and the amount of solvent reduced in vacuo to about 30%. Diethyl ether (50 mL) is added, the mixture washed with water, and the organic phase dried over MgSO$_4$. After evaporation of the solvent, the product is purified by flash column chromatography (petrol ether/ethyl acetate 4:1) to yield 3.12 g (54%).

Example 36

(13-Azido-2,5,8,11-tetraoxatridecyl)-propargyl alcohol (66)

Tert-butyldimethylsilyl ether 65 (1.5 g, 3.37 mmol) is dissolved in 25 mL THF with 0.25 mL acetic acid, and treated with tetrabutylammonium fluoride (4.1 mL, 1 M in THF). The reaction mixture is stirred for 2 h, and the amount of solvent reduced in vacuo to about 30%. After addition of ethyl acetate (50 mL), the organic phase is washed with sat. sodium bicarbonate (20 mL) and brine (30 mL), and dried over MgSO$_4$. The product is used in the next step without further purification. Yield: 0.774 g (80%).

Example 37

O$^6$-[(13-Azido-2,5,8,11-tetraoxatridecyl)-propargyl]-guanine (67)

Propargyl alcohol 66 (724 mg, 2.5 mmol) is dissolved in dry DMF (1 mL), and sodium hydride (181 mg, 7.55 mmol) is added in two portions. After stirring at room temperature for 30 min, 1-(2-amino-7H-purin-6-yl)-1-methyl-pyrrolidinium chloride (27, 641 mg, 2.5 mmol) and 4-dimethylaminopyridine (100 mg, 0.81 mmol) are added. Stirring is continued for 15 h, and the product precipitated by the addition of 30 mL diethyl ether. Flash column chromatography (dichloromethane/methanol 95:5) yields 470 mg (44%) of a slightly yellow oil. ESI/MS: 421.29 [M+H]$^+$.

Example 38

O$^6$-[(13-Amino-2,5,8,11-tetraoxatridecyl)-propargyl]-guanine (68)

Azide 67 (400 mg, 0.951 mmol) and triphenylphosphine (748 mg, 2.85 mmol) are stirred at room temperature for 15 h in a solvent mixture of 6 mL 1,4-dioxane/400 µL water. The solvent is removed in vacuo, and the residue purified via flash column chromatography (dichloromethane/methanol 10:1) yielding 312 mg (83%).

Example 39

O$^6$-[(13-(Biotinyl-6-aminocaproyl-amino)-2,5,8,11-tetraoxatridecyl)-propargyl]-guanine (69)

Propargyl guanine 68 (26.9 mg, 88 µmol) and (+)-biotinyl-6-aminohexanoic acid N-hydroxy-succinimide ester (20.0 mg, 44 µmol) are stirred with 15 µL triethylamine in 1 mL DMF at 40° C. for 3 h. The solvent is removed in vacuo, and the residue purified via flash column chromatography (dichloromethane/methanol 10:1) yielding 20 mg (68%).

Example 40

O$^6$-[(13-(Digoxigenin-3-oxymethylcarbonyl-6-aminocaproyl-amino)-2,5,8,11-tetraoxatridecyl)-propargyl]-guanine 70

Propargyl guanine 68 (11.6 mg, 37 µmol), digoxygenin-3-oxymethylcarbonyl-6-aminocaproic acid N-hydroxysuccinimide ester (5 mg, 7.5 µmol) and 10 µL triethylamine are stirred at 40° C. for 2 h. The product is precipitated with 20 mL diethyl ether, dried in vacuo and purified via flash column chromatography using a gradient of 5 to 15% methanol in chloroform to yield 3.2 mg of the title compound (0.0034 mmol, 45%). ESI-MS (m/z) 939.78 [M+H]$^+$ (MW calcd.=938.12).

Example 41

O$^6$-[4-(12-Fmoc-amino-dodecanoyl)aminomethyl] benzyl guanine 72

12-Fmoc-aminododecanoic acid (147 mg, 0.33 mmol) and 1-benzotriazolyloxy-tris-pyrrolidino-phosphonium hexafluorophosphate (PyBOP, 193 mg, 0.37 mmol) are dissolved in 11 ml DMF. After stirring at room temperature for 45 min O$^6$ aminomethyl-benzyl guanine (71, 100 mg, 0.37 mmol) in 5 mL DMF are added. The reaction mixture is stirred at 50° C. for 5 min, then at room temperature for 1 h. After evaporation of the solvent in vacuo the product is purified by flash column chromatography (gradient methanol/dichloromethane from 1:50 to 1:10) to yield 185 mg (0.27 mmol, 79%) of white solid product. $R_f$=0.33 (methanol/dichloromethane 1:10). $^1$H NMR (400 MHz, DMSO-$d_6$): δ 1.16-1.50 (m, 16H), 2.11 (t, J=7 Hz, 2H), 2.95 (m, 2H), 2.96-3.09 (m, 2H), 3.58 (m, 1H) 4.20-4.28 (m, 5H), 5.45 (s, 2H), 6.28 (s, 2H), 7.26-7.88 (m, 12H), 8.30 (t, J=6 Hz, 1H). CI-MS 468 [(M-Fmoc)+H]$^+$ (MW calcd.=689.9).

Example 42

$O^6$-[4-(12-Aminododecanoyl)-aminomethyl]-benzyl guanine (73)

Fmoc-protected derivative 72 (180 mg, 0.26 mmol) is dissolved in 3.2 mL DMF containing 20% (v/v, 6.5 mmol) piperidine. After stirring at room temperature for 30 min the solvent is removed in vacuo and the product purified by flash column chromatography (gradient: methanol/dichloromethane from 1:20 to 1:5 containing 1% triethylamine) to obtain 95 mg (0.20 mmol, 78%) of a pale yellow solid. $R_f$=0.05 (methanol/triethylamine/dichloromethane 20:1:100). $^1$H NMR (400 MHz, DMSO-$d_6$): δ 1.23-1.50 (m, 18H), 2.11 (t, J=7 Hz, 2H), 2.58 (t, J=7 Hz, 2H), 4.24 (d, J=6 Hz, 2H), 5.45 (s, 2H), 6.27 (s, 2H), 7.35 (dd, J=8 Hz, 77 Hz, 4H), 7.82 (s, 1H), 8.29 (t, J=6 Hz, 1H). ESI-MS (m/z) 468.8 [M+H]$^+$ (MW calcd.=467.6).

Example 43

L-2-{4-[N-(2,4-Diamino-6-pteridinylmethyl)-methylamino]-benzoylamino}-pentanedioic acid 1-benzyl ester (76)

L-Glutamic acid 1-benzylester (75, 114 mg, 0.48 mmol) and $K_2CO_3$ (66.4 mg, 0.48 mmol) are added to 3 mL DMSO and sonicated at 60° C. for 1 h. This mixture is added to a solution of 4-(N-[2,4-diamino-6-pteridinylmethyl]-methylaminoybenzoic acid 74 (150 mg, 0.46 mmol), diisopropylethylamine (112 µL, 0.65 mmol) and PYBOP (250 mg, 0.48 mmol) in 1.3 ml DMSO which had been stirred for 1 h. The reaction mixture is stirred at 50° C. for 10 min and then at room temperature for 2.5 h. After quenching with 0.5 mL 1 M triethylamine the crude product is purified by HPLC with a linear gradient water/0.1% trifluoracetic acid (TFA): acetonitrile/0.08% TFA from 100:0 to 20:80. The solution is adjusted to pH 7, and the solvents are removed in vacuo to yield 50 mg (0.09 mmol, 20%) of an orange solid. $^1$H NMR (400 MHz, DMSO-$d_6$): δ 1.90-2.05 (m, 2H), 2.30 (m, 2H), 2.78 (m, 1H) 3.21 (d, J=3 Hz, 3H), 3.28 (m, 1H), 4.78 (s, 2H), 5.11 (s, 2H), 6.62 (broad s, 2H), 6.81-7.72 (m, 9H), 8.57 (m, 1H). ESI-MS (m/z) 545.4 [M+H]$^+$ (MW calcd.=544.6).

Example 44

$O^6$-4-([12-N-(4-{4-[N-(2,4-Diamino-6-pteridinylmethyl)-methylamino]-benzoyl-amino}-4-benzyloxycarbonylbutanoyl)-aminododecanoyl]-aminomethyl)-benzyl guanine (77)

(Benzotriazol-1-yloxy)tri-pyrrolidino-phosphonium hexafluorophosphate (PyBOP, 152 mg, 0.29 mmol) is dissolved in a solution of 1-hydroxybenzotriazole (HOBT) (146 µL of 1 M solution in 1-methyl-2-pyrrolidone (NMP), 0.15 mmol) and added to benzyl ester 76 (380 µL of 0.154 M solution in NMP, 0.06 mmol). The mixture is shaken for 30 min and then added to amino-guanine 73 (27.2 mg, 0.06 mmol) in 200 µL NMP and diisopropylethylamine (30 µL, 0.18 mmol). The reaction mixture is stirred at room temperature for 2 h and then quenched with 200 µL 1 M TFA. After removal of the solvent in vacuo, the product is purified by flash column chromatography (gradient methanol/dichloromethane, from 1:50 to 1:5, containing 2% acetic acid). 19 mg (0.2 mmol, 33%) of an orange solid are obtained. $R_f$=0.08 (methanol/acetic acid/dichloromethane 5:1:50). ESI-MS (m/z) 994.9 [M+H]$^+$ (MW calcd.=994.2).

Example 45

$O^6$-4-([12-N-(4-{4-[N-(2,4-Diamino-6-pteridinylmethyl)-methylamino]-benzoyl-amino}-4-carboxybutanoyl-aminododecanoyl]-aminomethyl)-benzyl guanine (78)

Benzyl ester 77 (13 mg, 0.01 mmol) is dissolved in 2 mL methanol/water 1:1, and $K_2CO_3$ (785 µL 1 M in methanol/water 1:1, 0.79 mmol) is added. The mixture is shaken at room temperature for 2.5 h followed by quenching with 785 µL of 1 M TFA. The crude product is purified by HPLC with a linear gradient water/0.1% TFA: acetonitrile/0.08% TFA from 100:0 to 20:80.10 mg (0.01 mmol, 85%) product are obtained. ESI-MS (m/z) 904.7 [M+H]$^+$ (MW calcd.=904.0).

Example 46

$O^6$-4-[13-N-(4-{4-[N-(2,4-Diamino-6-pteridinylmethyl)-methylamino]-benzoyl-amino}-4-carboxybutanoyl)-amino-2,5,8,11-tetraoxatridecyl]-benzyl guanine (79)

PyBOP (201 mg, 0.39 mmol) and HOBT (194 µl of a 1 M solution in NMP, 0.19 mmol) are added to benzyl ester 76 (21 mg, 0.04 mmol), and the mixture shaken at room temperature for 30 min. $O^6$-[4-(13-Amino-2,5,8,11-tetraoxatridecylybenzyl guanine (49, 21 mg, 0.05 mmol) and diisopropylethylamine (24 µL, 0.14 mmol) are dissolved in 490 µL NMP and added to the solution of activated 76. After shaking at room temperature for 3 h the reaction mixture is quenched with 1 mL acetonitrile/2 mL 1 M TFA, and the crude product purified by HPLC using a linear gradient water/0.1% TFA: acetonitrile/0.08% TFA from 100:0 to 20:80. Deprotection of the carboxy group is achieved by adjusting the pH of the solution to 10 with 1.5 M NaOH. After purification of the crude product by HPLC using the same gradient as in the previous step, 14 mg (0.02 mmol, 40%) of the title compound are obtained. ESI-MS (m/z) 883.4 [M+H]$^+$ (MW calcd.=882.9).

Example 47

4-Allyloxymethyl-1-(tert-butyldimethylsilyloxymethyl)-benzene (80)

To a solution of 4-tert-butyldimethylsilyloxymethyl)benzyl alcohol 44 (2.85 g, 11.31 mmol) in 15 mL dry THF, sodium hydride (326 mg, 13.57 mmol) is added in small portions under an argon atmosphere, and the reaction mixture stirred at room temperature for 30 min. A solution of allyl iodide (3.80 g, 22.62 mmol) in 5 mL dry THF is added, and the resulting mixture stirred for 17 h. The reaction is quenched with water, the solvent reduced to about 30% of its volume, and the residue extracted with ethyl acetate (3 times 20 mL). The organic phase is dried over MgSO$_4$, the solvent removed in vacuo, and the product purified by flash column chromatography (petrol ether/ethyl acetate 100:1), yield 1.83 g (6.25 mmol, 59%).

Example 48

1,4-Di-[4-(tert-butyldimethylsilyloxymethyl)-benzyloxy]-2-butene (81)

Benzylidene-bis(tricyclohexylphosphine)-dichlororuthenium (420 mg, 0.513 mmol, 15 mol %) is added under an argon atmosphere to a solution of 4-allyloxymethyl-1-tert-butyldimethylsilyloxymethyl)-benzene (80, 1.0 g, 3.24 mmol) in 70 mL dry dichloromethane. The reaction mixture is stirred at room temperature for 15 h, and additional catalyst (200 mg) is added and the reaction mixture heated to reflux for 5 h. The solvent is removed in vacuo, and the product purified by column chromatography (petrol ether/ethyl acetate 50:1) to yield 520 mg (0.93 mmol, 55%) of the title compound.

Example 49

Bis-1,4-(O$^6$-benzylguanine-methoxy)-2-butene 82

TBDMS-dimer 81 (351 mg, 0.63 mmol) is dissolved in 5 mL dry THF, and tetrabutylammonium fluoride (3.78 mmol) and acetic acid (3.78 mmol) are added. The reaction mixture is stirred at room temperature for 15 h. After evaporation of the solvent, the product is purified by column chromatography using a solvent gradient (petrol ether /ethyl acetate 1:1 to 1:3) to yield 150 mg (0.45 mmol, 73%) of a colourless solid. To a solution of this deprotected dimer (100 mg, 0.30 mmol) in 0.8 mL dry DMF, sodium hydride (44 mg, 1.82 mmol) is added, and the reaction mixture stirred for 30 min. 1-(2-Amino-7H-purin-6-yl)-1-methyl-pyrrolidinium chloride (27, 186 mg, 0.73 mmol) and DMAP (11 mg, 0.09 mmol) are added, and the reaction mixture stirred at room temperature for additional 3 h. The reaction is quenched with water and the solvent removed in vacuo. The residue is dissolved in methanol, adsorbed on SiO$_2$ and purified by flash column chromatography (dichloromethane/methanol 10:1) to obtain dimer 82 as a colourless solid (30 mg, 0.05 mmol, 16%).

Example 50

11-Allyloxy-3,6,9-trioxaundecanol (83)

To an anhydrous solution of potassium tert-butoxide (2.3 g, 19.5 mmol) in THF (500 mL), tetraethylene glycol (7.18 g, 37.0 mmol) is added at room temperature. The resulting mixture is stirred for 30 min, and a solution of allyl iodide (3.31 g, 19.7 mmol) in dry THF (60 mL) is added dropwise over 1 h. The reaction mixture is stirred for 30 h and filtered through a silica plug (10 g) using ethyl acetate (800 mL) to elute all product. After evaporation of the solvent in vacuo, the product is purified by column chromatography using a solvent gradient petrol ether/ethyl acetate 10:1 to ethyl acetate 100% yielding a colourless oil (2.41 g, 10.3 mmol, 27%).

Example 51

1-(tert-Butyldimethylsilyloxymethyl)-4-(13-allyloxy-2,5,8,11-tetraoxa-tridecyl)-benzene (84)

To a solution of 11-allyloxy-3,6,9-trioxaundecanol (83, 2.33 g, 9.94 mmol) in dry THF (40 mL), sodium hydride (0.95 g, 39.8 mmol) is added in several portions under an argon atmosphere. The mixture is stirred for 30 min. A solution of the iodo derivative 45 (3.0 g, 8.28 mmol) in dry THF (10 mL) is added dropwise, and the mixture stirred for 15 h. The reaction is quenched by adding 2 mL of water, and 70% of the amount of THF is evaporated in vacuo. To dilute the mixture, 70 mL of water are added, and the solution extracted with 5 times 50 mL ethyl acetate. The combined organic extracts are dried over MgSO$_4$ and concentrated in vacuo. The yellow oil obtained is purified by flash column chromatography (gradient petrol ether/ethyl acetate 10:1 to 5:1) to give the title product 84 as a pale yellow oil (1.96 g, 4.2 mmol, 51%).

Example 52

TBDMS Protected Bis-1,4-(benzyl alcohol-PEG)-2-butene 85

Benzylidene-bis(tricyclohexylphosphine)-dichlororuthenium (263 mg, 0.32 mmol, 15 mol %) is added under an argon atmosphere to a solution of TBDMS protected allyloxy derivative 84 (1.0 g, 2.13 mmol) in 40 mL dry dichloromethane. The reaction mixture is heated to reflux for 5 h. Additional catalyst (200 mg) is added and heating continued for 15 h. The solvent is removed in vacuo, and the product purified by column chromatography using a solvent gradient petrol ether/ethyl acetate 1:1 to 1:5, to yield 530 mg (0.58 mmol, 54%) of dimer 85.

Example 53

Bis-1,4-(O$^6$-benzylguanine-PEG)-2-butene 86

TBDMS protected dimer 85 (200 mg, 0.22 mmol) is dissolved in 3 mL dry THF, and tetrabutylammonium fluoride (2.5 mmol) and acetic acid (2.5 mmol) are added. The reaction mixture is stirred at room temperature for 15 h. After evaporation of the solvent, the product is purified by column chromatography using a solvent gradient petrol ether/ethyl acetate 1:1 to ethyl acetate 100% to yield 80 mg (0.11 mmol, 50%) of a colourless solid. To a solution of this deprotected dimer (61 mg, 0.089 mmol), 1-(2-amino-7H-purin-6-yl)-1-methyl-pyrrolidinium chloride (27, 54 mg, 0.22 mmol) and DMAP (3.0 mg, 0.027 mmol) in 1.0 mL dry DMF, sodium hydride (13 mg, 0.54 mmol) is added, and the reaction mixture stirred for 2 h. The reaction is quenched with water, and the solvent removed in vacuo. The residue is dissolved in methanol, adsorbed on SiO$_2$ and purified by flash column chromatography (dichloromethane/methanol 10:1) to obtain dimer 86 as a colourless solid (35 mg, 0.036 mmol, 41%).

Example 54

Demonstration of Reactivity of Compounds of Formula 1 with Human O$^6$-alkylguanine-DNA Alkyltransferase (hAGT) Fusion Proteins a) Reactivity of O$^6$-(1-[11-amino-3,6,9-trioxaundecyl]-1,2,3-triazolyl-4-methyl)guanine (11)

Figure 1:
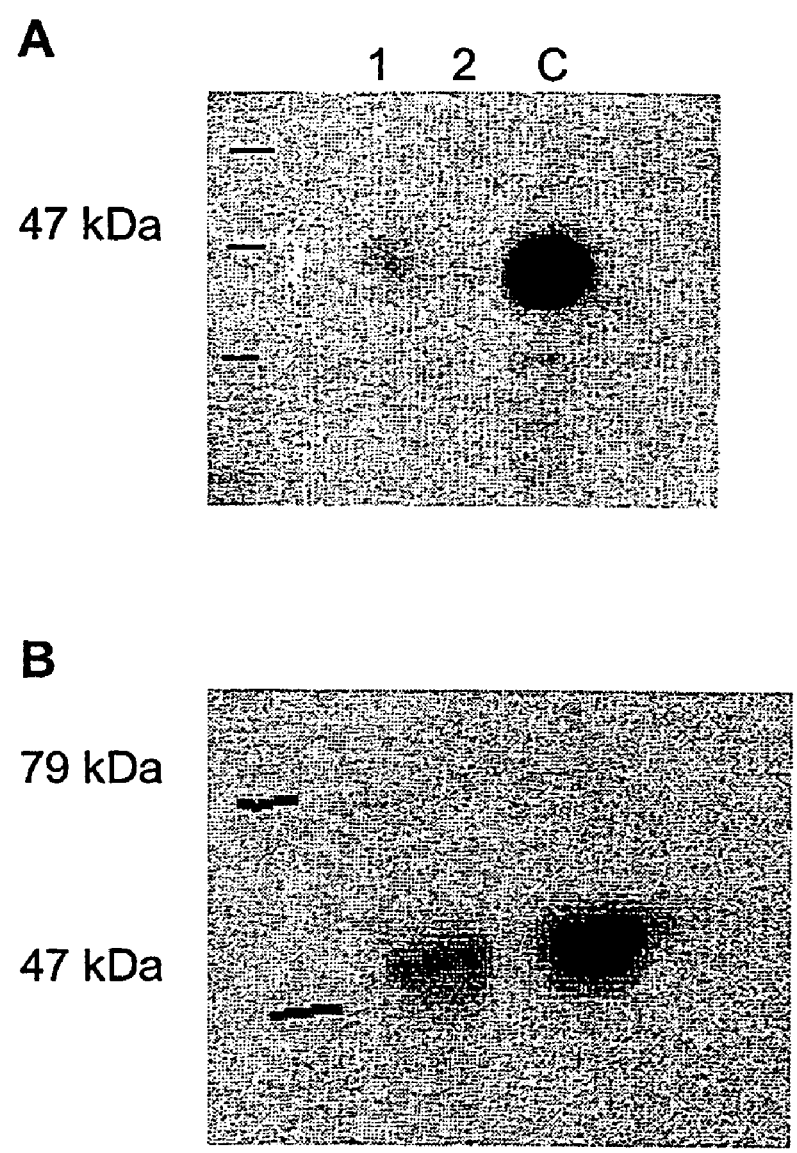
FIG. 1A: Western Blot of an anti-biotin conjugate coupled to HRP (Pierce). Lanes 1 and 2: $^{PGE4}$hAGT-GST (an AGT fusion protein) after reaction with compound 11 (a compound of formula 1 wherein $R_3$ is triazolylmethyl) and then with a biotinylated $O^6$-benzylguanine oligonucleotide known to be an AGT substrate. Lane marked "C" (control): The reaction product of $^{PGE4}$hAGT-GST and the biotinylated $O^6$-benzylguanine oligonucleotide.
FIG. 1B: Western Blot of a goat anti-fluorescein antibody (Rockland) and a HRP conjugated anti-goat antibody (Sigma).

18 pmol $^{PGEA}$hAGT-GST (A. Juillerat et al., Chem. Biol. 10: 313-317, 2003) are incubated with 0.2 µL of a 5 mM solution of 11 in DMSO in a total volume of 15 µL of 50 mM HEPES pH 7.5 for 1 h. 10 pmol of a biotinylated O$^6$-benzylguanine-oligonucleotide (R. Damoiseaux et al., ChemBiochem 4: 285-287, 2001) is added, and the reaction is allowed to continue for further 15 min. As a control 18 pmol $^{PGEA}$hAGT-GST are incubated with 10 pmol of the same biotinylated oligonucleotide in a total volume of 15 µL of 50 mM HEPES pH 7.5 for 15 min without any substrate. Detection of the biotinylated reaction product between $^{PGEA}$hAGT-GST and the biotinylated oligonucleotide is performed by Western Blotting using an anti-biotin conjugate coupled to HRP (Pierce). Lane "C" of FIG. 1A shows the reaction product of $^{PGEA}$hAGT-GST with the biotinylated oligonucleotide. If $^{PGEA}$hAGT-GST is first reacted with 11, no further reaction with biotinylated oligonucleotide is observed (lanes 1 and 2, FIG. 1A). This proves that $O^6$-triazolylmethylguanines are efficient substrates for hAGT.

b) Reactivity of $O^6$-benzylguanine-PEG-amino-α-N-(biotinyl-6-aminocaproyl)-ε-N-6-[fluorescein-5-carbonyl]-aminocaproyl)-lysine 60

18 pmol $^{PGEA}$hAGT-GST are incubated with 0.5 nmol 60 in a total volume of 15 μL of 50 mM HEPES pH 7.5. The reaction product is detected by Western Blotting using a goat anti-fluorescein antibody (Rockland) and a HRP conjugated anti-goat antibody (Sigma). This proves that compound 60 containing two different labels is an efficient substrate for hAGT.

Example 55

Immobilization of a Human $O^6$-alkylguanine-DNA Alkyltransferase (hAGT) Fusion Protein on a Solid Phase 80 μL of a solution of $^{PGEA}$hAGT-GST fusion protein (200 μg/mL in HBS buffer) are incubated with 20 μL of a 0.4 mM solution of $O^6$-benzylguanine-PEG-amino-α-N-(biotinyl-6-amino-caproyl)-ε-N-([digoxigenin-3-oxymethylcarbonyl]-6-aminocaproyl)-lysine 54 for 10 min at room temperature. This solution is passed over a Neutravidin Biacore chip for 35 min at a flow rate of 1 μL/min. The chip is then purged with buffer (HBST) for 40 min at the same flow rate. Subsequently, a solution of αGST-antibody (1980 μg/mL) is injected to further elucidate the previous binding of the fusion protein, followed again by washing with HBST. Immobilization experiments are measured by surface plasmon resonance. Surface plasmon resonance analysis is performed using a Biacore 1000 optical biosensor equipped with research grade SA sensor chips (Biacore). EDTA-free HBS (10 mM HEPES, pH 7.4, 150 mM NaCl, 0.005% Tween 20) is freshly prepared and filtered through a 22 μm membrane. The resulting sensogram is shown in FIG. 2.

Example 56

Dimerization of a Human $O^6$-alkylguanine-DNA Alkyltransferase (hAGT)

a) Reaction of $^{PGEG}$hAGT with the Dimerizing Substrate 43:
Dimerizaton experiments are performed in a total volume of 40 μL at a constant concentration of $^{PGEG}$hAGT-GST (A. Juillerat et al., Chem. Biol. 10: 313-317, 2003) of 0.4 μM in HEPES-buffer (HEPES 50 mM, pH 7.2, 1 mM DTT, 200 μg/mL BSA). The concentration of compound 43 is varied to cover a ratio of substrate to protein from 0 to 100:1. Incubation time is 40 min for all experiments. Western Blots are obtained using an anti-hAGT antibody (1:2000, in PBS, Chemicon) and an anti-mouse-HRP conjugate (1:2000 in PBS, Sigma) as a second antibody. The result is shown in FIG. 3A.

b) Reaction of HA-$^{W160}$hAGT with the Dimerizing Substrate 61 in *E. coli* Extracts
Experiments are performed with the hAGT mutant Gly160Trp ($^{W160}$hAGT) (M. Xu-Welliver et al., Biochemical Pharmacology 58: 1279-1285, 1999). HA-$^{W160}$hAGT is expressed in *E. coli* BL21 in LB medium at 24° C. for 2 h after addition of IPTG (1 mM) and substrate 61 in different concentrations (0, 10, 20, and 50 μM) to an exponentially growing culture. Cells are harvested by centrifugation. For each labelling experiment the total volume of extract is about 1 ml (volume adjusted to a constant $OD_{600}$). The pellets are resuspended in 50 μl 1×SDS followed by addition of $O^6$-benzylguanine to a concentration of 1 mM. After heating for 5 min to 95° C., samples are loaded to a 12% SDS-page. Western Blot is obtained using an goat anti-MGMT (1:100 in TBST, Chemicon) and an anti-goat IgG (1:1000 in TBST, Santa Cruz Biotechnology) as s second antibody. The result is shown in FIG. 3B.

Example 57

Reactivity of 78 and 79 Against GST-$^{3HY}$hAGT

To verify that $^{3HY}$hAGT possesses activity against 78 and 79, $^{3HY}$hAGT is expressed as fusion protein with glutathione S-transferase (GST-$^{3HY}$hAGT) in *E. coli*, the fusion protein purified and its activity determined in an in vitro assay. GST-$^{3HY}$hAGT is incubated with an excess of 78 or 79 and the reaction is followed by Western Blotting using an anti-methotrexate antibody. In this assay, GST-$^{3HY}$hAGT shows second-order rate constants of about 1500 sec$^{-1}$M$^{-1}$ for the reaction with 78 and 900 sec$^{-1}$M$^{-1}$ for the reaction with 79. Accordingly, at concentrations of 78 of 1 μM and at an excess of 78 over $^{3HY}$hAGT (pseudo first-order conditions), 50% of the protein is labelled in less than 10 min.

Example 58 hAGT Mutants

For the construction of hAGT fusion proteins, preferably the mutant Asn157Gly Ser159Glu is used. This mutant shows increased activity against benzylguanine derivatives of the type 1 by a factor of approximately 20 compared to wild-type hAGT, see A. Juillerat et al., Chem. Biol. 10: 313-317, 2003. The following additional mutations in hAGT have been shown to disrupt DNA binding of hAGT but do not significantly interfere with the activity against benzylguanine derivatives: Lys125Ala, Ala127Thr and Arg128Ala, see A. Lim et al., EMBO J. 15: 4050-4060, 1996, and D. S. Daniels et al., EMBO J. 19: 1719-1730, 2000. The rationale behind the introduction of these mutations is to minimize the interaction of hAGT fusion proteins with DNA in the three-hybrid system. The resulting hAGT mutant carrying the five mutations described above is abbreviated as $^{3HY}$hAGT.

Example 59

Growth Assay of Yeast L40 Strains

Pairs of plasmids encoding LexA-$^{3HY}$hAGT and B42-DHFR fusion proteins are transformed into the yeast strain L40 in which the reconstitution of functional LexA-B42 transcription factor leads to transcription of the reporter genes HIS3 and lacZ. It is tested if the expression of different combinations of fusion protein in the presence of either 78 or 79 complemented the histidine auxotrophy of the yeast L40 (Table 1). Co-expression of LexA-$^{3HY}$hAGT and B42-DHFR allows yeast L40 to grow on plates lacking histidine but containing either 78 or 79, indicating transcription of HIS3. No growth is observed in the absence of 78 or 79.

TABLE 1

Growth rates of different yeast L40 strains on plates lacking histidine and in the presence and absence of compounds 78 or 79.

| Protein pair | Benzyl guanine | Growth rate a) |
|---|---|---|
| LexA-$^{3HY}$hAGT/ B42-DHFR | 1 μM 78 | +++ |
| LexA-$^{3HY}$hAGT/ B42-DHFR | 10 μM 79 | +++ |
| LexA-$^{3HY}$hAGT/ B42-DHFR | — | — |
| LexA-DHFR/ B42-$^{3HY}$hAGT | 1 μM 78 | ++ |
| LexA-DHFR/ B42-$^{3HY}$hAGT | 10 μM 79 | ++ |
| LexA-DHFR/ B42-$^{3HY}$hAGT | — | — | a) +++: detection of colonies within 2 days; ++: detection of colonies within 3 days; +: detection of colonies within 5 days; —: no colonies within 7 days.

In principal, the reconstitution of functional transcription factor through benzyl guanine 78 and 79 is independent of which ligand-binding protein is fused to LexA and which to B42. To verify this assumption the growth of yeast L40 co-expressing LexA-DHFR and B42-$^{3HY}$hAGT on plates lacking histidine but containing compounds 78 or 79 is examined. As expected, growth dependent on compounds 78 or 79 is observed although the growth rates are below those observed for yeast co-expressing LexA-$^{3HY}$hAGT and B42-DHFR (Table 1).

Example 60

Quantitative β-galactosidase Assay using ONPG

The activation of transcription of the lacZ reporter gene by the benzyl guanine based compounds 78 and 79 in the yeast strain L40 expressing different combinations of LexA and B42 fusion proteins is examined (Table 2). In this assay, the activity of the product of the lacZ gene, β-galactosidase, is determined by measuring the hydrolysis rate of the chromogenic substrate o-nitrophenyl-β-D-galactopyranoside (ONPG) in cell extracts of liquid cultures.

TABLE 2

Quantitative β-galactosidase assay using ONPG.

| Protein pair | Benzyl guanine | ONPG hydrolysis a) |
|---|---|---|
| LexA-$^{3HY}$hAGT/ B42-DHFR | 1 μM 78 | 865 |
| LexA-$^{3HY}$hAGT/ B42-DHFR | 1 μM 79 | 63 |
| LexA-$^{3HY}$hAGT/ B42-DHFR | — | 4 |
| LexA-DHFR/ B42-$^{3HY}$hAGT | 1 μM 78 | 28 |
| LexA-DHFR/ B42-$^{3HY}$hAGT | 1 μM 79 | 24 |
| LexA-DHFR/ B42-$^{3HY}$hAGT | — | 3 | a) nM of o-nitrophenol formed per min per mg total protein

The invention claimed is:

1. A compound of formula 1

$$\begin{array}{c} R_4-L \\ | \\ CH_2-R_3 \\ | \\ X \\ | \\ R_1 \\ | \\ R_2 \end{array} \quad 1$$

wherein $R_1$-$R_2$ is a radical of formula 2

$$\text{(structure with } R_5, R_2, R_6 \text{ on purine ring with methyl)} \quad 2$$

wherein $R_2$ is hydrogen, alkyl of 1 to 10 carbon atoms, or a saccharide moiety;

$R_5$ is hydrogen, halogen, trifluoromethyl, or hydroxy; and $R_6$ is hydrogen, hydroxy or unsubstituted or substituted amino;

and tautomeric forms thereof;

X is oxygen or sulfur;

$R_3$ is triazolylene, tetrazolylene, isoxazolylene, thienylene, isoxazolidinylene, or alkynylene, wherein a double bond or the triple bond, respectively, is connected to $CH_2$ of formula 1;

$R_4$ is an optionally substituted straight or branched chain alkylene group or polyvalent branched chain alkyl group with 1 to 300 carbon atoms, wherein optionally (a) one or more carbon atoms are replaced by oxygen (b) one or more carbon atoms are replaced by nitrogen carrying a hydrogen atom, and a carbon atom adjacent to nitrogen is substituted by oxo;

(c) one or more carbon atoms are replaced by oxygen, and a carbon atom adjacent to oxygen is substituted by oxo;

(d) the bond between two adjacent carbon atoms is a double or a triple bond;

(e) one or more carbon atoms are replaced by a phenylene, a saturated or unsaturated cycloalkylene, a saturated or unsaturated bicycloalkylene, a bridging heteroaromatic or a bridging saturated or unsaturated heterocyclyl group; and/or (f) two adjacent carbon atoms are replaced by a disulfide linkage; and L is one or a plurality of same or different labels connected to $R_4$, selected from a spectroscopic probe selected from a fluorophore and a chromophore, a moiety selected from biotin, avidin and streptavidin, a moiety which is capable of generating hydroxyl radicals upon exposure to $H_2O_2$ and ascorbate, a moiety which is capable of generating reactive radicals upon irradiation with light, a moiety covalently attached to a solid support, a nucleic acid moiety or a derivative thereof capable of undergoing base-pairing with its complementary strand, a lipid moiety, and a methotrexate moiety attached via a primary carboxy group; or L is a bond connecting $R_4$ to $R_1$ forming a cyclic substrate; and or L is a further group —$R_3$—$CH_2$—X—$R_1$-$R_2$.

2. The compound of formula 1 according to claim 1, wherein the saccharide moiety $R_2$ is a β-D-2'-deoxyribosyl, or a β-D-2'-deoxyribosyl being incorporated into a single stranded oligodeoxyribonucleotide having a length of 2 to 99 nucleotides, wherein the radical of formula 2 occupies any position within the oligonucleotide sequence.

3. The compound of formula 1 according to claim 1, wherein $R_2$ is hydrogen, $R_5$ is hydrogen, $R_6$ is unsubstituted amino, and X is oxygen.

4. The compound of formula 1 according to claim 1, wherein $R_3$ is triazolylene, tetrazolylene, isoxazolylene, thienylene, or isoxazolidinylene.

5. The compound of formula 1 according to claim 4 wherein $R_3$ is triazolylene.

6. The compound of formula 1 according to claim 4 wherein $R_3$ is tetrazolylene.

7. The compound of formula 1 according to claim 4 wherein $R_3$ is isoxazolylene.

8. The compound of formula 1 according to claim 4 wherein $R_3$ is thienylene.

9. The compound of formula 1 according to claim 4 wherein $R_3$ is isoxazolidinylene.

10. The compound of formula 1 according to claim 1, wherein $R_3$ is 1-alkynylene.

11. The compound of formula 1 according to claim 1, wherein $R_4$ is a straight chain alkylene group with 2 to 25 carbon atoms, a straight chain polyethylene glycol group with 4 to 100 ethyleneoxy units, or a straight chain alkylene group with 2 to 25 carbon atoms wherein two or more carbon atoms are replaced by an amide function —NH—CO—, optionally attached to the group $R_3$ by a —CH=CH— or —C≡C— group.

12. The compound of formula 1 according to claim 1, wherein $R_4$ is a branched chain alkylene group comprising a polyethylene glycol group of 3 to 6 ethylene glycol units and one or more alkylene groups wherein carbon atoms are replaced by amide bonds, and further carrying substituted amino and hydroxy functions.

13. The compound of formula 1 according to claim 1, wherein $R_4$ is a branched chain alkylene group, wherein
  (a) one or more carbon atoms are replaced by oxygen, and
  (b) one or more carbon atoms are replaced by nitrogen carrying a hydrogen atom, and a carbon atom adjacent to nitrogen is substituted by oxo.

14. The compound of formula 1 according to claim 1, wherein L is a further group —$R_3$—$CH_2$—X—$R_1$-$R_2$.

15. The compound of formula 1 according to claim 1, wherein $R_4$ is a straight chain alkylene group of 10 to 40 carbon atoms wherein 3 to 12 carbon atoms are replaced by oxygen, one or two carbon atoms are replaced by 1,4-triazolidene units, and optionally one carbon atom is replaced by a 1,4-phenylene unit.

16. The compound of formula 1 according to claim 1, wherein $R_4$ is a straight chain alkylene group of 6 to 40 carbon atoms wherein 2 to 12 carbon atoms are replaced by oxygen and one or two bonds between two adjacent carbon atoms is a double bond.

17. The compound of formula 1 according to claim 1, wherein $R_6$ is amino and L is a bond connecting $R_4$ to $R_6$.

18. The compound of formula 1 according to claim 1, wherein L is a methotrexate moiety.

19. The compound of formula 1 according to claim 1, wherein L is a plurality of same or different labels.

20. The compound of formula 1 according to claim 19, wherein L is two different labels.

21. A compound of the formula 1

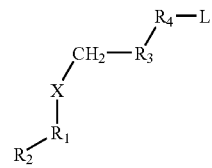

wherein $R_1$-$R_2$ is a radical of formula 2

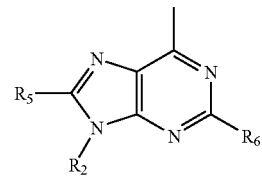

wherein $R_2$ is hydrogen, $R_5$ is hydrogen and $R_6$ is unsubstituted amino;

X is oxygen;

$R_3$ is triazolylene, tetrazolylene, isoxazolylene, thienylene, isoxazolidinylene or alkynylene, wherein a double bond or the triple bond, respectively, is connected to $CH_2$ of formula 1;

$R_4$ is an optionally substituted straight or branched chain alkylene group or a polyvalent branched chain alkyl group with 1 to 300 carbon atoms, wherein optionally
  (a) one or more carbon atoms are replaced by oxygen
  (b) one or more carbon atoms are replaced by nitrogen carrying a hydrogen atom, and an adjacent carbon atom is substituted by oxo, representing an amide function —NH—CO—;
  (c) one or more carbon atoms are replaced by oxygen, and an adjacent carbon atom is substituted by oxo, representing an ester function —O—CO—;
  (d) the bond between two adjacent carbon atoms is a double or a triple bond, representing a function —CH=CH— or —C≡C—;
  (e) one or more carbon atoms are replaced by a phenylene, a saturated or unsaturated cycloalkylene, a saturated or unsaturated bicycloalkylene, a bridging heteroaromatic or a bridging saturated or unsaturated heterocyclyl group; and/or
  (f) two adjacent carbon atoms are replaced by a disulfide linkage —S—S—; and L is amino or azido.

22. A compound according to claim 21 wherein
$R_4$ is a straight chain alkylene group of 10 to 40 carbon atoms optionally substituted by oxo wherein up to 12 carbon atoms are replaced by oxygen and zero, one or two carbon atoms are replaced by nitrogen.

23. A method for detecting a protein of interest, which comprises contacting an AGT fusion protein comprising the protein of interest with an AGT substrate carrying a label, and detecting the AGT fusion protein using the label in a system designed for recognising the label, and wherein the AGT substrate carrying the label is a compound of formula 1 according to claim 1.

* * * * *